(12) United States Patent
Gravestock et al.

(10) Patent No.: US 7,199,143 B2
(45) Date of Patent: *Apr. 3, 2007

(54) CHEMICAL COMPOUNDS

(75) Inventors: Michael Barry Gravestock, Waltham, MA (US); Neil James Hales, Maccleslesfield (GB); Folkert Reck, Waltham, MA (US); Fei Zhou, Waltham, MA (US); Paul Robert Fleming, Waltham, MA (US); Daniel Robert Carcanague, Waltham, MA (US)

(73) Assignee: AstraZeneca AB, Sodertajle (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/505,902

(22) PCT Filed: Feb. 25, 2003

(86) PCT No.: PCT/GB03/00791

§ 371 (c)(1),
(2), (4) Date: Aug. 26, 2004

(87) PCT Pub. No.: WO03/072576

PCT Pub. Date: Sep. 4, 2003

(65) Prior Publication Data

US 2005/0182112 A1     Aug. 18, 2005

Related U.S. Application Data

(60) Provisional application No. 60/360,688, filed on Feb. 28, 2002.

(51) Int. Cl.
*A61K 31/442* (2006.01)
*C07D 413/10* (2006.01)
*C07D 263/20* (2006.01)

(52) U.S. Cl. ...................................... 514/376; 548/229
(58) Field of Classification Search ................ 548/229; 514/376
See application file for complete search history.

(56) References Cited

U.S. PATENT DOCUMENTS 6,028,090 A * 2/2000 Gante et al. ................. 514/376

FOREIGN PATENT DOCUMENTS

EP     0 184 170 A2     11/1985

(Continued)

OTHER PUBLICATIONS

Bundgaard, H., "Design of prodrugs: Bioreversible derivatives for various functional groups and chemical entities", In Design of Pro-drugs, Bundgaard, H., eds. (Elsevier Science Publishers B.V.), pp. 1-92 (1985).

(Continued)

*Primary Examiner*—Joseph K. McKane
*Assistant Examiner*—Andrew B. Freistein

(57) ABSTRACT

Compounds of the formula (I), or a pharmaceutically-acceptable salt, or an in-vivo-hydrolysable ester thereof,

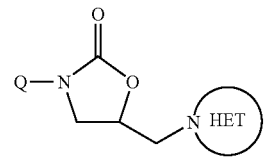

(I)

wherein —N-HET is, for example, (Ic) or (If)

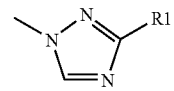

(Ic)

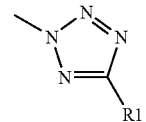

(If)

wherein R1 is, for example, halogen or a (1–4C)alkyl group which is substituted by one substituent selected from, for example, hydroxy, (1–4C)alkoxy, amino, cyano or azido; Q is selected from, for example, Q1

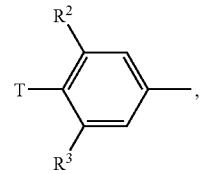

Q1 wherein $R^2$ and $R^3$ are independently hydrogen or fluoro; T is selected from a range of groups, for example,

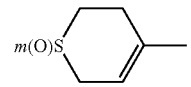

(TC12b)

wherein m is 0, 1 or 2; are useful as antibacterial agents; and processes for their manufacture and pharmaceutical compositions containing them are described.

8 Claims, No Drawings

FOREIGN PATENT DOCUMENTS

| | | |
|---|---|---|
| WO | WO-95/07271 A1 | 3/1995 |
| WO | WO-97/14690 A1 | 4/1997 |
| WO | WO-97/27188 A1 | 7/1997 |
| WO | WO-97/30995 A1 | 8/1997 |
| WO | WO-97/31917 A1 | 9/1997 |
| WO | WO-97/43280 A1 | 11/1997 |
| WO | WO-98/01446 A1 | 1/1998 |
| WO | WO-98/01447 A1 | 1/1998 |
| WO | WO-99/10342 A1 | 3/1999 |
| WO | WO 99/10343 A1 | 3/1999 |
| WO | WO-99/11642 A1 | 3/1999 |
| WO | WO-99/28317 A1 | 6/1999 |
| WO | WO-99/64416 A2 | 12/1999 |
| WO | WO-99/64417 A2 | 12/1999 |
| WO | WO-00/21960 A1 | 4/2000 |
| WO | WO-01/40222 A1 | 6/2001 |
| WO | WO-01/40236 A2 | 6/2001 |
| WO | WO-01/58885 A1 | 8/2001 |
| WO | WO-01/81350 A1 | 11/2001 |
| WO | WO-02/080841 A2 | 10/2002 |
| WO | WO-02/081468 A1 | 10/2002 |
| WO | WO-02/081469 A1 | 10/2002 |
| WO | WO-02/081470 A1 | 10/2002 |
| WO | WO-02/036917 A1 | 12/2002 |
| WO | WO-02/096890 A2 | 12/2002 |
| WO | WO-02/096916 A1 | 12/2002 |
| WO | WO-02/096918 A1 | 12/2002 |
| WO | WO-03/022824 A1 | 3/2003 |
| WO | WO-03/022840 A1 | 3/2003 |
| WO | WO-03/035073 A1 | 5/2003 |
| WO | WO-03/035648 A1 | 5/2003 |
| WO | WO-2004/048350 A2 | 6/2004 |
| WO | WO-2004/048370 A1 | 6/2004 |
| WO | WO-2004/048392 A1 | 6/2004 |
| WO | WO-2004/056816 A1 | 7/2004 |
| WO | WO-2004/056817 A1 | 7/2004 |
| WO | WO-2004/056818 A1 | 7/2004 |
| WO | WO-2004/056819 A1 | 7/2004 |
| WO | WO-2004/078753 A1 | 9/2004 |
| WO | WO-2004/083205 A1 | 9/2004 |
| WO | WO-2004/083206 A1 | 9/2004 |

OTHER PUBLICATIONS

Gregory, W.A., et al., "Antibacterials. Synthesis and Structure-Activity Studies of 3-Aryl-2-oxooxazolidines. 1. The "B" Group," J. Med. Chem., 32:1673-1681 (1989).

Phillips, O.A., et al., "Synthesis and Antibacterial Activity of 5-Substituted Oxazolidinones," Bioorganic & Medicinal Chemistry, 11:35-41 (2003).

Reck, F., et al., "Novel (5R)-1,2,3-Triazolylmethyl Oxazolidinones: 4-Substituted 1,2,3-Triazoles as Antibacterial Agents with Reduced Activity against Monoamine Oxidase A," Poster at ICAAC 2004.

* cited by examiner

CHEMICAL COMPOUNDS

CROSS-REFERENCE TO RELATED APPLICATIONS

This application is a national stage filing under 35 U.S.C. 371 of International Application No. PCT/GB03/00791, filed Feb. 25, 2003, which claims priority from U.S. application Ser. No. 60/360,688, filed Feb. 28, 2002, the specification of which is incorporated by reference herein. International Application No. PCT/GB03/00791 was published under PCT Article 21(2) in English.

The present invention relates to antibiotic compounds and in particular to antibiotic compounds containing a substituted oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as principally effective against Gram-positive pathogens.

Gram-positive pathogens, for example *Staphylococci, Enterococci,* and *Streptococci* are particularly important because of the development of resistant strains which are both difficult to treat and difficult to eradicate from the hospital environment once established. Examples of such strains are methicillin resistant *staphylococcus* (MRSA), *methicillin* resistant coagulase negative staphylococci (MRCNS), *penicillin* resistant *Streptococcus pneumoniae* and multiply resistant *Enterococcus faecium.*

The major clinically effective antibiotic for treatment of such resistant Gram-positive pathogens is vancomycin. Vancomycin is a glycopeptide and is associated with various toxicities including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis.*

Certain antibacterial compounds containing an oxazolidinone ring have been described in the art (for example, Walter A. Gregory et al in J. Med. Chem. 1990, 33, 2569–2578 and Chung-Ho Park et al in J. Med. Chem. 1992, 35, 1156–1165). Such antibacterial oxazolidinone compounds with a 5-acetamidomethyl side-chain may be subject to mammalian peptidase metabolism. Furthermore, bacterial resistance to known antibacterial agents may develop, for example, by (i) the evolution of active binding sites in the bacteria rendering a previously active pharmacophore less effective or redundant, (ii) the evolution of means to chemically deactivate a given pharmacophore and/or (iii) the development and/or up-regulation of efflux mechanisms. Therefore, there remains an ongoing need to find new antibacterial agents with a favourable pharmacological profile, in particular for compounds containing new pharmacophores.

Additionally, certain antibacterial compounds containing an oxazolidinone ring have activity against the enzyme mono-amine oxidase (MAO), for instance compounds with amidomethyl or hydroxymethyl side chains at C-5 of the oxazolidinone ring. This may potentially lead to undesirable properties such as elevation in blood pressure when administered to a patient, or potentially cause drug-drug interactions. Therefore, there remains an ongoing need to find new antibacterial agents of the oxazolidinone class with a more favourable profile against MAO.

We have discovered a new class of antibiotic compounds containing an oxazolidinone ring substituted by a 5-azolylmethyl moiety in which the azole group is linked via a nitrogen atom and is itself further substituted. These compounds have useful activity against Gram-positive pathogens including MRSA and MRCNS and, in particular, against various strains exhibiting resistance to vancomycin and against *E. faecium* strains resistant to both aminoglycosides and clinically used β-lactams, but also to certain fastidious Gram negative strains such as *H. influenzae, M. catarrhalis* and chlamydial strains. The compounds of the invention also show a favourable, decreased, MAO potency compared with other oxazolidinone analogues from the prior art.

Accordingly in a first aspect, the present invention provides a compound of the formula (I), or a pharmaceutically-acceptable salt, or an in-vivo-hydrolysable ester thereof,

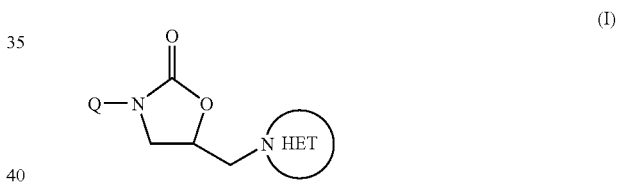

(I)

wherein —N-HET is selected from the structures (Ia) to (If) below:

(Ia)

(Ib)

(Ic)

(Id)

-continued

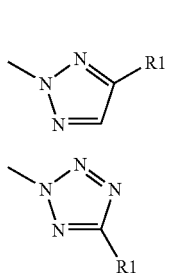
(Ie)

(If)

wherein u and v are independently 0 or 1;

R1 is selected from a substituent from the group (R1a) wherein R1 is halogen, hydroxy, (1–4C)alkoxy, (2–4C)alkenyloxy, (2–4C)alkenyl, (2–4C)alkynyl (optionally substituted on the terminal carbon by $CH_2=CH-$, di(1–4C)alkylamino, AR2, AR2a or AR2b, wherein AR2, AR2a and AR2b are defined hereinbelow), (3–6C)cycloalkyl, (3–6C)cycloalkenyl, amino, (1–4C) alkylamino, di-(1–4C)alkylamino, (2–4C)alkenylamino, (1–4C)alkyl-S(O)q- (wherein q is 0, 1 or 2), (1–4C) alkylcarbonylamino;

or R1 is selected from the group (R1b) wherein R1 is a (1–4C)alkyl group which is substituted by one substituent selected from hydroxy, halo, (1–4C)alkoxy, amino, (1–4C)alkylamino, di(1–4C)alkylamino, cyano, azido, (2–4C)alkenyloxy, (1–4C)alkyl-S(O)q- (wherein q is 0, 1 or 2), AR1-S(O)q- (wherein q is 0, 1 or 2 and AR1 is defined hereinbelow), AR2-S(O)q- (wherein q is 0, 1 or 2), AR2a-S(O)q- (wherein q is 0, 1 or 2), benzyl-S(O)q- (wherein q is 0, 1 or 2), (3–6C) cycloalkyl, (3–6C)cycloalkenyl, (1–4C)alkyl-OCO—NH—, (1–4C)alkyl-NHCO—O—, (1–4C)alkylaminocarbonyl, di(1–4C)alkylaminocarbonyl, $H_2NC(=NH)S—$;

or R1 is selected from a group of formula (R1c1):

(R1c1) a fully saturated 4-membered monocyclic ring containing 1 or 2 heteroatoms independently selected from O, N and S (optionally oxidised), and linked via a ring nitrogen or carbon atom; or or R1 is selected from the group (R1d) cyano, nitro, azido, formyl, (1–4C)alkylcarbonyl, (1–4C)alkoxycarbonyl, $H_2NC(O)—$, $((1–4C)alkyl)NHC(O)—$;

and wherein at each occurrence of an R1 substituent containing an alkyl, alkenyl, alkynyl, cycloalkyl or cycloalkenyl moiety in (R1a), (R1b) or (R1c1) each such moiety is optionally further substituted on an available carbon atom with one, two, three or more substituents independently selected from F, Cl Br, OH and CN;

Q is selected from Q1 to Q6:

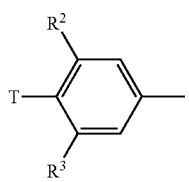
Q1

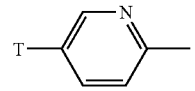
Q2

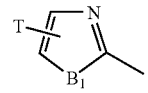
Q3

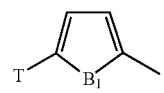
Q4

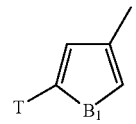
Q5

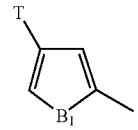
Q6 wherein $R^2$ and $R^3$ independently selected from H, F, Cl, $CF_3$, OMe, SMe, Me and Et;

wherein $B_1$ is O or S;

wherein T is selected from the groups in (TA) to (TE) below (wherein AR1, AR2, AR2a, AR2b, AR3, AR3a, AR3b, AR4, AR4a, CY1 and CY2 are defined hereinbelow);

(TA) T is selected from the following groups:

(TAa) AR1 or AR3; or (TAb) a group of formula (TAb1) to (TAb6):

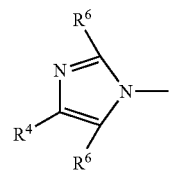
(TAb1)

(TAb2)

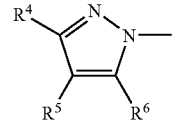
(TAb3)

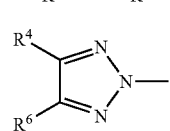
(TAb4)

-continued

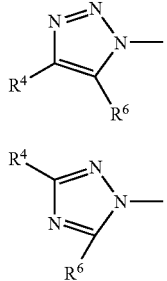
(TAb5)

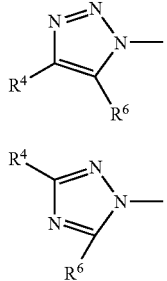
(TAb6)

wherein:

R⁶ is selected (independently where appropriate) from hydrogen, (1–4C)alkyl, (1–4C)alkoxycarbonyl, (1–4C)alkanoyl, carbamoyl and cyano;

R⁴ and R⁵ are independently selected from hydrogen, halo, trifluoromethyl, cyano, azido, nitro, (1–4C)alkoxy, (1–4C)alkylS(O)$_q$— (q is 0, 1 or 2), (1–4C)alkanoyl, (1–4C)alkoxycarbonyl, benzyloxy-(1–4C)alkyl, (2–4C)alkanoylamino, hydroxyimino, (1–4C)alkoxyimino, —CONRcRv and —NRcRv wherein any (1–4C)alkyl group contained in the preceding values for R⁴ and R⁵ is optionally substituted by up to three substituents independently selected from hydroxy or azido (neither of such substituents on C1 of an alkoxy group, and excluding geminal disubstitution), oxo, trifluoromethyl, cyano, nitro, (1–4C)alkoxy, (2–4C)alkanoyloxy, hydroxyimino, (1–4C)alkoxyimino, (1–4C)alkylS(O)$_q$— (q is 0, 1 or 2), (1–4C)alkylSO$_2$—NRv-, (1–4C)alkoxycarbonyl, —CONRcRv, and —NRcRv (not on C1 of an alkoxy group, and excluding geminal disubstitution); wherein Rv is hydrogen or (1–4C)alkyl and Rc is as hereinafter defined;

R⁴ and R⁵ may further be independently selected from (1–4C)alkyl {optionally substituted by up to three substituents independently selected from hydroxy or azido (both of such substituents excluded from geminal disubstitution), oxo, trifluoromethyl, cyano, nitro, (1–4C)alkoxy, (2–4C)alkanoyloxy, hydroxyimino, (1–4C)alkoxyimino, (1–4C)alkylS(O)$_q$— (q is 0, 1 or 2), (1–4C)alkylSO$_2$—NRv-, (1–4C)alkoxycarbonyl, —CONRcRv, and —NRcRv (excluding geminal disubstitution); wherein Rv is hydrogen or (1–4C)alkyl}; Rc is as hereinafter defined;

and wherein any (1–4C)alkyl group contained in the immediately preceding optional substituents (when R⁴ and R⁵ are independently (1–4C)alkyl) is itself optionally substituted by up to three substituents independently selected from hydroxy (not on C1 of an alkoxy group, and excluding geminal disubstitution), oxo, trifluoromethyl, cyano, nitro, (1–4C)alkoxy, (2–4C)alkanoyloxy, hydroxyimino, (1–4C)alkoxyimino, (1–4C)alkylS(O)$_q$— (q is 0, 1 or 2), (1–4C)alkylSO$_2$—NRv-, (1–4C)alkoxycarbonyl, —CONRcRv, and —NRcRv (not on C1 of an alkoxy group, and excluding geminal disubstitution); wherein Rv is hydrogen or (1–4C)alkyl and Rc is as hereinafter defined;

or R⁴ is selected from one of the groups in (TAba) to (TAbc) below, or (where appropriate) one of R⁴ and R⁵ is selected from the above list of R⁴ and R⁵ values, and the other is selected from one of the groups in (TAba) to (TAbc) below:

(TAba) a group of the formula (TAba1)

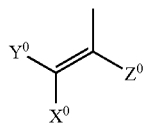
(TAba1)

wherein Z⁰ is hydrogen or (1–4C)alkyl;

X⁰ and Y⁰ are independently selected from hydrogen, (1–4C)alkyl, (1–4C)alkoxycarbonyl, halo, cyano, nitro, (1–4C)alkylS(O)$_q$— (q is 0, 1 or 2), RvRwNSO$_2$—, trifluoromethyl, pentafluoroethyl, (1–4C)alkanoyl and —CONRvRw [wherein Rv is hydrogen or (1–4C)alkyl; Rw is hydrogen or (1–4C)alkyl]; or one of X⁰ and Y⁰ is selected from the above list of X⁰ and Y⁰ values, and the other is selected from phenyl, phenylcarbonyl, —S(O)$_q$-phenyl (q is 0, 1 or 2), N-(phenyl)carbamoyl, phenylaminosulfonyl, AR2, (AR2)-CO—, (AR2)-S(O)$_q$— (q is 0, 1 or 2), N-(AR2)carbamoyl and (AR2)aminosulfonyl; wherein any phenyl group in (TAba) may be optionally substituted by up to three substituents independently selected from (1–4C)alkyl, cyano, trifluoromethyl, nitro, halo and (1–4C)alkylsulfonyl;

(TAbb) an acetylene of the formula -≡—H or -≡-(1–4C)alkyl;

(TAbc) —X¹—Y¹-AR2, —X¹—Y¹-AR2a, —X¹—Y¹-AR2b, —X¹—Y¹-AR3, —X¹—Y¹-AR3a or —X¹—Y¹-AR3b;

wherein X¹ is a direct bond or —CH(OH)— and Y¹ is —(CH$_2$)$_m$—, —(CH$_2$)$_n$—NH—(CH$_2$)$_m$—, —CO—(CH$_2$)$_m$—, —CONH—(CH$_2$)$_m$—, —C(=S)NH—(CH$_2$)$_m$— or —C(=O)O—(CH$_2$)$_m$—;

or wherein X¹ is —(CH$_2$)$_n$— or —CH(Me)-(CH$_2$)$_m$— and Y¹ is —(CH$_2$)$_m$—NH—(CH$_2$)$_m$—, —CO—(CH$_2$)$_m$—, —CONH—(CH$_2$)$_m$—, —C(=S)NH—(CH$_2$)$_m$—, —C(=O)O—(CH$_2$)$_m$— or —S(O)$_q$—(CH$_2$)$_m$—;

or wherein X¹ is —CH$_2$O—, —CH$_2$NH— or —CH$_2$N((1–4C)alkyl)- and

Y¹ is —CO—(CH$_2$)$_m$—, —CONH—(CH$_2$)$_m$— or —C(=S)NH—(CH$_2$)$_m$—; and additionally Y¹ is —SO$_2$— when X¹ is —CH$_2$NH— or —CH$_2$N((1–4C)alkyl)-, and Y¹ is —(CH$_2$)$_m$— when X¹ is —CH$_2$O— or —CH$_2$N((1–4C)alkyl)-; wherein n is 1, 2 or 3; m is 0, 1, 2 or 3 and q is 0, 1 or 2; and when Y¹ is —(CH$_2$)$_m$—NH—(CH$_2$)$_m$— each m is independently selected from 0, 1, 2 or 3; or (TB) T is selected from halo, formyl or —NRv¹Rw¹; or is selected from the following groups:

(TBa) R¹⁰CO—, R¹⁰S(O)$_q$— (q is 0, 1 or 2) or R¹⁰CS— wherein R¹⁰ is selected from the following groups:

(TBaa) CY1 or CY2;

(TBab) (1–4C)alkoxycarbonyl, trifluoromethyl, —NRvRw, ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl or 2-(AR2)ethenyl; or (TBac) (1–4C)alkyl {optionally substituted by one or more groups each independently selected from hydroxy, (1–4C)

alkoxy, (1–4C)alkanoyl, cyano, halo, trifluoromethyl, (1–4C)alkoxycarbonyl, —NRvRw, (1–6C)alkanoylamino, (1–4C)alkoxycarbonylamino, N-(1–4C)alkyl-N-(1–6C)alkanoylamino, (1–4C)alkylS(O)$_q$— (q is 0, 1 or 2), CY1, CY2, AR1, (1–4C)alkylS(O)$_p$NH— or (1–4C)alkylS(O)$_p$-((1–4C)alkyl)N— (p is 1 or 2)};

wherein Rv is hydrogen or (1–4C)alkyl; Rw is hydrogen or (1–4C)alkyl; Rv$^1$ is hydrogen, (1–4C)alkyl or (3–8C)cycloalkyl; Rw$^1$ is hydrogen, (1–4C)alkyl, (3–8C)cycloalkyl, formyl, (1–4C)alkyl-CO— or (1–4C)alkylS(O)$_q$— (q is 1 or 2); or (TC) T is selected from a group of formula (TC1) to (TC4):

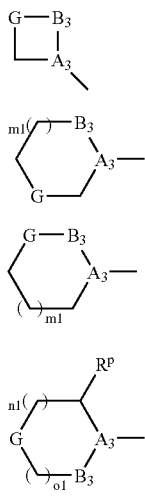

(TC1)

(TC2)

(TC3)

(TC4)

wherein in (TC1): >A$_3$-B$_3$— is >C(Rq)-CH(Rr)- or >N—CH$_2$— and G is —O—, —S—, —SO—, —SO$_2$— or >N(Rc);

wherein in (TC2): m1 is 0, 1 or 2; >A$_3$-B$_3$— is >C═C(Rr)- or >C(Rq)-CH(Rr)- or >N—CH$_2$— and G is —O—, —S—, —SO—, —SO$_2$— or >N(Rc);

wherein in (TC3): m1 is 0, 1 or 2; >A$_3$-B$_3$— is >C(Rq)-CH(Rr)- (other than when Rq and Rr are both together hydrogen) or >N—CH$_2$— and G is —O—, —S—, —SO—, —SO$_2$— or >N(Rc);

wherein in (TC4): n1 is 1 or 2; o1 is 1 or 2 and n1+o1=2 or 3; >A$_3$-B$_3$— is >C═C(Rr)- or >C(Rq)-CH(Rr)- or >N—CH$_2$— and G is —O—, —S—, —SO—, —SO$_2$— or >N(Rc); Rp is hydrogen, (1–4C)alkyl (other than when such substitution is defined by >A$_3$-B$_3$—), hydroxy, (1–4C)alkoxy or (1–4C)alkanoyloxy;

wherein in (TC1), (TC2) and (TC4); m1, n1 and o1 are as defined hereinbefore in (TC): >A$_3$-B$_3$— is >N—CH$_2$— and G is >(R$^{11}$)(R$^{12}$), >C═O, >C—OH, >C-(1–4C)alkoxy, >C═N—OH, >C═N-(1–4C)alkoxy, >C═N—NH-(1–4C)alkyl, >C═N—N((1–4C)alkyl)$_2$ (the last two (1–4C)alkyl groups above in G being optionally substituted by hydroxy) or >C═N—N—CO-(1–4C)alkoxy; wherein >represents two single bonds;

Rq is hydrogen, hydroxy, halo, (1–4C)alkyl or (1–4C)alkanoyloxy;

Rr is (independently where appropriate) hydrogen or (1–4C)alkyl;

R$^{11}$ is hydrogen, (1–4C)alkyl, fluoro(1–4C)alkyl, (1–4C)alkyl-thio-(1–4C)alkyl or hydroxy-(1–4C)alkyl and R$^{12}$ is —[C(Rr)(Rr)]$_{m2}$-N(Rr)(Rc) wherein m2 is 0, 1 or 2;

and, other than the ring substitution defined by G, >A$_3$-B$_3$— and Rp, each ring system may be optionally further substituted on a carbon atom not adjacent to the link at >A$_3$- by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, ARc-oxymethyl, ARc-thiomethyl, oxo (═O) (other than when G is >N-Rc and Rc is group (Rc2) defined hereinbefore) or independently selected from Rc (if such substituents are not already defined herein in (TC)); and also hydroxy or halo (the last two optional substituents only when G is —O— or —S—);

wherein ARc is selected from AR1, AR2, AR2a, AR2b, CY1 and CY2 defined hereinafter and Rc is selected from groups (Rc1) to (Rc5) defined hereinafter; or (TD) T is selected from the following groups:

(TDa) a bicyclic spiro-ring system of formula (TDa1) to (TDa9):

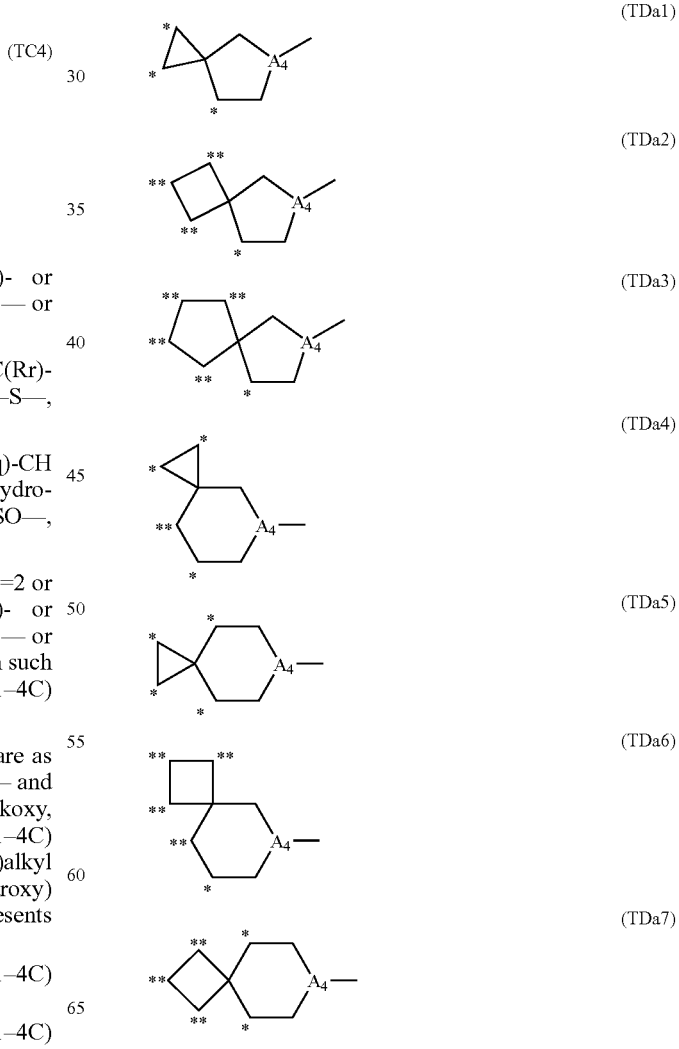

(TDa1)

(TDa2)

(TDa3)

(TDa4)

(TDa5)

(TDa6)

(TDa7)

-continued (TDa8)

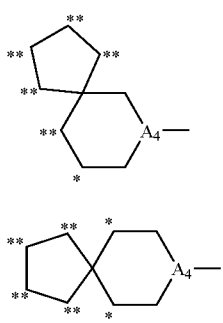

(TDa9)

wherein;

(i) the $A_4$ linking group is a nitrogen atom or an sp$^3$ or sp$^2$ carbon atom (with the double bond, where appropriate, orientated in either direction); and (ii) one of the ring carbon atoms at positions marked * and ** is replaced by one of the following groups —NRc-, >CH—NHRc, >CH—NRc-(1–4C)alkyl, >CH—CH$_2$—NHRc, >CH—CH$_2$—NRc-(1–4C)alkyl [wherein a central —CH$_2$— chain link is optionally mono- or di-substituted by (1–4C)alkyl]; with the provisos that positions marked * are not replaced by —NH— in the ring containing the $A_4$ link when $A_4$ is a nitrogen atom or an sp$^2$ carbon atom, and that positions marked * are not replaced by —NH— in the three membered ring in (TDa1), (TDa4) and (TDa5); and (iii) the ring system is optionally (further) substituted on an available ring carbon atom by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR2-oxymethyl, AR2-thiomethyl, oxo (=O) (other than when the ring contains an >N-Rc and Rc is group (Rc2)) and also hydroxy or halo; and Rc is selected from groups (Rc1) to (Rc5) defined hereinafter; or (TDb) a 7-, 8- or 9-membered bicyclic ring system containing a bridge of 0, 1 or 2 carbon atoms of formula (TDb1) to (TDb14):

7-membered ring skeletons

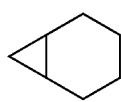

[4,1,0]

(TDb1)

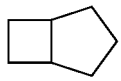

[3,2,0]

(TDb2)

[3,1,1]

(TDb3)

[2,2,1]

(TDb4)

8-membered ring skeletons

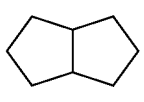

[3,3,0]

(TDb5)

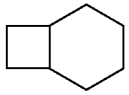

[4,2,0]

(TDb6)

[4,1,1]

(TDb7)

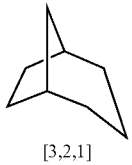

[3,2,1]

(TDb8)

[2,2,2]

(TDb9)

9-membered ring skeletons

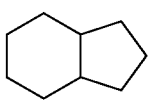

[4,3,0]

(TDb10)

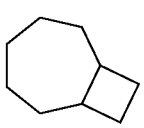

[5,2,0]

(TDb11)

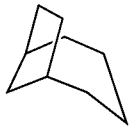

[4,2,1]

(TDb12)

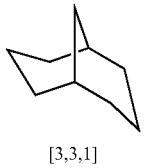

[3,3,1]

(TDb13)

-continued

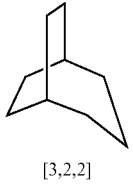

[3,2,2] (TDb14)

wherein;
(i) the ring system contains 0, 1 or 2 ring nitrogen atoms (and optionally a further O or S ring heteroatom), and when present the ring nitrogen, O or S heteroatom/s are at any position other than as part of the 3-membered ring in (TDb1);
(ii) the ring system is linked via a ring nitrogen atom or a ring sp$^3$ or sp$^2$ carbon atom (with the double bond, where appropriate, orientated in either direction) from any position in either ring [other than from a bridgehead position or from an sp$^2$ carbon atom in the 4-membered ring in (TDb2), (TDb6) and (TDb11)];
(iii) one of the ring carbon atoms at a position not adjacent to the linking position, is replaced (other than when the ring contains an O or S heteroatom) by one of the following groups —NRc- [not at a bridgehead position], >C(H)—NHRc, >C(H)—NRc-(1–4C)alkyl, >C(H)—CH$_2$—NHRc, >C(H)—CH$_2$—NRc-(1–4C)alkyl [wherein the hydrogen atom shown in brackets is not present when the replacement is made at a bridgehead position and wherein a central —CH$_2$— chain link is optionally mono- or di-substituted by (1–4C)alkyl]; with the proviso that when the ring system is linked via a ring nitrogen atom or an sp$^2$ carbon atom any replacement of a ring carbon atom by —NRc-, O or S is at least two carbon atoms away from the linking position; and
(iv) the ring system is optionally (further) substituted on an available ring carbon atom as for the bicyclic spiro-ring systems described in (TDa); and Rc is selected from groups (Rc1) to (Rc5) defined hereinafter; or
(TE) T is selected from the following groups (TE1) to (TE3):

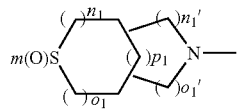

(TE1)

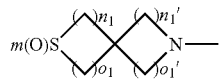

(TE2)

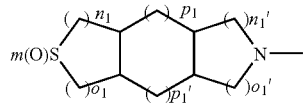

(TE3)

wherein m is 0, 1 or 2; and ( )$n_1$, ( )$o_1$, ( )$n_{1'}$, ( )$o_{1'}$, ( )$p_1$ and ( )$p_{1'}$ represent chains of carbon atoms (optionally substituted as defined for AR1 hereinafter) of length $n_1$, $o_1$, $n_{1'}$, $o_{1'}$, $p_1$ and $p_{1'}$ respectively, and are independently 0–2, with the proviso that in (TE1) and (TE2) the sum of $n_1$, $o_1$, $n_{1'}$ and $o_{1'}$ does not exceed 8 (giving a maximum ring size of 14 in (TE1) and 11 in (TE2)), and in (TE3) the sum of $n_1$, $o_1$, $n_{1'}$, $o_{1'}$, $p_1$ and $p_{1'}$ does not exceed 6 (giving a maximum ring size of 12);

wherein Rc is selected from groups (Rc1) to (Rc5):
(Rc1) (1–6C)alkyl {optionally substituted by one or more (1–4C)alkanoyl groups (including geminal disubstitution) and/or optionally monosubstituted by cyano, (1–4C) alkoxy, trifluoromethyl, (1–4C)alkoxycarbonyl, phenyl (optionally substituted as for AR1 defined hereinafter), (1–4C)alkylS(O)$_q$— (q is 0, 1 or 2); or, on any but the first carbon atom of the (1–6C)alkyl chain, optionally substituted by one or more groups (including geminal disubstitution) each independently selected from hydroxy and fluoro, and/or optionally monosubstituted by oxo, —NRvRw [wherein Rv is hydrogen or (1–4C)alkyl; Rw is hydrogen or (1–4C)alkyl], (1–6C)alkanoylamino, (1–4C)alkoxycarbonylamino, N-(1–4C)alkyl-N-(1–6C)alkanoylamino, (1–4C)alkylS(O)$_p$NH— or (1–4C)alkylS(O)$_p$—((1–4C)alkyl)N— (p is 1 or 2)};
(Rc2) formyl, R$^{13}$CO—, R$^{13}$SO$_2$— or R$^{13}$CS— wherein R$^{13}$ is selected from (Rc2a) to (Rc2e):
(Rc2a) AR1, AR2, AR2a, AR2b, AR3, AR3a, AR3b, AR4, AR4a, CY1, CY2; (Rc2b) (1–4C)alkoxycarbonyl, trifluoromethyl, —NRvRw [wherein Rv is hydrogen or (1–4C) alkyl; Rw is hydrogen or (1–4C)alkyl], ethenyl, 2-(1–4C) alkylethenyl, 2-cyanoethenyl, 2-cyano-2-((1–4C)alkyl) ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl, 2-(AR2a)ethenyl;
(Rc2c) (1–10C)alkyl {optionally substituted by one or more groups (including geminal disubstitution) each independently selected from hydroxy, (1–10C)alkoxy, (1–4C)alkoxy-(1–4C)alkoxy, (1–4C)alkoxy-(1–4C)alkoxy-(1–4C)alkoxy, (1–4C)alkanoyl, carboxy, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], and amino; and/or optionally substituted by one group selected from phosphonate [phosphono, —P(O) (OH)$_2$, and mono- and di-(1–4C)alkoxy derivatives thereof], phosphinate [—P(OH)$_2$ and mono- and di-(1–4C)alkoxy derivatives thereof], cyano, halo, trifluoromethyl, (1–4C) alkoxycarbonyl, (1–4C)alkoxy-(1–4C)alkoxycarbonyl, (1–4C)alkoxy-(1–4C)alkoxy-(1–4C)alkoxycarbonyl, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$-((1–4C)alkyl)N—, fluoro(1–4C)alkylS (O)$_p$NH—, fluoro(1–4C)alkylS(O)$_p$((1–4C)alkyl)N—, (1–4C)alkylS(O)$_q$— [the (1–4C)alkyl group of (1–4C) alkylS(O)$_q$— being optionally substituted by one substituent selected from hydroxy, (1–4C)alkoxy, (1–4C)alkanoyl, phosphoryl [—O—P(O)(OH)$_2$, and mono- and di-(1–4C) alkoxy derivatives thereof], phosphiryl [—O—P(OH)$_2$ and mono- and di-(1–4C)alkoxy derivatives thereof], amino, cyano, halo, trifluoromethyl, (1–4C)alkoxycarbonyl, (1–4C) alkoxy-(1–4C)alkoxycarbonyl, (1–4C)alkoxy-(1–4C) alkoxy-(1–4C)alkoxycarbonyl, carboxy, (1–4C)alkylamino, di((1–4C)alkyl)amino, (1–6C)alkanoylamino, (1–4C) alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$—((1–4C)alkyl)N—, (1–4C)alkylS(O)$_q$—, AR1-S(O)$_q$—, AR2-S(O)$_q$—, AR3-S(O)$_q$— and also AR2a, AR2b, AR3a and AR3b versions of AR2 and AR3 containing groups], CY1, CY2, AR1, AR2, AR3, AR1-O—, AR2-O—, AR3-O—, AR1-S(O)$_q$—, AR2-S(O)$_q$—, AR3—S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups};

(Rc2d) R$^{14}$C(O)O(1–6C)alkyl wherein R$^{14}$ is AR1, AR2, (1–4C)alkylamino (the (1–4C)alkyl group being optionally substituted by (1–4C)alkoxycarbonyl or by carboxy), benzyloxy-(1–4C)alkyl or (1–10C)alkyl {optionally substituted as defined for (Rc2c)};

(Rc2e) R$^{15}$O— wherein R$^{15}$ is benzyl, (1–6C)alkyl {optionally substituted as defined for (Rc2c)}, CY1, CY2 or AR2b;

(Rc3) hydrogen, cyano, 2-cyanoethenyl, 2-cyano-2-((1–4C)alkyl)ethenyl, 2-((1–4C)alkylaminocarbonyl)ethenyl, 2-((1–4C)alkoxycarbonyl)ethenyl, 2-nitroethenyl, 2-nitro-2-((1–4C)alkyl)ethenyl, 2-(AR1)ethenyl, 2-(AR2)ethenyl, or of the formula (Rc3a)

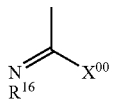

(Rc3a)

wherein X$^{00}$ is —OR$^{17}$, —SR$^{17}$, —NHR$^{17}$ and —N(R$^{17}$)$_2$; wherein R$^{17}$ is hydrogen (when X$^{00}$ is —NHR$^{17}$ and —N(R$^{17}$)$_2$), and R$^{17}$ is (1–4C)alkyl, phenyl or AR2 (when X$^{00}$ is —OR$^{17}$, —SR$^{17}$ and —NHR$^{17}$); and R$^{16}$ is cyano, nitro, (1–4C)alkylsulfonyl, (4–7C)cycloalkylsulfonyl, phenylsulfonyl, (1–4C)alkanoyl and (1–4C)alkoxycarbonyl;

(Rc4) trityl, AR1, AR2, AR2a, AR2b, AR3, AR3a, AR3b;

(Rc5) RdOC(Re)=CH(C=O)—, RfC(=O)C(=O)—, RgN=C(Rh)C(=O)— or RiNHC(Rj)=CHC(=O)— wherein Rd is (1–6C)alkyl; Re is hydrogen or (1–6C)alkyl, or Rd and Re together form a (3–4C)alkylene chain; Rf is hydrogen, (1–6C)alkyl, hydroxy(1–6C)alkyl, (1–6C)alkoxy(1–6C)alkyl, —NRvRw [wherein Rv is hydrogen or (1–4C)alkyl; Rw is hydrogen or (1–4C)alkyl], (1–6C)alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy; Rg is (1–6C)alkyl, hydroxy or (1–6C)alkoxy; Rh is hydrogen or (1–6C)alkyl; Ri is hydrogen, (1–6C)alkyl, AR1, AR2, AR2a, AR2b and Rj is hydrogen or (1–6C)alkyl;

wherein

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any —O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring;

wherein; optional substituents on AR1, AR2, AR2a, AR2b, AR3, AR3a, AR3b, AR4, AR4a, CY1 and CY2 are (on an available carbon atom) up to three substituents independently selected from (1–4C)alkyl {optionally substituted by substituents selected independently from hydroxy, trifluoromethyl, (1–4C)alkyl S(O)$_q$— (q is 0, 1 or 2), (1–4C)alkoxy, (1–4C)alkoxycarbonyl, cyano, nitro, (1–4C)alkanoylamino, —CONRvRw or —NRvRw}, trifluoromethyl, hydroxy, halo, nitro, cyano, thiol, (1–4C)alkoxy, (1–4C)alkanoyloxy, dimethylaminomethyleneaminocarbonyl, di(N-(1–4C)alkyl)aminomethylimino, carboxy, (1–4C)alkoxycarbonyl, (1–4C)alkanoyl, (1–4C)alkylSO$_2$amino, (2–4C)alkenyl {optionally substituted by carboxy or (1–4C)alkoxycarbonyl}, (2–4C)alkynyl, (1–4C)alkanoylamino, oxo (=O), thioxo (=S), (1–4C)alkanoylamino {the (1–4C)alkanoyl group being optionally substituted by hydroxy}, (1–4C)alkyl S(O)$_q$— (q is 0, 1 or 2) {the (1–4C)alkyl group being optionally substituted by one or more groups independently selected from cyano, hydroxy and (1–4C)alkoxy}, —CONRvRw or —NRvRw [wherein Rv is hydrogen or (1–4C)alkyl; Rw is hydrogen or (1–4C)alkyl];

and further optional substituents on AR1, AR2, AR2a, AR2b, AR3, AR3a, AR3b, AR4, AR4a, CY1 and CY2 (on an available carbon atom), and also on alkyl groups (unless indicated otherwise) are up to three substituents independently selected from trifluoromethoxy, benzoylamino, benzoyl, phenyl {optionally substituted by up to three substituents independently selected from halo, (1–4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, halo-(1–4C)alkyl, (1–4C)

alkanesulfonamido, —SO₂NRvRw [wherein Rv is hydrogen or (1–4C)alkyl; Rw is hydrogen or (1–4C)alkyl]; and optional substituents on AR2, AR2a, AR2b, AR3, AR3a, AR3b, AR4 and AR4a are (on an available nitrogen atom, where such substitution does not result in quaternization) (1–4C)alkyl, (1–4C)alkanoyl {wherein the (1–4C)alkyl and (1–4C)alkanoyl groups are optionally substituted by (preferably one) substituents independently selected from cyano, hydroxy, nitro, trifluoromethyl, (1–4C)alkyl S(O)$_q$— (q is 0, 1 or 2), (1–4C)alkoxy, (1–4C)alkoxycarbonyl, (1–4C)alkanoylamino, —CONRvRw or —NRvRw [wherein Rv is hydrogen or (1–4C)alkyl; Rw is hydrogen or (1–4C)alkyl]}, (2–4C)alkenyl, (2–4C)alkynyl, (1–4C)alkoxycarbonyl or oxo (to form an N-oxide).

In another aspect is provided a compound of the formula (I), or a pharmaceutically-acceptable salt, or an in-vivo-hydrolysable ester thereof,

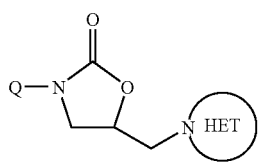

(I)

wherein:
R1 is selected from a substituent from the group
(R1a) wherein R1 is halogen, (1–4C)alkoxy, (2–4C)alkenyloxy, (2–4C)alkenyl, (2–4C)alkynyl, (3–6C)cycloalkyl, (3–6C)cycloalkenyl, amino, (1–4C)alkylamino, di-(1–4C)alkylamino, (2–4C)alkenylamino, (1–4C)alkylcarbonylamino, (1–4C)alkylthiocarbonylamino, (1–4C)alkyl-OCO—NH—, (1–4C)alkyl-NH—CO—NH—, (1–4C)alkyl-NH—CS—NH—, (1–4C)alkyl-SO₂—NH— or (1–4C)alkyl-S(O)$_q$— (wherein q is 0, 1 or 2);
or R1 is selected from the group
(R1b) wherein R1 is a (1–4C)alkyl group which is substituted by one substituent selected from hydroxy, (1–4C)alkoxy, amino, cyano, azido, (2–4C)alkenyloxy, (1–4C)alkylcarbonyl, (1–4C)alkoxycarbonyl, (1–4C)alkylamino, (2–4C)alkenylamino, (1–4C)alkyl-SO₂—NH—(1–4C)alkylcarbonylamino, (1–4C)alkylthiocarbonylamino, (1–4C)alkyl-OCO—NH—, (1–4C)alkyl-NH—CO—NH—, (1–4C)alkyl-NH—CS—NH—, (1–4C)alkyl-SO₂—NH—, (1–4C)alkyl-S(O)$_q$— (wherein q is 0, 1 or 2), (3–6C)cycloalkyl, (3–6C)cycloalkenyl, or an N-linked 5-membered heteroaryl ring, which ring contains either (i) 1 to 3 further nitrogen heteroatoms or (ii) a further heteroatom selected from O and S together with an optional further nitrogen heteroatom; which ring is optionally substituted on a carbon atom by an oxo or thioxo group; and/or the ring is optionally substituted on a carbon atom by 1 or 2 (1–4C)alkyl groups; and/or on an available nitrogen atom (provided that the ring is not thereby quaternised) by (1–4C)alkyl;
or R1 is selected from a group of formula (R1c1) to (R1c3)
(R1c1) a fully saturated 4-membered monocyclic ring containing 1 or 2 heteroatoms independently selected from O, N and S (optionally oxidised), and linked via a ring nitrogen or carbon atom; or
(R1c2) a saturated or unsaturated 5-membered monocyclic ring containing 1 heteroatom selected from O, N and S (optionally oxidised), and linked via a ring nitrogen atom if the ring is not thereby quaternised, or a ring carbon atom; or
(R1c3) a saturated or unsaturated 6- to 8-membered monocyclic ring containing 1 or 2 heteroatoms independently selected from O, N and S (optionally oxidised), and linked via a ring nitrogen atom if the ring is not thereby quaternised, or a ring carbon atom;

wherein said rings in (R1c1) to (R1c3) are optionally substituted on an available carbon atom by 1 or 2 substituents independently selected from hydroxy, (1–4C)alkoxy, amino, cyano, azido, (2–4C)alkenyloxy, (1–4C)alkylcarbonyl, (1–4C)alkoxycarbonyl, (1–4C)alkylamino, (2–4C)alkenylamino, (1–4C)alkyl-SO₂—NH—, (1–4C)alkylcarbonylamino, (1–4C)alkylthiocarbonylamino, (1–4C)alkyl-OCO—NH—, (1–4C)alkyl-NH—CO—NH—, (1–4C)alkyl-NH—CS—NH—, (1–4C)alkyl-SO₂—NH—, (1–4C)alkyl-S(O)$_q$— (wherein q is 0, 1 or 2), (3–6C)cycloalkyl or (3–6C)cycloalkenyl;
or R1 is selected from the group
(R1d) cyano, nitro, azido, formyl, (1–4C)alkylcarbonyl or (1–4C)alkoxycarbonyl; and wherein at each occurrence of an R1 substituent containing an alkyl, alkenyl, alkynyl, cycloalkyl or cycloalkenyl moiety in (R1a), (R1b) or (R1c1) to (R1c3) each such moiety is optionally further substituted on an available carbon atom with one or more substituents independently selected from F and Cl and/or by one cyano group;

$R^2$ and $R^3$ are independently hydrogen or fluoro;

and wherein all other groups, variables and substituents are as hereinbefore defined in the first aspect.

It will be noted that in the groups (Ia) to (If) there is no substituent in the position adjacent to the nitrogen link.

In this specification, where it is stated that a ring may be linked via an sp² carbon atom it is to be understood that the ring is linked via one of the carbon atoms in a C═C double bond.

In this specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C) alkyl includes 1-bromoethyl and 2-bromoethyl.

There follow particular and suitable values for certain substituents and groups which may be referred to in this specification. These values may be used where appropriate with any of the definitions and embodiments disclosed hereinbefore, or hereinafter.

Examples of (1–4C)alkyl and (1–5C)alkyl include methyl, ethyl, propyl, isopropyl and t-butyl; examples of (1–6C)alkyl include methyl, ethyl, propyl, isopropyl, t-butyl, pentyl and hexyl; examples of (1–10C)alkyl include methyl, ethyl, propyl, isopropyl, pentyl, hexyl, heptyl, octyl and nonyl; examples of (1–4C)alkanoylamino-(1–4C)alkyl include formamidomethyl, acetamidomethyl and acetamidoethyl; examples of hydroxy(1–4C)alkyl and hydroxy (1–6C)alkyl include hydroxymethyl, 1-hydroxyethyl, 2-hydroxyethyl and 3-hydroxypropyl; examples of (1–4C) alkoxycarbonyl include methoxycarbonyl, ethoxycarbonyl and propoxycarbonyl; examples of 2-((1–4C)alkoxycarbonyl)ethenyl include 2-(methoxycarbonyl)ethenyl and 2-(ethoxycarbonyl)ethenyl; examples of 2-cyano-2-((1–4C) alkyl)ethenyl include 2-cyano-2-methylethenyl and 2-cyano-2-ethylethenyl; examples of 2-nitro-2-((1–4C)alkyl) ethenyl include 2-nitro-2-methylethenyl and 2-nitro-2-ethylethenyl; examples of 2-((1–4C)alkylaminocarbonyl) ethenyl include 2-(methylaminocarbonyl)ethenyl and 2-(ethylaminocarbonyl)ethenyl; examples of (2–4C)alkenyl include allyl and vinyl; examples of (2–4C)alkynyl include ethynyl and 2-propynyl; examples of (1–4C)alkanoyl include formyl, acetyl and propionyl; examples of (1–4C) alkoxy include methoxy, ethoxy and propoxy; examples of (1–6C)alkoxy and (1–10C)alkoxy include methoxy, ethoxy, propoxy and pentoxy; examples of (1–4C)alkylthio include methylthio and ethylthio; examples of (1–4C)alkylamino include methylamino, ethylamino and propylamino; examples of di-((1–4C)alkyl)amino include dimethylamino, N-ethyl-N-methylamino, diethylamino, N-methyl-N-propylamino and dipropylamino; examples of halo groups include fluoro, chloro and bromo; examples of (1–4C)alkylsulfonyl include methylsulfonyl and ethylsulfonyl; examples of (1–4C)alkoxy-(1–4C)alkoxy and (1–6C)alkoxy-(1–6C) alkoxy include methoxymethoxy, 2-methoxyethoxy, 2-ethoxyethoxy and 3-methoxypropoxy; examples of (1–4C)alkoxy-(1–4C)alkoxy-(1–4C)alkoxy include 2-(methoxymethoxy)ethoxy, 2-(2-methoxyethoxy)ethoxy; 3-(2-methoxyethoxy)propoxy and 2-(2-ethoxyethoxy) ethoxy; examples of (1–4C)alkylS(O)$_2$amino include methylsulfonylamino and ethylsulfonylamino; examples of (1–4C)alkanoylamino and (1–6C)alkanoylamino include formamido, acetamido and propionylamino; examples of (1–4C)alkoxycarbonylamino include methoxycarbonylamino and ethoxycarbonylamino; examples of N-(1–4C) alkyl-N-(1–6C)alkanoylamino include N-methylacetamido, N-ethylacetamido and N-methylpropionamido; examples of (1–4C)alkylS(O)$_p$NH— wherein p is 1 or 2 include methylsulfinylamino, methylsulfonylamino, ethylsulfinylamino and ethylsulfonylamino; examples of (1–4C)alkylS(O)$_p$ ((1–4C)alkyl)N— wherein p is 1 or 2 include methylsulfinylmethylamino, methylsulfonylmethylamino, 2-(ethylsulfinyl)ethylamino and 2-(ethylsulfonyl)ethylamino; examples of fluoro(1–4C)alkylS(O)$_p$NH— wherein p is 1 or 2 include trifluoromethylsulfinylamino and trifluoromethylsulfonylamino; examples of fluoro(1–4C)alkylS(O)$_p$ ((1–4C)alkyl)NH— wherein p is 1 or 2 include trifluoromethylsulfinylmethylamino and trifluoromethylsulfonylmethylamino examples of (1–4C) alkoxy(hydroxy)phosphoryl include methoxy(hydroxy) phosphoryl and ethoxy(hydroxy)phosphoryl; examples of di-(1–4C)alkoxyphosphoryl include di-methoxyphosphoryl, di-ethoxyphosphoryl and ethoxy(methoxy)phosphoryl; examples of (1–4C)alkylS(O)$_q$— wherein q is 0, 1 or 2 include methylthio, ethylthio, methylsulfinyl, ethylsulfinyl, methylsulfonyl and ethylsulfonyl; examples of phenylS(O)$_q$ and naphthylS(O)$_q$— wherein q is 0, 1 or 2 are phenylthio, phenylsulfinyl, phenylsulfonyl and naphthylthio, naphthylsulfinyl and naphthylsulfonyl respectively; examples of benzyloxy-(1–4C)alkyl include benzyloxymethyl and benzyloxyethyl; examples of a (3–4C)alkylene chain are trimethylene or tetramethylene; examples of (1–6C)alkoxy-(1–6C)alkyl include methoxymethyl, ethoxymethyl and 2-methoxyethyl; examples of hydroxy-(2–6C)alkoxy include 2-hydroxyethoxy and 3-hydroxypropoxy; examples of (1–4C)alkylamino-(2–6C)alkoxy include 2-methylaminoethoxy and 2-ethylaminoethoxy; examples of di-(1–4C) alkylamino-(2–6C)alkoxy include 2-dimethylaminoethoxy and 2-diethylaminoethoxy; examples of phenyl(1–4C)alkyl include benzyl and phenethyl; examples of (1–4C)alkylcarbamoyl include methylcarbamoyl and ethylcarbamoyl; examples of di((1–4C)alkyl)carbamoyl include di(methyl) carbamoyl and di(ethyl)carbamoyl; examples of hydroxyimino(1–4C)alkyl include hydroxyiminomethyl, 2-(hydroxyimino)ethyl and 1-(hydroxyimino)ethyl; examples of (1–4C)alkoxyimino include methoxyimino and ehtoxyimino; examples of (1–4C)alkoxyimino-(1–4C)alkyl include methoxyiminomethyl, ethoxyiminomethyl, 1-(methoxyimino)ethyl and 2-(methoxyimino)ethyl; examples of halo(1–4C)alkyl include, halomethyl, 1-haloethyl, 2-haloethyl, and 3-halopropyl; examples of nitro(1–4C)alkyl include nitromethyl, 1-nitroethyl, 2-nitroethyl and 3-nitropropyl; examples of amino(1–4C)alkyl include aminomethyl, 1-aminoethyl, 2-aminoethyl and 3-aminopropyl; examples of cyano(1–4C)alkyl include cyanomethyl, 1-cyanoethyl, 2-cyanoethyl and 3-cyanopropyl; examples of (1–4C)alkanesulfonamido include methanesulfonamido and ethanesulfonamido; examples of (1–4C)alkylaminosulfonyl include methylaminosulfonyl and ethylaminosulfonyl; and examples of di-(1–4C)alkylaminosulfonyl include dimethylaminosulfonyl, diethylaminosulfonyl and N-methyl-N-ethylaminosulfonyl; examples of (1–4C)alkanesulfonyloxy include methylsulfonyloxy, ethylsulfonyloxy and propylsulfonyloxy; examples of (1–4C)alkanoyloxy include acetoxy; examples of (1–4C)alkylaminocarbonyl include methylaminocarbonyl and ethylaminocarbonyl; examples of di((1–4C) alkyl)aminocarbonyl include dimethylaminocarbonyl and diethylaminocarbonyl; examples of (3–8C)cycloalkyl include cyclopropyl, cyclobutyl, cyclopentyl and cyclohexyl; examples of (4–7C)cycloalkyl include cyclobutyl, cyclopentyl and cyclohexyl; examples of di(N-(1–4C)alkyl) aminomethylimino include dimethylaminomethylimino and diethylaminomethylimino.

Particular values for AR2 include, for example, for those AR2 containing one heteroatom, furan, pyrrole, thiophene; for those AR2 containing one to four N atoms, pyrazole, imidazole, pyridine, pyrimidine, pyrazine, pyridazine, 1,2,3- & 1,2,4-triazole and tetrazole; for those AR2 containing one N and one O atom, oxazole, isoxazole and oxazine; for those AR2 containing one N and one S atom, thiazole and isothiazole; for those AR2 containing two N atoms and one S atom, 1,2,4- and 1,3,4-thiadiazole.

Particular examples of AR2a include, for example, dihydropyrrole (especially 2,5-dihydropyrrol-4-yl) and tetrahydropyridine (especially 1,2,5,6-tetrahydropyrid-4-yl).

Particular examples of AR2b include, for example, tetrahydrofuran, pyrrolidine, morpholine (preferably morpholino), thiomorpholine (preferably thiomorpholino), piperazine (preferably piperazino), imidazoline and piperidine, 1,3-dioxolan-4-yl, 1,3-dioxan-4-yl, 1,3-dioxan-5-yl and 1,4-dioxan-2-yl.

Particular values for AR3 include, for example, bicyclic benzo-fused systems containing a 5- or 6-membered heteroaryl ring containing one nitrogen atom and optionally 1–3 further heteroatoms chosen from oxygen, sulfur and nitrogen. Specific examples of such ring systems include, for example, indole, benzofuran, benzothiophene, benzimidazole, benzothiazole, benzisothiazole, benzoxazole, benzisoxazole, quinoline, quinoxaline, quinazoline, phthalazine and cinnoline.

Other particular examples of AR3 include 5/5-, 5/6 and 6/6 bicyclic ring systems containing heteroatoms in both of the rings. Specific examples of such ring systems include, for example, purine and naphthyridine.

Further particular examples of AR3 include bicyclic heteroaryl ring systems with at east one bridgehead nitrogen and optionally a further 1–3 heteroatoms chosen from oxygen, sulfur and nitrogen. Specific examples of such ring systems include, for example, 3H-pyrrolo[1,2-a]pyrrole, pyrrolo[2,1-b]thiazole, 1H-imidazo[1,2-a]pyrrole, 1H-imidazo[1,2-a]imidazole, 1H,3H-pyrrolo[1,2-c]oxazole, 1H-imidazo[1,5-a]pyrrole, pyrrolo[1,2-b]isoxazole, imidazo[5,1-b]thiazole, imidazo[2,1-b]thiazole, indolizine, imidazo[1,2-a]pyridine, imidazo[1,5-a]pyridine, pyrazolo[1,5-a]pyridine, pyrrolo[1,2-b]pyridazine, pyrrolo[1,2-c]pyrimidine, pyrrolo[1,2-a]pyrazine, pyrrolo[1,2-a]pyrimidine, pyrido[2,1-c]-s-triazole, s-triazolo[1,5-a]pyridine, imidazo[1,2-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole. Other specific examples of such ring systems include, for example, [1H]-pyrrolo[2,1-c]oxazine, [3H]-oxazolo[3,4-a]pyridine, [6H]-pyrrolo[2,1-c]oxazine and pyrido[2,1-c][1,4]oxazine. Other specific examples of 5/5-bicyclic ring systems are imidazooxazole or imidazothiazole, in particular imidazo[5,1-b]thiazole, imidazo[2,1-b]thiazole, imidazo[5,1-b]oxazole or imidazo[2,1-b]oxazole.

Particular examples of AR3a and AR3b include, for example, indoline, 1,3,4,6,9,9a-hexahydropyrido[2,1c][1,4]oxazin-8-yl, 1,2,3,5,8,8a-hexahydroimidazo[1,5a]pyridin-7-yl, 1,5,8,8a-tetrahydrooxazolo[3,4a]pyridin-7-yl, 1,5,6,7,8,8a-hexahydrooxazolo[3,4a]pyridin-7-yl, (7aS)[3H,5H]-1,7a-dihydropyrrolo[1,2c]oxazol-6-yl, (7aS)[5H]-1,2,3,7a-tetrahydropyrrolo[1,2c]imidazol-6-yl, (7aR)[3H,5H]-1,7a-dihydropyrrolo[1,2c]oxazol-6-yl, [3H,5H]-pyrrolo[1,2-c]oxazol-6-yl, [5H]-2,3-dihydropyrrolo[1,2-c]imidazol-6-yl, [3H,5H]-pyrrolo[1,2-c]thiazol-6-yl, [3H,5H]-1,7a-dihydropyrrolo[1,2-c]thiazol-6-yl, [5H]-pyrrolo[1,2-c]imidazol-6-yl, [1H]-3,4,8,8a-tetrahydropyrrolo[2,1-c]oxazin-7-yl, [3H]-1,5,8,8a-tetrahydrooxazolo[3,4-a]pyrid-7-yl, [3H]-5,8-dihydroxazolo[3,4-a]pyrid-7-yl and 5,8-dihydroimidazo[1,5-a]pyrid-7-yl.

Particular values for AR4 include, for example, pyrrolo[a]quinoline, 2,3-pyrroloisoquinoline, pyrrolo[a]isoquinoline, 1H-pyrrolo[1,2-a]benzimidazole, 9H-imidazo[1,2-a]indole, 5H-imidazo[2,1-a]isoindole, 1H-imidazo[3,4-a]indole, imidazo[1,2-a]quinoline, imidazo[2,1-a]isoquinoline, imidazo[1,5-a]quinoline and imidazo[5,1-a]isoquinoline.

The nomenclature used is that found in, for example, "Heterocyclic Compounds (Systems with bridgehead nitrogen), W. L. Mosby (Interscience Publishers Inc., New York), 1961, Parts 1 and 2.

Where optional substituents are listed such substitution is preferably not geminal disubstitution unless stated otherwise. If not stated elsewhere, suitable optional substituents for a particular group are those as stated for similar groups herein.

Preferable optional substituents on Ar2b as 1,3-dioxolan-4-yl, 1,3-dioxan-4-yl, 1,3-dioxan-5-yl or 1,4-dioxan-2-yl are mono- or disubstitution by substituents independently selected from (1–4C)alkyl (including geminal disubstitution), (1–4C)alkoxy, (1–4C)alkylthio, acetamido, (1–4C)alkanoyl, cyano, trifluoromethyl and phenyl].

Preferable optional substituents on CY1 & CY2 are mono- or disubstitution by substituents independently selected from (1–4C)alkyl (including geminal disubstitution), hydroxy, (1–4C)alkoxy, (1–4C)alkylthio, acetamido, (1–4C)alkanoyl, cyano, and trifluoromethyl.

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (I) or a pharmaceutically-acceptable salt thereof.

Various forms of prodrugs are known in the art, for examples see:

a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

An in-vivo hydrolysable ester of a compound of the invention or a pharmaceutically-acceptable salt thereof containing a carboxy or hydroxy group is, for example, a pharmaceutically-acceptable ester which is hydrolysed in the human or animal body to produce the parent alcohol.

Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C)cycloalkoxycarbonyloxy(1–6C)alkyl esters for example 1-cyclohexylcarbonyloxyethyl; 1,3-dioxolan-2-onylmethyl esters for example 5-methyl-1,3-dioxolan-2-ylmethyl; and (1–6C)alkoxycarbonyloxyethyl esters for example 1-methoxycarbonyloxyethyl and may be formed at any carboxy group in the compounds of this invention.

Suitable pro-drugs for pyridine derivatives include acyloxymethyl pyridinium salts eg halides; for example a pro-drug such as:

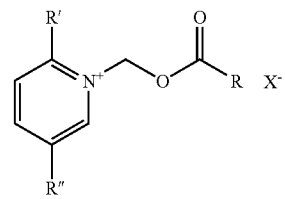

An in-vivo hydrolysable ester of a compound of the invention or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1–10C)alkanoyl, benzoyl, phenylacetyl and substituted benzoyl and phenylacetyl, (1–10C)alkoxycarbonyl (to give alkyl carbonate esters), di-(1–4C)alkylcarbamoyl and N-(di-(1–4C)alkylaminoethyl)-N-(1–4C)alkylcarbamoyl (to give carbamates), di-(1–4C)alkylaminoacetyl, carboxy (2–5C)alkylcarbonyl and carboxyacetyl. Examples of ring substituents on phenylacetyl and benzoyl include chloromethyl or aminomethyl, (1–4C)alkylaminomethyl and di-((1–4C)alkyl)aminomethyl, and morpholino or piperazino linked from a ring nitrogen atom via a methylene linking group to the 3- or 4-position of the benzoyl ring. Other interesting in-vivo hydrolysable esters include, for example, $R^4C(O)O(1–6C)alkyl-CO—$ (wherein $R^4$ is for example, optionally substituted benzyloxy-(1–4C)alkyl, or optionally substituted phenyl; suitable substituents on a phenyl group in such esters include, for example, 4-(1–4C)piperazino-(1–4C)alkyl, piperazino-(1–4C)alkyl and morpholino-(1–4C)alkyl.

Suitable in-vivo hydrolysable esters of a compound of the formula (I) are described as follows. For example, a 1,2-diol may be cyclised to form a cyclic ester of formula (PD1) or a pyrophosphate of formula (PD2), and a 1,3-diol may be cyclised to form a cyclic ester of the formula (PD3):

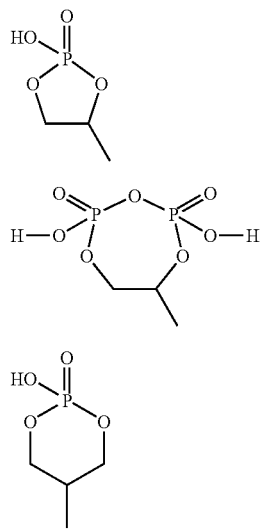

(PD1)

(PD2)

(PD3)

Esters of compounds of formula (I) wherein the HO— function/s in (PD1), (PD2) and (PD3) are protected by (1–4C)alkyl, phenyl or benzyl are useful intermediates for the preparation of such pro-drugs.

Further in-vivo hydrolysable esters include phosphoramidic esters, and also compounds of invention in which any free hydroxy group independently forms a phosphoryl (npd is 1) or phosphiryl (npd is 0) ester of the formula (PD4):

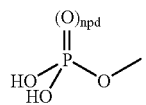

(PD4)

For the avoidance of doubt, phosphono is $—P(O)(OH)_2$; (1–4C)alkoxy(hydroxy)-phosphoryl is a mono-(1–4C) alkoxy derivative of $—O—P(O)(OH)_2$; and di-(1–4C) alkoxyphosphoryl is a di-(1–4C)alkoxy derivative of $—O—P(O)(OH)_2$.

Useful intermediates for the preparation of such esters include compounds containing a group/s of formula (PD4) in which either or both of the —OH groups in (PD1) is independently protected by (1–4C)alkyl (such compounds also being interesting compounds in their own right), phenyl or phenyl-(1–4C)alkyl (such phenyl groups being optionally substituted by 1 or 2 groups independently selected from (1–4C)alkyl, nitro, halo and (1–4C)alkoxy).

Thus, prodrugs containing groups such as (PD1), (PD2), (PD3) and (PD4) may be prepared by reaction of a compound of invention containing suitable hydroxy group/s with a suitably protected phosphorylating agent (for example, containing a chloro or dialkylamino leaving group), followed by oxidation (if necessary) and deprotection.

Other suitable prodrugs include phosphonooxymethyl ethers and their salts, for example a prodrug of R—OH such as:

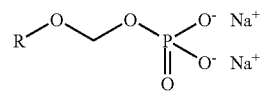

When a compound of invention contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Where pharmaceutically-acceptable salts of an in-vivo hydrolysable ester may be formed this is achieved by conventional techniques. Thus, for example, compounds containing a group of formula (PD1), (PD2), (PD3) and/or (PD4) may ionise (partially or fully) to form salts with an appropriate number of counter-ions. Thus, by way of example, if an in-vivo hydrolysable ester prodrug of a compound of invention contains two (PD4) groups, there are four HO—P— functionalities present in the overall molecule, each of which may form an appropriate salt (i.e. the overall molecule may form, for example, a mono-, di-, tri- or tetra-sodium salt).

The compounds of the present invention have a chiral centre at the C-5 position of the oxazolidinone ring. The pharmaceutically active enantiomer is of the formula (IA):

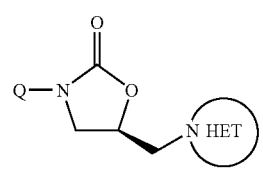

(IA)

The present invention includes the pure enantiomer depicted above or mixtures of the 5R and 5S enantiomers, for example a racemic mixture. If a mixture of enantiomers is used, a larger amount (depending upon the ratio of the enantiomers) will be required to achieve the same effect as the same weight of the pharmaceutically active enantiomer. The enantiomer depicted above may be the 5(R) or 5(S)

enantiomer depending on the nature of the N-HET group (for example, when —N-HET is imidazole it is the 5(S) enantiomer).

Furthermore, some compounds of the formula (I) may have other chiral centres, for example, certain sulfoxide compounds may be chiral at the sulfur atom. It is to be understood that the invention encompasses all such optical and diastereo-isomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

Furthermore, some compounds of the formula (I), for example certain sulfoxide compounds may exist as cis- and trans-isomers. It is to be understood that the invention encompasses all such isomers, and mixtures thereof, that possess antibacterial activity.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

It is also to be understood that certain compounds of the formula (I) may exhibit polymorphism, and that the invention encompasses all such forms which possess antibacterial activity.

As stated before, we have discovered a range of compounds that have good activity against a broad range of Gram-positive pathogens, including organisms known to be resistant to most commonly used antibiotics, and to certain fastidious Gram negative strains such as *H. influenzae* and *M. catarrhalis*. They have good physical and/or pharmacokinetic properties in general, and favourable toxicological and MAO profiles.

Particularly preferred compounds of the invention comprise a compound of formula (I), or a pharmaceutically-acceptable salt or an in-vivo hydrolysable ester thereof, wherein the substituents Q, HET (which may also be described as —N-HET herein), T and other substituents mentioned above have values disclosed hereinbefore, or any of the following values (which may be used where appropriate with any of the definitions and embodiments disclosed hereinbefore or hereinafter):

In one embodiment of the invention are provided compounds of formula (I), in an alternative embodiment are provided pharmaceutically-acceptable salts of compounds of formula (I), in a further alternative embodiment are provided in-vivo hydrolysable esters of compounds of formula (I), and in a further alternative embodiment are provided pharmaceutically-acceptable salts of in-vivo hydrolysable esters of compounds of formula (I).

In another embodiment of the invention are provided compounds of formula (I), or a pharmaceutically-acceptable salt or an in-vivo hydrolysable ester thereof, in which Q, HET (which may also be described as —N-HET herein) and other substituents mentioned above have the values disclosed hereinbefore, and T is as defined hereinbefore and hereinafter for (TA), (TB) and (TD) (i.e. in this embodiment T is not (TC) or (TE)).

In another embodiment of the invention are provided compounds of formula (I), or a pharmaceutically-acceptable salt or an in-vivo hydrolysable ester thereof, in which Q, HET (which may also be described as —N-HET herein) and other substituents mentioned above have the values disclosed hereinbefore, and T is as defined hereinbefore and hereinafter for (TC), particularly TC4.

In another embodiment of the invention are provided compounds of formula (I), or a pharmaceutically-acceptable salt or an in-vivo hydrolysable ester thereof, in which Q, HET (which may also be described as —N-HET herein) and other substituents mentioned above have the values disclosed hereinbefore, and T is as defined hereinbefore and hereinafter for (TA).

In another embodiment of the invention are provided compounds of formula (I), or a pharmaceutically-acceptable salt or an in-vivo hydrolysable ester thereof, in which Q, HET (which may also be described as —N-HET herein) and other substituents mentioned above have the values disclosed hereinbefore, and T is as defined hereinbefore and hereinafter for (TA) and (TC).

In a further embodiment of the invention are provided compounds of formula (I), or a pharmaceutically-acceptable salt or an in-vivo hydrolysable ester thereof, in which Q, HET (which may also be described as —N-HET herein), T and other substituents mentioned above have the values disclosed hereinbefore and R1 is selected from the group (R1b).

Preferably Q is selected from Q1, Q2, Q4 and Q6; especially Q1 and Q2; and most preferably Q is Q1.

In one embodiment R1 has values (R1a) to (R1c1).

Preferable R1 groups are those of (R1a) and (R1b).

In (R1b) the substituted (1–4C)alkyl group is preferably a substituted methyl group.

Preferable (R1) groups provided by optional F and/or Cl and/or one cyano further substituents in (R1a) and (R1b) are, for example, R1 as trifluoromethyl, —CHF$_2$, —CH$_2$F, —CH$_2$CN, —CF$_2$NH(1–4C)alkyl, —CF$_2$CH$_2$OH, —CH$_2$OCF$_3$, —CH$_2$OCHF$_2$, —CH$_2$OCH$_2$F, —NHCF$_2$CH$_3$.

In one aspect R1 is preferably selected from a substituent from the groups R1a, R1b and R1 d wherein:

(R1a) halogen, hydroxy, (1–4C)alkoxy, (2–4C)alkenyloxy, (2–4C)alkenyl, (2–4C)alkynyl (optionally substituted on the terminal carbon by CH$_2$=CH—, di(1–4C)alkylamino, AR2, AR2a or AR2b), (3–6C)cycloalkyl, (3–6C)cycloalkenyl, (1–4C)alkyl-S(O)q- (wherein q is 0), amino, (1–4C)alkylcarbonylamino, (1–4C)alkylamino, di-(i-4C)alkylamino and (2–4C)alkenylamino;

(R1b) a (1–4C)alkyl group which is substituted by one substituent selected from hydroxy, halo, (1–4C)alkoxy, amino, (1–4C)alkylamino, di-(1–4C)alkylamino, (1–4C)alkyl-S(O)q- (wherein q is 0, 1 or 2), cyano and azido, (3–6C)cycloalkyl, AR1-S(O)q- (wherein q is 0, 1 or 2 and AR1 is defined hereinbelow), AR2-S(O)q- (wherein q is 0, 1 or 2), AR2a-S(O)q- (wherein q is 0, 1 or 2), benzyl-S(O)q- (wherein q is 0, 1 or 2), (1–4C)alkyl-OCO—NH—, (1–4C)alkyl-NHCO—O—, (1–4C)alkylaminocarbonyl, di(1–4C)alkylaminocarbonyl and H$_2$NC(=NH)S—;

(R1d) cyano, nitro, azido, formyl, (1–4C)alkylcarbonyl, (1–4C)alkoxycarbonyl, H$_2$NC(O)—, ((1–4C)alkyl)NHC(O)—;

and wherein at each occurrence of an R1 substituent containing an alkyl, alkenyl, alkynyl, cycloalkyl or cycloalkenyl moiety in (R1a) or (R1b) each such moiety is optionally further substituted on an available carbon atom with one, two, three or more substituents independently selected from F, Cl, Br, OH and CN.

In another aspect R1 is preferably selected from a substituent from the groups R1a, R1b and R1d, wherein:

(R1a) halogen, hydroxy, (1–4C)alkoxy, (2–4C)alkenyl, (2–4C)alkynyl, -ethynyl-ethene, -ethynyl-AR2, -ethynyl-AR2a, -but-2-ynyl-4-AR2a, -but-2-ynyl-4-AR2b, -but-2-ynyl-4-di(1–4C)alkylamino, (3–6C)cycloalkyl, (1–4C)alkyl-S(O)q- (wherein q is 0), (1–4C)alkylcarbonylamino and amino, (R1b) a (1–4C)alkyl group which is substituted by one substituent selected from hydroxy, halo, (1–4C)alkoxy, amino, di(1–4C)alkylamino, cyano, azido, (1–4C)alkyl-S(O)q- (wherein q is 0, 1 or 2), AR2-S(O)q- (wherein q is 0), benzyl-S(O)q- (wherein q is 0), (1–4C)alkyl-OCO—NH—, (1–4C)alkyl-NHCO—O—, di(1–4C)alkylaminocarbonyl and $H_2NC(=NH)S—$;

(R1d) cyano, nitro, formyl, (1–4C)alkoxycarbonyl and $H_2NC(O)—$;

and wherein at each occurrence of an R1 substituent containing an alkyl, alkenyl, alkynyl, cycloalkyl or cycloalkenyl moiety in (R1a) or (R1b) each such moiety is optionally further substituted on an available carbon atom with one, two or three substituents independently selected from F, Cl, Br, OH and CN.

When R1a is ethynyl-AR2, conveniently AR2 is a 5-membered ring, particularly AR2 is oxazolyl, isoxazolyl, thiazolyl or thiadiazolyl.

When R1a is -ethynyl-AR2a or -but-2-ynyl-4-AR2a, conveniently AR2a is a 5 membered ring, particularly AR2a as 3-pyrroline, 2H-pyrrole or pyrazoline.

When R1a is -but-2-ynyl-4-AR2b, conveniently AR2b a 6-membered ring such as morpholine.

In a further aspect R1 is most preferably
(a) hydrogen; or
(b) halogen, in particular fluorine, chlorine, or bromine; or
(c) cyano; or
(d) monosubstituted (1–4C)alkyl, in particular fluoromethyl, choromethyl, bromomethyl, cyanomethyl, azidomethyl, hydroxymethyl; or
(e) disubstituted (1–4C)alkyl, for example difluoromethyl, or
(f) trisubstituted (1–4C)alkyl, for example trifluoromethyl; or
(g) ethynyl or substituted ethynyl; or
(h) nitro In (TAb), preferred are (TAb1) to (TAb5), and especially (TAb2), (TAb3) and/or (TAb5), most especially (TAb2) and (TAb5). The above preferred values of (TAb) are particularly preferred when present in Q1 or Q2, especially Q1.

In (TAb) it is to be understood that when a value for $—X^1—$ is a two-atom link and is written, for example, as $—CH_2NH—$ it is the left hand part ($—CH_2—$ here) which is bonded to the group of formula (TAb1) to (TAb6) and the right hand part (—NH— here) which is bonded to —Y— in the definition in (TAbc). Similarly, when $—Y^1—$ is a two-atom link and is written, for example, as —CONH— it is the left hand part of $—Y^1—$ (—CO— here) which is bonded to the right hand part of $—X^1—$, and the right hand part of $—Y^1—$ (—NH— here) which is bonded to the AR2, AR2a, AR2b, AR3, AR3a or AR3b moiety in the definition in (TAbc).

In one embodiment, in (TAb) preferably $R^6$ is hydrogen or (1–4C)alkyl, and $R^4$ and $R^5$ are independently selected from hydrogen, cyano, formyl, bromo, hydroxymethyl, thiomethyl, (1–4C)alkyl (particularly methyl) and hydroxyimino or one of $R^4$ and $R^5$ is selected from group (TAba1). Most preferable is (TAb2) and/or (TAb5) with such preferable substituents.

In another embodiment in (TAb) preferably $R^6$ is hydrogen or (1–4C)alkyl, and $R^4$ and $R^5$ are independently selected from hydrogen, cyano, formyl, bromo, hydroxymethyl, (1–4C)alkyl or one of $R^4$ and $R^5$ is selected from group (TAba1). Most preferable is (TAb2) and/or (TAb5) with such preferable substituents.

In another embodiment, in (TAb) preferably $R^6$ is hydrogen or (1–4C)alkyl, and $R^4$ and $R^5$ are independently selected from hydrogen, cyano, formyl, bromo, hydroxymethyl, thiomethyl, (1–4C)alkyl (particularly methyl) and hydroxyimino. Most preferable is (TAb2) and/or (TAb5) with such preferable substituents.

In another embodiment, in (TAb), $R^6$ is hydrogen and $R^4$ and $R^5$ are independently selected from hydrogen and methyl.

In (TC), for the avoidance of doubt, $(\ )_{m1}$, $(\ )_{n1}$ and $(\ )_{o1}$ indicate $(—CH_2—)_{m1}$, $(—CH_2—)_{n1}$ and $(—CH_2—)_{o1}$ respectively (optionally substituted as described above).

In the definition of (TC1) to (TC4), in an alternative embodiment $>A_3-B_3—$ is not $>N—CH_2—$ in (TC1) to (TC3).

In the above definition of (TC1) to (TC4) and of the further optional substituents:

(i) ARc is preferably AR2, and in one embodiment the further optional substituents are preferably not selected from the values listed for Rc.

(ii) A preferred value for G is $>N(Rc)$ or $>C(R^{11})(R12)$. Also preferred is G as O or S, particularly in (TC4) when Rp is hydrogen.

(iii) Preferred is (TC4) as piperazinyl, morpholino or thiomorpholino or as tetrahydropyridin-4-yl.

(iv) $>A_3-B_3—$ is preferably $>C(Rq)-CH(Rr)-$ in (TC1) to (TC3).

Particularly preferred values for the optional substituents and groups defined in (TC) are rings of formula (TC5) to (TC11), particularly when present in Q1 or Q2, especially Q1:

(TC5)

(TC6)

(TC7)

(TC8)

(TC9)

-continued (TC10)

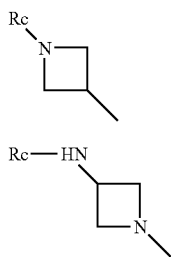

(TC11)

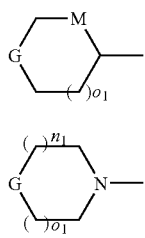

wherein Rc has any of the values listed hereinbefore or hereinafter.

Especially preferred are (TC5), (TC6), (TC7) and (TC9), most especially (TC5) in which Rc has any of the values listed hereinbefore or hereinafter (especially $R^{13}CO$— with the preferable $R^{13}$ values given hereinafter). In (TC5) Rc is preferably selected from the group (Rc2), especially $R^{13}CO$— with the preferable $R^{13}$ values given hereinafter. In (TC7) Rc is preferably selected from group (Rc3) or (Rc4).

For (TC), further preferred values for the optional substituents and groups defined in (TC) are rings of formula (TC12) and (TC13), particularly when present in Q1 or Q2, especially Q1:

(TC12)

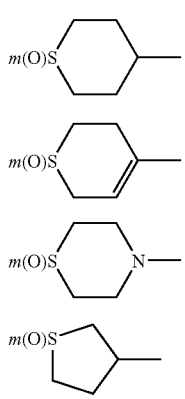

(TC13)

wherein G is —O—, —S—, —SO—, —$SO_2$— or >N(Rc) and Rc, o1 and n1 have any of the values defined herein.

Preferably (TC12) is (TC12a), (TC12b), (TC12c) or (TC12d) and preferably (TC13) is (TC13a), particularly when present in Q1 or Q2, especially Q1:

(TC12a)

(TC12b)

(TC12c)

-continued (TC12d)

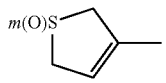

wherein m is 0, 1 or 2.

In (TDa), particularly preferred values are when present in Q1 or Q2, especially Q1.

In (TDb) it will be appreciated that unstable anti-Bredt compounds are not contemplated in this definition (i.e. compounds with stuctures (TDb3), (TDb4), (TDb7), (TDb8), (TDb9), (TDb12), (TDb13) and (TDb14) in which an $sp^2$ carbon atom is directed towards a bridgehead position).

In (TDb), particularly preferred values of (TDb) are the following structures of formula (TDb4), (TDb8) and/or (TDb9); wherein Rc has any of the values listed hereinbefore or hereinafter. The values of (TDb) are particularly preferred when present in Q1 or Q2, especially Q1.

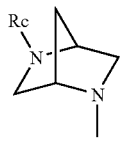

(TDb4a & b)

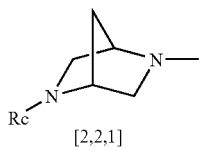
[2,2,1]

(TDb8)

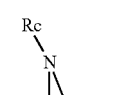
[3,2,1]

(TDb9)

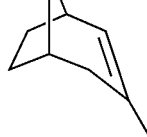
[2,2,2]

In (TE1) to (TE3), preferred values for the groups defined in (TE) are defined by formulae (TE1a, b), (TE2a) and (TE3a), particularly when present in Q1 or Q2, especially Q1:

(TE1a)

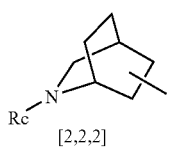

(TE1b)

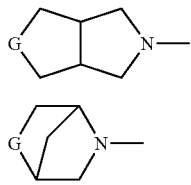

-continued

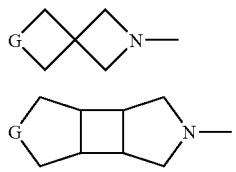

(TE2a)

(TE3a)

wherein G is —O—, —S—, —SO— or —SO$_2$—.

Preferably (T) is (TC12a), (TC12b) or (TAb2) particularly when present in Q1 or Q2, especially Q1.

Preferable values for other substituents (which may be used where appropriate with any of the definitions and embodiments disclosed hereinbefore or hereinafter) are:

(a) —N-HET is preferably of formula (Ic), (Id) or (If).
(b) In one aspect preferably one of $R^2$ and $R^3$ is hydrogen and the other fluoro. In another aspect both $R^2$ and $R^3$ are fluoro.
(c) In another aspect one of $R^2$ and $R^3$ is hydrogen or fluoro and the other is selected from Cl, CF$_3$, Me, Et, OMe and SMe.
(d) In (TC4) preferably >A$_3$-B$_3$— is >C=CH— or >N—CH$_2$—.
(e) Preferably Rc is $R^{13}$CO— and preferably $R^{13}$ is (1–4C)alkoxycarbonyl, hydroxy(1–4C)alkyl, (1–4C)alkyl (optionally substituted by one or two hydroxy groups, or by an (1–4C)alkanoyl group), (1–4C)alkylamino, dimethylamino(1–4C)alkyl, (1–4C)alkoxymethyl, (1–4C)alkanoylmethyl, (1–4C)alkanoyloxy(1–4C)alkyl, (1–5C)alkoxy or 2-cyanoethyl.
(f) More preferably $R^{13}$ is 1,2-dihydroxyethyl, 1,3-dihydroxyprop-2-yl, 1,2,3-trihydroxyprop-1-yl, methoxycarbonyl, hydroxymethyl, methyl, methylamino, dimethylaminomethyl, methoxymethyl, acetoxymethyl, methoxy, methylthio, naphthyl, tert-butoxy or 2-cyanoethyl.
(g) Particularly preferred as $R^{13}$ is 1,2-dihydroxyethyl, 1,3-dihydroxyprop-2-yl or 1,2,3-trihydroxyprop-1-yl.
(h) In another aspect preferably $R^{13}$ is (1–10C)alkyl [optionally substituted by one or more hydroxy] or $R^{14}$C(O)O(1–6C)alkyl.

For compounds of formula (I) preferred values for Rc are those in group (Rc2) when present in any of the definitions herein containing Rc—for example when present in compounds in which there is a (TC5) or (TC9) ring system.

In the definition of (Rc2c) the AR2a, AR2b, AR3a and AR3b versions of AR2 and AR3 containing groups are preferably excluded.

Where the number of optional substituents on a group is not otherwise preferably defined, the preferable number of optional substituents is one.

Particularly preferred compounds of the present invention are of the formula (IB):

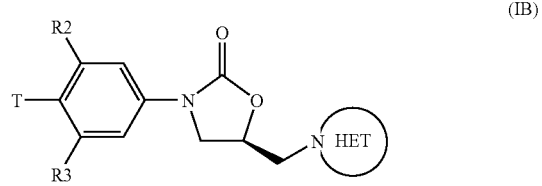

(IB)

wherein —N-HET is 1,2,3-triazol-1-yl or tetrazol-2-yl;

R1 is selected from (R1a) or (R1b);
$R^2$ and $R^3$ are independently hydrogen or fluoro; and
T is selected from (TAb1 to 6), (TC5), (TC7), (TC9), (TC12), (TC13) and (TE1) to (TE3); or in-vivo hydrolysable esters or pharmaceutically-acceptable salts thereof.

Further particularly preferred compounds of the present invention are of the formula (IB) defined above, wherein —N-HET is 1,2,3-triazol-1-yl or tetrazol-2-yl;
R1 is selected from (R1d);
$R^2$ and $R^3$ are independently hydrogen or fluoro; and
T is selected from (TAb1 to 6), (TC5), (TC7), (TC9), (TC12), (TC13) and (TE1) to (TE3); or in-vivo hydrolysable esters or pharmaceutically-acceptable salts thereof.

Further particularly preferred compounds of the present invention are of the formula (IB) defined above, wherein —N-HET is 1,2,3-triazol-1-yl or tetrazol-2-yl;
R1 is selected from (R1a), (R1b) and (R1d);
$R^2$ and $R^3$ are independently hydrogen or fluoro; and
T is selected from (TAb1 to 6), (TC12a) and (TC12b); or in-vivo hydrolysable esters or pharmaceutically-acceptable salts thereof.

Further particularly preferred compounds of the present invention are of the formula (IB) defined above, wherein —N-HET is 1,2,3-triazol-1-yl or tetrazol-2-yl;
R1 is selected from (R1a), (R1b) and (R1d);
$R^2$ and $R^3$ are independently hydrogen or fluoro; and
T is selected from (TAb2), (TAb3), (TAb5), (TAb6), (TC5), (TC12a), (TC12b), (TC12d) and (TC13a); or in-vivo hydrolysable esters or pharmaceutically-acceptable salts thereof.

Further particularly preferred compounds of the present invention are of the formula (EB) defined above, wherein —N-HET is 1,2,3-triazol-1-yl or tetrazol-2-yl;
R1 is selected from (R1a), (R1b) and (R1d);
$R^2$ and $R^3$ are independently hydrogen or fluoro; and
T is selected from (TAb2), (TC12a) and (TC12b); or in-vivo hydrolysable esters or pharmaceutically-acceptable salts thereof.

Further particularly preferred compounds of the present invention are of the formula (IB) defined above wherein R1 is a methyl group from (R1b), substituted with any of those substituents defined herein in (R1b), or in-vivo hydrolysable esters or pharmaceutically-acceptable salts thereof.

Further especially preferred compounds of the invention are of the formula (IB) defined above wherein T is selected from (TAb2 & 5), (TC5), (TC9), (TC12a to d), (TC13a), (TE1a & b), (TE2a) and (TE3a); or in-vivo hydrolysable esters or pharmaceutically-acceptable salts thereof.

In the above aspects and preferred compounds of formula (IB), in (TC5), (TC7), (TC9), preferably Rc is as defined in (Rc2) and especially $R^{13}$CO— wherein $R^{13}$ is preferably (1–4C)alkoxycarbonyl, hydroxy(1–4C)alkyl, (1–4C)alkyl (optionally substituted by one or two hydroxy groups, or by an (1–4C)alkanoyl group), (1–4C)alkylamino, dimethylamino(1–4C)alkyl, (1–4C)alkoxymethyl, (1–4C)alkanoylmethyl, (1–4C)alkanoyloxy(1–4C)alkyl, (1–5C)alkoxy or 2-cyanoethyl.

In all of the above aspects and preferred compounds of formula (IB), in-vivo hydrolysable esters are preferred where appropriate, especially phosphoryl esters (as defined by formula (PD4) with npd as 1).

In all of the above definitions the preferred compounds are as shown in formula (IA), i.e. the pharmaceutically active enantiomer.

Process Section:

In a further aspect the present invention provides a process for preparing a compound of formula (I) or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A compound of the formula (I), or a pharmaceutically-acceptable salt or an in vivo hydrolysable ester thereof, may be prepared by any process known to be applicable to the preparation of chemically-related compounds. Such processes, when used to prepare a compound of the formula (I), or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples (in which, for example, 3,5-difluorophenyl, 3-fluorophenyl and (des-fluoro)phenyl containing intermediates may all be prepared by analagous procedures; or by alternative procedures—for example, the preparation of (T group)-(fluoro) phenyl intermediates by reaction of a (fluoro)phenylstannane with, for example, a pyran or (tetrahydro)pyridine compound, may also be prepared by anion chemistry (see, for example, WO97/30995). Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the following Patent and Application Publications, the contents of the relevant process sections of which are hereby incorporated herein by reference:

WO99/02525; WO98/54161; WO97/37980; WO97/30981 (& U.S. Pat. No. 5,736,545); WO97/21708 (& U.S. Pat. No. 5,719,154); WO97/10223; WO97/09328; WO96/35691; WO96/23788; WO96/15130; WO96/13502; WO95/25106 (& U.S. Pat. No. 5,668,286); WO95/14684 (& U.S. Pat. No. 5,652,238); WO95/07271 (& U.S. Pat. No. 5,688,792); WO94/13649; WO94/01 110; WO93/23384 (& U.S. Pat. No. 5,547,950 & U.S. Pat. No. 5,700,799); WO93/09103 (& U.S. Pat. No. 5,565,571, U.S. Pat. No. 5,654,428, U.S. Pat. No. 5,654,435, U.S. Pat. No. 5,756,732 & U.S. Pat. No. 5,801,246); U.S. Pat. No. 5,231,188; U.S. Pat. No. 5,247,090; U.S. Pat. No. 5,523,403; WO97/27188; WO97/30995; WO97/31917; WO98/01447; WO98/01446; WO99/10342; WO99/10343; WO99/11642; WO99/64416; WO99/64417; WO00/21960; WO 01/40222; WO01/81350 and WO01/98297; European Patent Application Nos. 0,359,418 and 0,609,905; 0,693,491 A1 (& U.S. Pat. No. 5,698,574); 0,694,543 A1 (& AU 24985/95); 0,694,544 A1 (& CA 2,154,024); 0,697,412 A1 (& U.S. Pat. No. 5,529,998); 0,738,726 A1 (& AU 50735/96); 0,785,201 A1 (& AU 10123/97); German Patent Application Nos. DE 195 14 313 A1 (& U.S. Pat. No. 5,529,998); DE 196 01 264 A1 (& AU 10098/97); DE 196 01 265 A1 (& AU 10097/97); DE 196 04 223 A1 (& AU 12516/97); DE 196 49 095 A1 (& AU 12517/97).

The following Patent and Application Publications may also provide useful information and the contents of the relevant process sections are hereby incorporated herein by reference:

FR 2458547; FR 2500450 (& GB 2094299, GB 2141716 & U.S. Pat. No. 4,476,136); DE 2923295 (& GB 2028306, GB 2054575, U.S. Pat. No. 4,287,351, U.S. Pat. No. 4,348,393, U.S. Pat. No. 4,413,001, U.S. Pat. No. 4,435,415 & U.S. Pat. No. 4,526,786), DE 3017499 (& GB 2053196, U.S. Pat. No.

4,346,102 & U.S. Pat. No. 4,372,967); U.S. Pat. No. 4,705,799; European Patent Application Nos. 0,312,000; 0,127,902; 0,184,170; 0,352,781; 0,316,594;

The skilled organic chemist will be able to use and adapt the information contained and referenced within the above references, and accompanying Examples therein and also the Examples herein, to obtain necessary starting materials, and products.

Process Section:

Thus, the present invention also provides that the compounds of the formula (I) and pharmaceutically-acceptable salts and in vivo hydrolysable esters thereof, can be prepared by a process (a) to (h) as follows (wherein the variables are as defined above unless otherwise stated):

(a) by modifying a substituent in, or introducing a new substituent into, the substituent group R1 of HET of another compound of formula (I)—for instance by (i) displacement of a functional group from a compound of formula (I) by another functional group, (ii) by oxidation or (iii) reduction of a compound of formula (I), by (iv) addition of a reagent to or (v) elimination of a reagent from a compound of formula (I), by (vi) metathesis of a compound of formula (I) into a modified compound of formula (I), or by (vii) rearrangement of a compound of formula (I) to an isomeric compound of formula (I); or by modifying a substituent in, or introducing a new substituent into, the group Q of another compound of formula (I)—for instance by (i) displacement of a functional group from a compound of formula (I) by another functional group, (ii) by oxidation or (iii) reduction of a compound of formula (I), by (iv) addition of a reagent to or (v) elimination of a reagent from a compound of formula (I), by (vi) metathesis of a compound of formula (I) into a modified compound of formula (I), or by (vii) rearrangement of a compound of formula (I) to an isomeric compound of formula (I) (Scheme I shows examples drawn from the range of suitable methods); or (b) by reaction of a compound of formula (II):

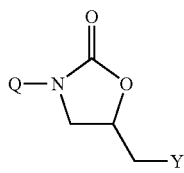

(II)

wherein Y is a displaceable group (which may be preformed, such as chloro or mesylate, or generated in-situ, for example under Mitsunobu conditions) with a compound of the formula (III):

HET (III)

wherein HET (of formula (Ia) to (If), already substituted and optionally protected) is HET-H free-base form or HET-anion formed from the free base form (Scheme II shows examples drawn from the range of suitable methods); or (c) by reaction of a compound of the formula (IV):

Q-Z (IV)

wherein Z is an isocyanate, amine or urethane group with an epoxide of the formula (V) wherein the epoxide group serves as a leaving group at the terminal C-atom and as a protected hydroxy group at the internal C-atom; or with a related compound of formula (VI) where the hydroxy group at the internal C-atom is conventionally protected e.g. with an acetyl group and where the leaving group Y at the terminal C-atom is a conventional leaving group e.g. a chloro- or mesyloxy-group;

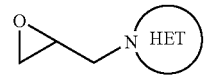

(V)

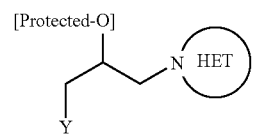

(VI)

(Scheme III shows examples drawn from the range of suitable methods), or (d) (i) by coupling, using catalysis by transition metals such as palladium(0), of a compound of formula (VII):

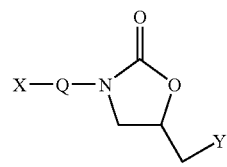

(VII)

wherein Y' is a group HET as hereinbefore defined, X is a replaceable substituent—such as chloride, bromide, iodide, or trifluoromethylsulfonyloxy;

with a compound of the formula (VIII), or an analogue thereof, which is suitable to give a T substituent as defined by (TA)-(TE), in which the link is via an $sp^2$ carbon atom (D=CH=C-Lg where Lg is a leaving group such as chloride, bromide, iodide, or trifluoromethylsulfonyloxy; or as in the case of reactions carried out under Heck reaction conditions Lg may also be hydrogen) or in which the link is via an N atom (D=NH)

$$T_1\!\!\diagdown\!\!D\!\!\diagup\!\!T_2$$

(VIII)

where $T_1$ and $T_2$ may be the same or different or may together with D form a ring of type T as hereinbefore described (Scheme IV shows examples drawn from the range of suitable methods);

(d) (ii) by coupling, using catalysis by transition metals such as palladium(0), of a compound of formula (VIIA):

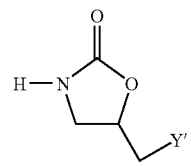

(VIIA)

wherein Y' is a group HET as hereinbefore defined, with a compound [Aryl]-X, where X is a replaceable substituent— such as chloride, bromide, iodide, or trifluoromethylsulfonyloxy, or an analogue thereof (Scheme IV shows an example drawn from the range of suitable methods);

(e) Where N-HET is 1,2,3-triazole there is the additional possibility by cycloaddition via the azide (wherein Y in (II) is azide), with a substituted acetylene or a masked acetylene (such as a vinyl sulfone, a nitroloefin, or an enamine, or a substituted cyclohexa-1,4-diene derivative (Scheme II shows examples drawn from the range of suitable methods);

(f) Where N-HET is 1,2,3-triazole there is the additional possibility of synthesis by reaction of a compound of formula (II) where Y=NH₂ (primary amine) with a compound of formula (IX), namely the arenesulfonylhydrazone of a methyl ketone that is further geminally substituted on the methyl group by two substituents (Y' and Y") capable of being eliminated from this initial, and the intermediate, substituted hydrazones as HY' and HY" (or as conjugate bases thereof) (Scheme V shows an example drawn from the range of suitable methods);

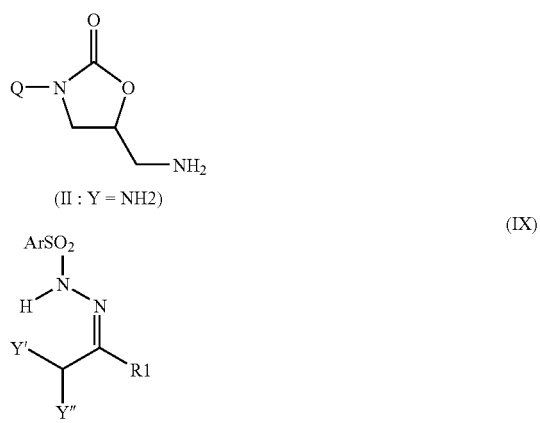

(g) where N-HET is 1,2,3-triazole there is the additional possibility of regioselective. synthesis by cycloaddition via the azide (wherein Y in (II) is azide) with a terminal alkyne using Cu(I) catalysis in e.g. aqueous alcoholic solution at ambient temperatures to give 4-substituted 1,2,3-triazoles;

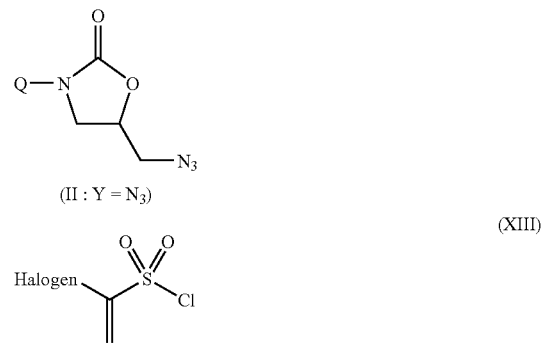

(h) where N-HET is 1,2,3-triazole there is the additional possibility of regioselective synthesis by cycloaddition via the azide (wherein Y in (II) is azide) with an alpha-halovinylsulfonylchloride (XIII);

and thereafter if necessary: (i) removing any protecting groups; (ii) forming a pharmaceutically-acceptable salt; (iii) forming an in-vivo hydrolysable ester.

The main synthetic routes are illustrated in Schemes (I) to (VII) below (with Q as phenyl, and T, R1, R2, R3, and A defined with reference to analogous substituents defined elsewhere herein). The compounds of the invention may be prepared by analogous chemistry adapted from these Schemes. Schemes (II), (VI), and (VII) also show the preparation of 1,2,3-triazoles via the azide (prepared from the relevant hydroxy compound) and the amine (prepared e.g. from the azide) respectively.

Scheme I

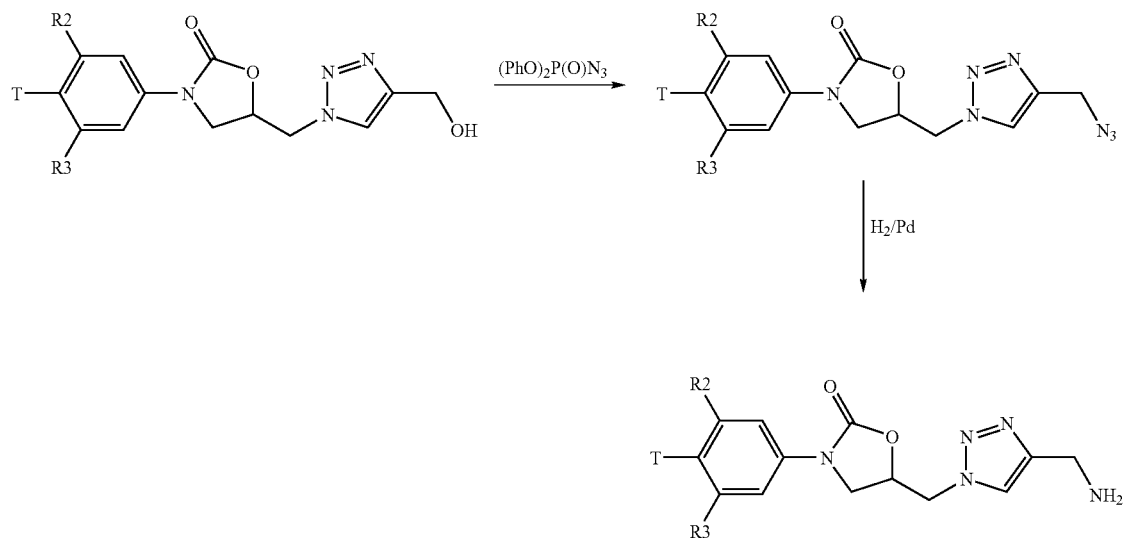

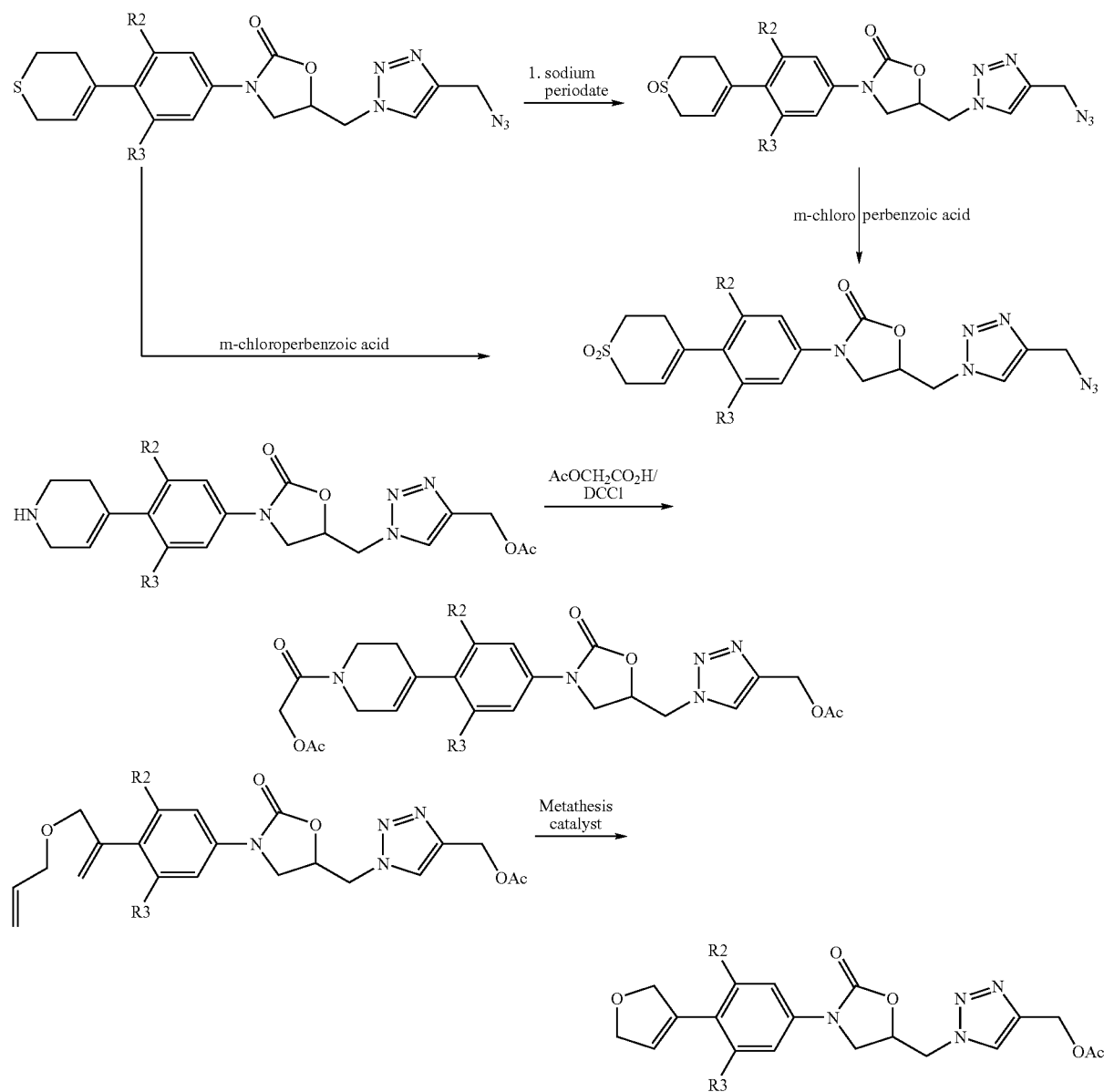
Scheme II
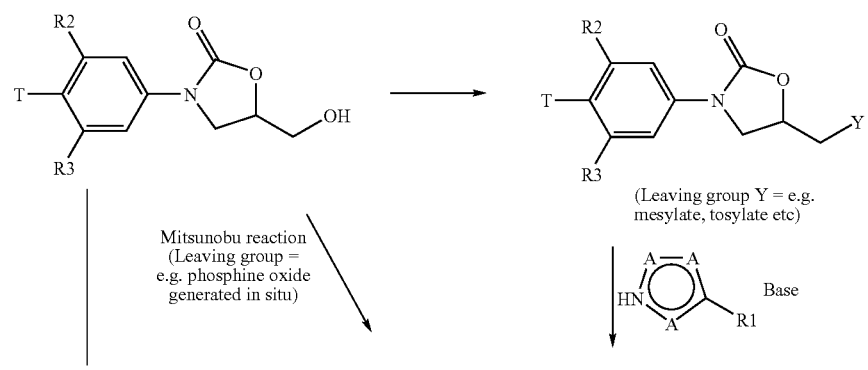

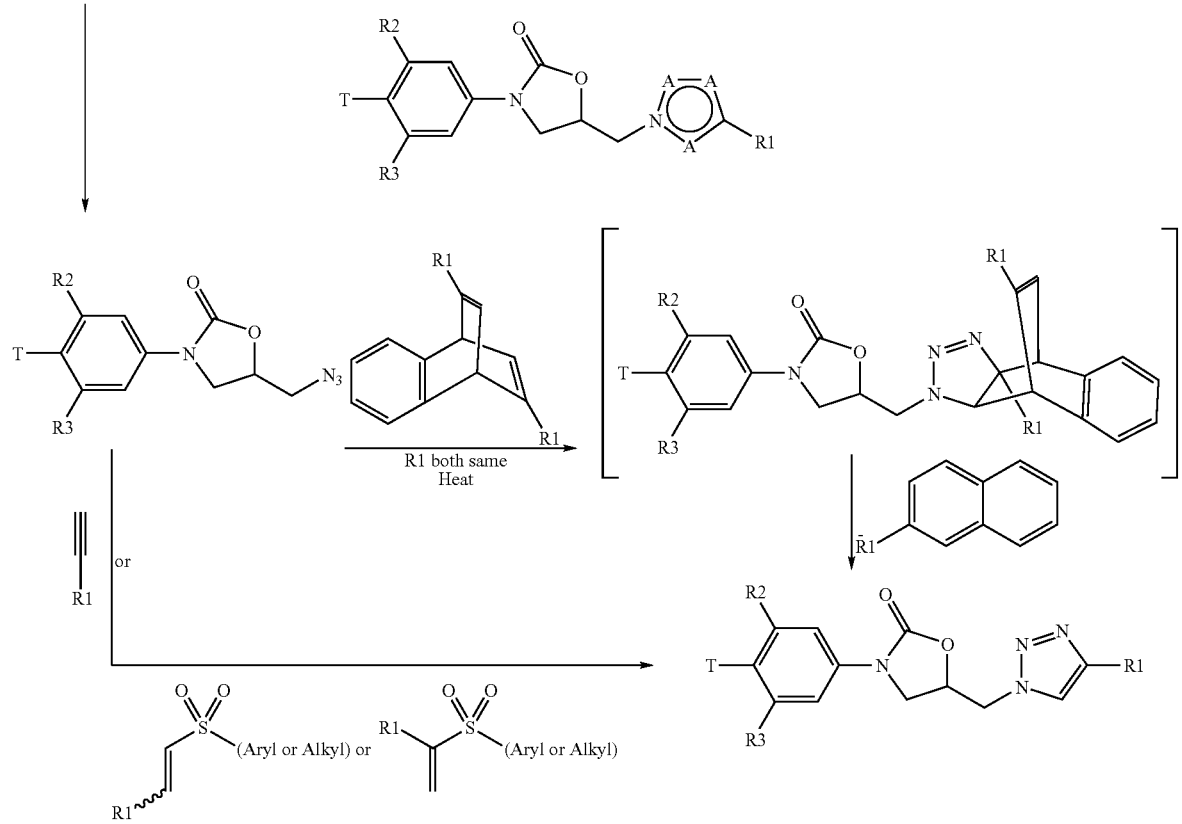
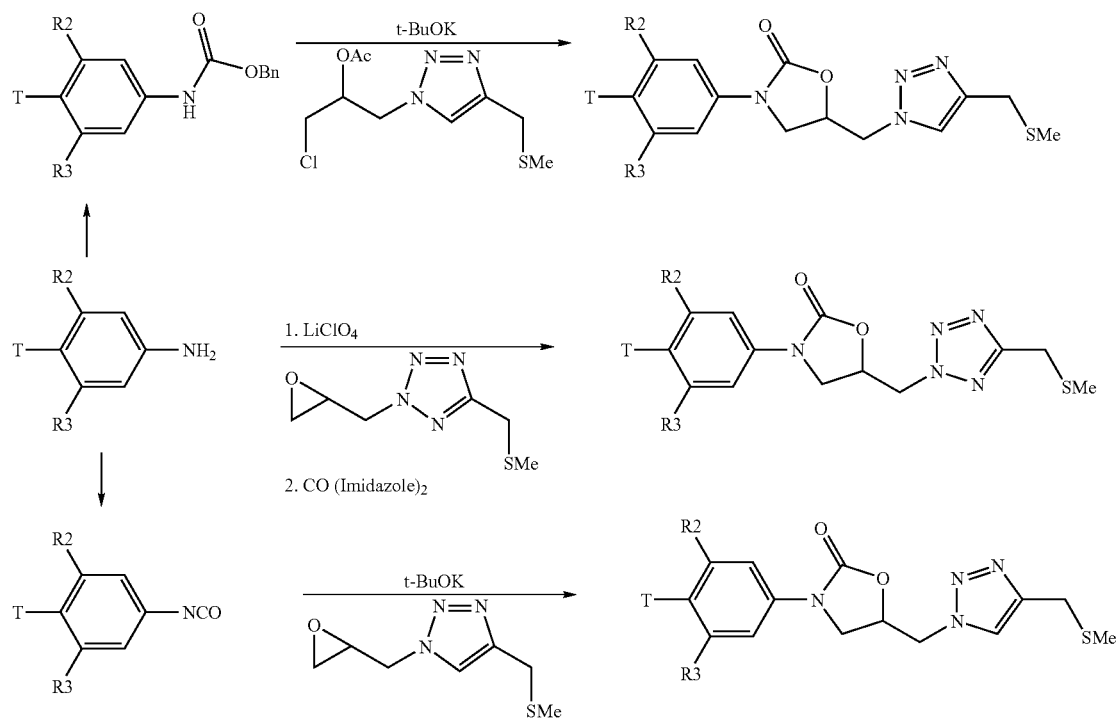
Scheme III

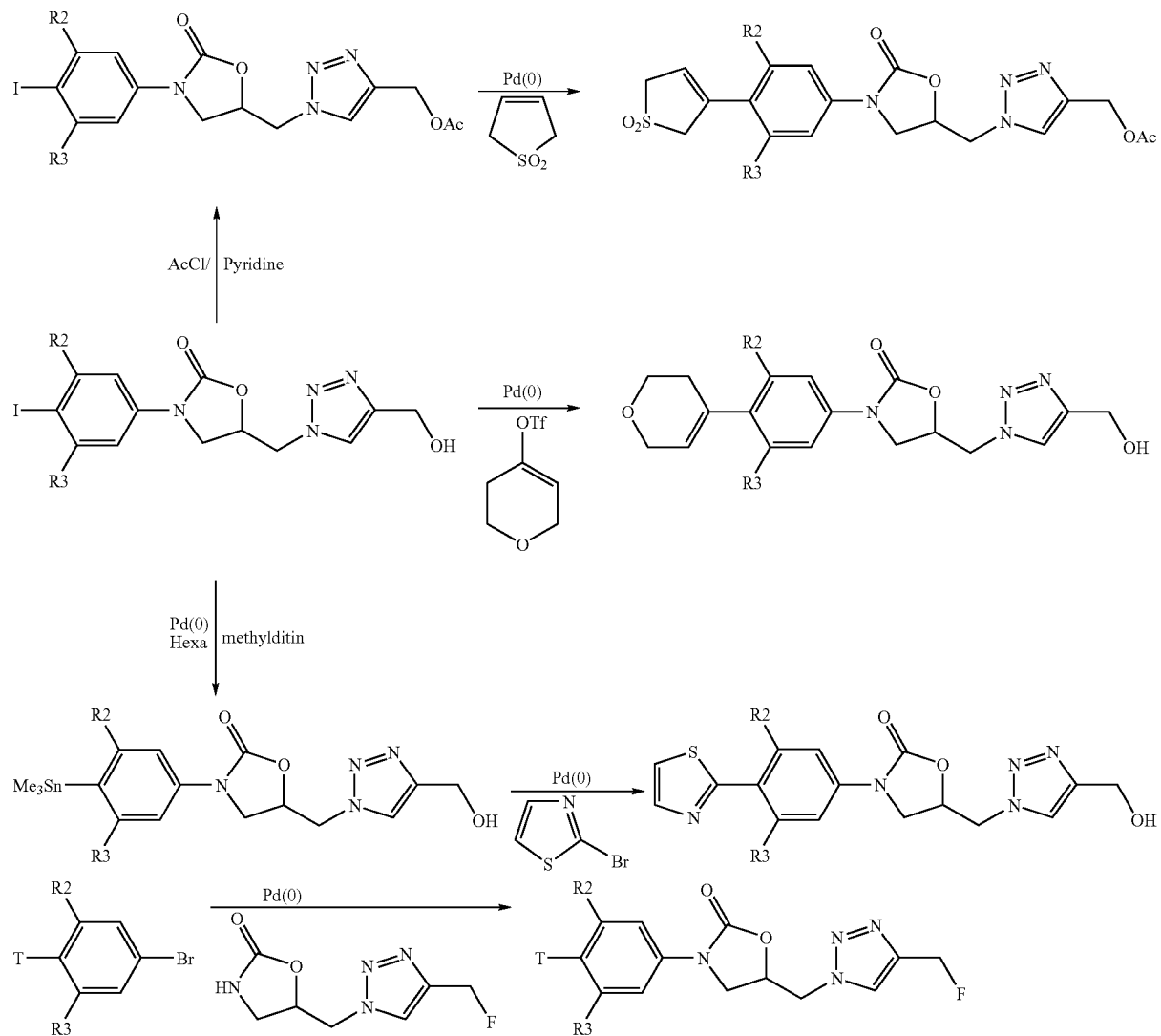
Scheme V
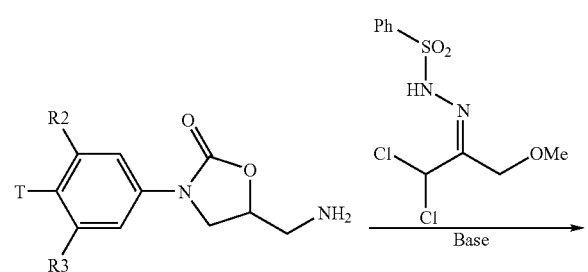
Scheme VI
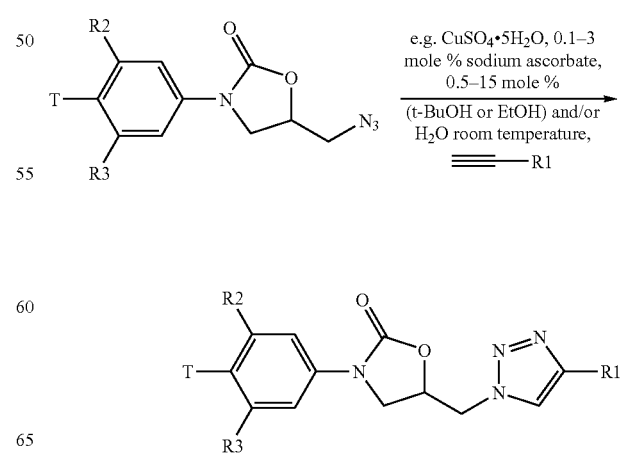

Scheme VII

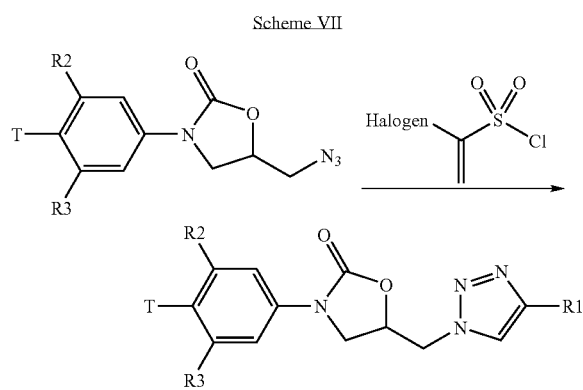

Deprotection, salt formation or in-vivo hydrolysable ester formation may each be provided as a specific final process step.

The N-linked hetereocycle can of course be prepared early in the overall synthesis, and then other functional groups changed.

Where Y is a displaceable group, suitable values for Y are for example, a halogeno or sulfonyloxy group, for example a chloro, bromo, methanesulfonyloxy or toluene-4-sulfonyloxy group.

General guidance on reaction conditions and reagents may be obtained in Advanced Organic Chemistry, 4$^{th}$ Edition, Jerry March (publisher: J. Wiley & Sons), 1992. Necessary starting materials may be obtained by standard procedures of organic chemistry, such as described in this process section, in the Examples section or by analogous procedures within the ordinary skill of an organic chemist. Certain references are also provided which describe the preparation of certain suitable starting materials, for example International Patent Application Publication No. WO 97/37980, the contents of which are incorporated here by reference. Processes analogous to those described in the references may also be used by the ordinary organic chemist to obtain necessary starting materials.

(a) Methods for converting substituents into other substituents are known in the art. For example an alkylthio group may be oxidised to an alkylsulfinyl or alkysulfonyl group, a cyano group reduced to an amino group, a nitro group reduced to an amino group, a hydroxy group alkylated to a methoxy group, a hydroxy group thiomethylated to an arylthiomethyl or a heteroarylthiomethyl group (see, for example, Tet. Lett., 585, 1972), a carbonyl group converted to a thiocarbonyl group (eg. using Lawsson's reagent) or a bromo group converted to an alkylthio group. It is also possible to convert one Rc group into another Rc group as a final step in the preparation of a compound of the formula (I), for example, acylation of a group of formula (TC5) wherein Rc is hydrogen.

(b)(i) Reaction (b)(i) (in which Y is initially hydroxy) is performed under Mitsunobu conditions, for example, in the presence of tri-n-butylphosphine and diethyl azodicarboxylate (DEAD) in an organic solvent such as THF, and in the temperature range 0° C.–60° C., but preferably at ambient temperature. Details of Mitsunobu reactions are contained in Tet. Letts., 31, 699, (1990); The Mitsunobu Reaction, D. L. Hughes, Organic Reactions, 1992, Vol. 42, 335–656 and Progress in the Mitsunobu Reaction, D. L. Hughes, Organic Preparations and Procedures International, 1996, Vol. 28, 127–164.

Compounds of the formula (II) wherein Y is hydroxy may be obtained as described in the references cited herein (particularly in the section proceeding the discussion of protecting groups), for example, by reacting a compound of the formula (X) with a compound of formula (XI):

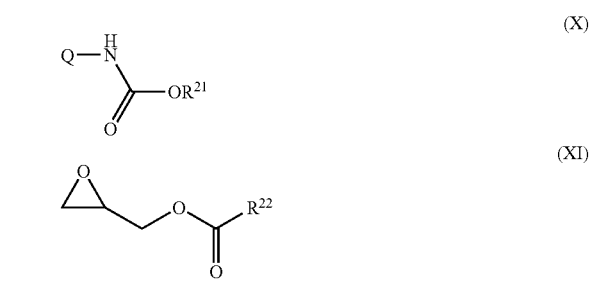

wherein R$^{21}$ is (1–6C)alkyl or benzyl and R$^{22}$ is (1–4C)alkyl or —S(O)$_n$(1–4C)alkyl where n is 0, 1 or 2. Preferably R$^{22}$ is (1–4C)alkyl.

In particular, compounds of the formula (II), (X) and (XI) may be prepared by the skilled man, for example as described in International Patent Application Publication Nos. WO95/07271, WO97/27188, WO 97/30995, WO 98/01446 and WO 98/01447, the contents of which are hereby incorporated by reference, and by analogous processes.

If not commercially available, compounds of the formula (III) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie, E8a, Pt.I (1993), 45–225, B. J. Wakefield.

(b)(ii) Reactions (b)(ii) are performed conveniently in the presence of a suitable base such as, for example, an alkali or alkaline earth metal carbonate, alkoxide or hydroxide, for example sodium carbonate or potassium carbonate, or, for example, an organic amine base such as, for example, pyridine, 2,6-lutidine, collidine, 4-dimethylaminopyridine, triethylamine, morpholine or diazabicyclo-[5.4.0]undec-7-ene, the reaction is also preferably carried out in a suitable inert solvent or diluent, for example methylene chloride, acetonitrile, tetrahydrofuran, 1,2-dimethoxyethane, N,N-dimethylformamide, N,N-dimethylacetamide, N-methylpyrrolidin-2-one or dimethylsulfoxide at and at a temperature in the range 25–60° C.

When Y is chloro, the compound of the formula (II) may be formed by reacting a compound of the formula (II) wherein Y is hydroxy (hydroxy compound) with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature. A compound of the formula (II) wherein Y is chloro or iodo may also be prepared from a compound of the formula (II) wherein Y is mesylate or tosylate, by reacting the latter compound with lithium chloride or lithium iodide and crown ether, in a suitable organic solvent such as THF, in a temperature range of ambient temperature to reflux.

When Y is (1–4C)alkanesulfonyloxy or tosylate the compound (II) may be prepared by reacting the hydroxy compound with (1–4C)alkanesulfonyl chloride or tosyl chloride in the presence of a mild base such as triethylamine or pyridine.

When Y is a phosphoryl ester (such as (PhO)$_2$—P(O)—O—) or Ph$_2$—P(O)—O— the compound (II) may be prepared from the hydroxy compound under standard conditions.

(c) Reaction (c) is performed under conditions analogous to those described in the following references which disclose how suitable and analogous starting materials may be obtained.

Reaction (c) is especially suitable for compounds in which HET-H is a weakly acidic heterocycle (such as, for example, triazole or tetrazole).

Compounds of the formula Q-Z wherein Z is an isocyanate may be prepared by the skilled chemist, for example by analogous processes to those described in Walter A. Gregory et al in J. Med. Chem. 1990, 33, 2569–2578 and Chung-Ho Park et al in J. Med. Chem. 1992, 35, 1156–1165. Compounds of the formula Q-Z wherein Z is a urethane may be prepared by the skilled chemist, for example by analogous processes to those described in International Patent Application Publication Nos. WO 97/30995 and WO 97/37980.

A similar reaction to reaction (c) may be performed in which Q-Z wherein Z is a amine group is reacted with the epoxide (optionally in the presence of an organic base), and the product is reacted with, for example, phosgene to form the oxazolidinone ring. Such reactions and the preparation of starting materials is within the skill of the ordinary chemist with reference to the above-cited documents disclosing analogous reactions and preparations.

Epoxides of the formula (V) may be prepared from the corresponding compound of formula (XII):

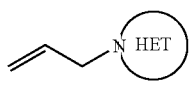

(XII)

Certain such epoxide and alkene intermediates are novel and are provided as a further feature of the invention. Asymmetric epoxidation may be used to give the desired optical isomer. Compounds of formula (VI) may be obtained from epoxides of formula (V); alternatively compounds of formula (VI) may be used as precursors for epoxides of formula (V) according to the relative ease of synthesis in each case. The skilled chemist will appreciate that the epoxides of formula (V) and the compounds of formula (VI) are structurally equivalent and the choice between them will be made on the grounds of availability, convenience, and cost.

(d) The transition metal catalysed coupling reaction to form a C—C or N—C bond from the corresponding aryl derivatives and the arenes, heteroarenes, olefins, alkynes, or amines is performed under conventional conditions (see for instance J. K. Stille, Angew. Chem. Int. Ed. Eng., 1986, 25, 509–524; N. Miyaura and A. Suzuki, Chem. Rev., 1995, 95, 22457–2483; D. Baranano, G. Mann, and J. F. Hartwig, Current Org. Che., 1997, 1, 287–305; S. P. Stanforth, Tetrahedron, 1998, 54, 263–303). The reaction d (ii) may be conveniently carried out under the conditions described Tetrahedron Letters (2001), 42 (22), 3681–3684, or in the analogous conventional conditions described in the above mentioned literature. In such a procedure a preferred variation of X may be bromine.

(e) The cycloaddition reaction to form 1,2,3 triazoles from the corresponding azide is performed under conventional conditions. Compounds of the formula (II) wherein Y is azide may be obtained as described in the references cited herein (particularly in the section proceeding the discussion of protecting groups), for example from the corresponding compounds in which Y is hydroxy or mesylate.

(f) The reaction of amines of formula (I, Y=NH2) with arenesulfonyl hydrazones to form 1,2,3 triazoles may be carried out as described in the literature (Sakai, Kunikazu; Hida, Nobuko; Kondo and Kiyosi "Reactions of α-polyhalo ketone tosylhydrazones with sulfide ion and primary amines. Cyclization to 1,2,3-thiadiazoles and 1,2,3-triazoles." Bull. Chem. Soc. Jpn. (1986), 59 (1), 179–83; Sakai, Kunikazu; Tsunemoto, Daiei; Kobori, Takeo; Kondo, Kiyoshi; Hida and Nobuko: "1,2,3-Trihetero 5-membered heterocyclic compounds" EP103840 A2 19840328). The leaving groups Y, Y' may be chloro or any other group capable of being eliminated from the arenesulfonyl hydrazone during the reaction with the amine. The skilled chemist will also appreciate that a similar reaction may be used to produce other substituted triazoles suitable for incorporation into related processes such as reaction with compounds of formula (IV) in process (c).

(g) The reaction of azides of formula (II, Y=N$_3$) with as terminal alkynes using Cu(I) catalysis to give regioselectively 4-substituted 1,2,3-triazole compounds of formula (I) may be carried out as described in the literature (for instance V. V. Rostovtsev, L. G. Green, V.V. Fokin, and K. B. Sharpless, Angew. Chem. Int. Ed., 2002, 41, 2596–2599).

(h) The reaction of alkylazides with 1-halovinylsulfonyl chlorides at a temperature between 0° C. and 100° C. either neat or in an inert diluent such as chlorobenzene, chloroform or dioxan gives 4-halogenated 1,2,3-triazole compounds of formula (I). The reaction may be applied to 1-fluoro-, 1-chloro-, 1-bromo-, or 1-iodo-vinylsulfonyl-chlorides.

The removal of any protecting groups, the formation of a pharmaceutically-acceptable salt and/or the formation of an in vivo hydrolysable ester are within the skill of an ordinary organic chemist using standard techniques. Furthermore, details on the these steps, for example the preparation of in-vivo hydrolysable ester prodrugs has been provided in the section above on such esters, and in certain of the following non-limiting Examples.

When an optically active form of a compound of the formula (I) is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the formula (I) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the formula (I), or a pharmaceutically-acceptable salt, or in-vivo hydrolysable ester thereof, for use as a medicament; and for use as an anti-bacterial agent; and the use of a compound of the formula (I) of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the formula (I), an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration as eye-drops, for administration by inhalation (for example as a finely divided powder or a liquid aerosol), for administration by insufflation (for example as a finely divided powder) or for parenteral administration (for example as a sterile aqueous or oily solution for intravenous, subcutaneous, sub-lingual, intramuscular or intramuscular dosing or as a suppository for rectal dosing).

In addition to the compounds of the present invention, the pharmaceutical composition of this invention may also contain (ie through co-formulation) or be co-administered (simultaneously, sequentially or separately) with one or more known drugs selected from other clinically useful antibacterial agents (for example, β-lactams, macrolides, quinolones or aminoglycosides) and/or other anti-infective agents (for example, an antifungal triazole or amphotericin). These may include carbapenems, for example meropenem or imipenem, to broaden the therapeutic effectiveness. Compounds of this invention may also be co-formulated or co-administered with bactericidal/permeability-increasing protein (BPI) products or efflux pump inhibitors to improve activity against gram negative bacteria and bacteria resistant to antimicrobial agents.

The compositions of the invention may be obtained by conventional procedures using conventional pharmaceutical excipients, well known in the art. Thus, compositions intended for oral use may contain, for example, one or more colouring, sweetening, flavouring and/or preservative agents. A pharmaceutical composition to be dosed intravenously may contain advantageously (for example to enhance stability) a suitable bactericide, antioxidant or reducing agent, or a suitable sequestering agent.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol. Solubility enhancing agents, for example cyclodextrins may be used.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 50 mg to 5 g of active agent compounded with an appropriate and convenient amount of excipients which may vary from about 5 to about 98 percent by weight of the total composition. Dosage unit forms will generally contain about 200 mg to about 2 g of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 mgkg$^{-1}$ to 20 mgkg$^{-1}$ of a compound of this invention, the composition being administered 1 to 4 times per day. In another embodiment a daily dose of 5 mgkg$^{-1}$ to 20 mgkg$^{-1}$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

In the above other, pharmaceutical composition, process, method, use and medicament manufacture features, the alternative and preferred embodiments of the compounds of the invention described herein also apply.

Biological Activity:

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against *enterococci, pneumococci* and *methicillin* resistant strains of *S. aureus* and coagulase negative *staphylococci*, together with haemophilus and moraxella strains. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of 10$^4$ CFU/spot. Typically, compounds are active in the range 0.01 to 256 μg/ml.

*Staphylococci* were tested on agar, using an inoculum of 10$^4$ CFU/spot and an incubation temperature of 37° C. for 24 hours—standard test conditions for the expression of methicillin resistance.

*Streptococci* and *enterococci* were tested on agar supplemented with 5% defibrinated horse blood, an inoculum of 10$^4$ CFU/spot and an incubation temperature of 37° C. in an atmosphere of 5% carbon dioxide for 48 hours—blood is required for the growth of some of the test organisms. Fastidious Gram negative organisms were tested in Mueller-Hinton broth, supplemented with hemin and NAD, grown aerobically for 24 hours at 37° C., and with an innoculum of 5×10$^4$ CFU/well.

For example, the following results were obtained for the compound of Example 3:

| Organism | | MIC (μg/ml) |
|---|---|---|
| *Staphylococcus aureus*: | MSQS | 4 |
| | MRQR | 8 |
| *Streptococcus pneumoniae* | | 2 |
| *Streptococcus pyogenes* | | 2 |
| *Haemophilus influenzae* | | 2 |
| *Moraxella catarrhalis* | | 4 |

MSQS = methicillin sensitive and quinolone sensitive
MRQR = methicillin resistant and quinolone resistant The activity of the compounds of the invention against MAO-A was tested using a standard in-vitro assay based on human liver enzyme expressed in yeast as described in Biochem. Biophys. Res. Commun. 1991, 181, 1084–1088. The compounds of the invention showed decreased MAO-A potency compared with analogues from the known art with C-5 side chains such as acetamidomethyl or unsubstituted azolylmethyl or hydroxymethyl. The compounds of the invention showed decreased MAO-A potency compared with analogues in which the HET group of formula (Ia) to (If) is unsubstituted. When Ki values were measured in such an assay as above, Example 3 showed a Ki value of >177 μg/ml.

MAO activity in general comprises activity in both MAO-A and MAO-B enzymes. The compounds of the invention in general demonstrate favourable profiles against both enzymes.

Certain intermediates and/or Reference Examples described hereinafter within the scope of the invention may also possess useful activity, and are provided as a further feature of the invention.

The invention is now illustrated but not limited by the following Examples in which unless otherwise stated:
(i) evaporations were carried out by rotary evaporation in vacuo and work-up procedures were carried out after removal of residual solids by filtration;
(ii) operations were carried out at ambient temperature, that is typically in the range 18–26° C. and without exclusion of air unless otherwise stated, or unless the skilled person would otherwise work under an inert atmosphere;
(iii) column chromatography (by the flash procedure) was used to purify compounds and was performed on Merck Kieselgel silica (Art. 9385) unless otherwise stated;
(iv) yields are given for illustration only and are not necessarily the maximum attainable;
(v) the structure of the end-products of the invention were generally confirmed by NMR and mass spectral techniques [proton magnetic resonance spectra were generally determined in DMSO-$d_6$ unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ (delta) scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected];
(vi) each intermediate was purified to the standard required for the subsequent stage and was characterised in sufficient detail to confirm that the assigned structure was correct; purity was assessed by HPLC, TLC, or NMR and identity was determined by infra-red spectroscopy (IR), mass spectroscopy or NMR spectroscopy as appropriate;
(vii) in which the following abbreviations may be used:
DMF is N,N-dimethylformamide; DMA is N,N-dimethylacetamide; TFA is trifluoroacetic acid; TLC is thin layer chromatography; HPLC is high pressure liquid chromatography; MPLC is medium pressure liquid chromatography; DMSO is dimethylsulfoxide; CDCl$_3$ is deuterated chloroform; MS is mass spectroscopy; ESP is electrospray; EI is electron impact; CI is chemical ionisation; APCI is atmospheric pressure chemical ionisation; NOE is nuclear Overhauser effect (NMR experiment); EtOAc is ethyl acetate; MeOH is methanol.

The microwave used was a "Smith Syntheziser" made by Personal Chemistry.

EXAMPLE 1

(5R)-3-[4-(1(R,S)-Oxo-3,6-dihydro-2H-thiopyran-4-yl)-3-fluorophenyl]-5-[(4-carbonitrile)-1,2,3-triazol-1-ylmethyl]oxazolidin-2-one (5R)-3-[4-(1(R,S)-Oxo-3,6-dihydro-2H-thiopyran-4-yl)-3-fluorophenyl]-5-azidomethyloxazolidin-2-one (0.21 g, 0.6 mmol) (Reference Example 1) was dissolved in dry 1,4-dioxane (4 ml), 2-chloroacrylonitrile(78.7 mg, 0.9 mmol) was added and the resulting mixture was refluxed for 12 hours under vigorous stirring. The solvent was removed under vacuum and the residue was purified by flash chromatography on silica gel with 5% methanol in dichloromethane to give the title product (0.21 g) as the only isomer isolated. WO 98/02423 describes the use of chloroacrylonitrile in the "Process For Preparing 1-Substituted 4-cyano-1,2,3 Triazoles".

MS (ESP): 402.12 (MH$^+$) for C$_{18}$H$_{16}$FN$_5$O$_3$S $^1$H-NMR (DMSO-$d_6$) δ: 2.57 (m, 1H); 2.97 (m, 2H); 3.13 (m, 1H); 3.39 (m, 1H); 3.67 (m, 1H); 3.94 (m, 1H); 4.29 (dd, 1H); 4.97 (d, 2H); 5.20 (m, 1H); 5.85 (m, 1H); 7.30 (dd, 1H); 7.41 (t, 1H); 7.47 (dd, 1H); 9.15 (s, 1H).

EXAMPLE 2

(5R)-3-[4-(1(R,S)-Oxo-3,6-dihydro-2H-thiopyran-4-yl)-3-fluorophenyl]-5-[(4-methoxycarbonyl)-1,2,3-triazol-1-ylmethyl]oxazolidin-2-one (5R)-3-[4-(1(R,S)-Oxo-3,6-dihydro-2H-thiopyran-4-yl)-3-fluorophenyl]-5-azidomethyloxazolidin-2-one (500 mg, 1.43 mmol) (Reference Example 1) was dissolved in dry 1,4-dioxane (1.0 ml), 2-propynoic acid methyl ester (180 mg, 2.14 mmol) was added and the resulting mixture was refluxed for 12 hours under vigorous stirring. The solvent was removed under vacuum and the residue was purified by flash chromatography on silica gel with 5% methanol in dichloromethane to give the title product (486 mg).

MS (ESP): 435.13 (MH$^+$) for C$_{19}$H$_{19}$FN$_4$O$_5$S $^1$H-NMR (DMSO-$d_6$) δ: 2.56 (m, 1H); 2.97 (m, 2H); 3.13 (m, 1H); 3.39 (m, 1H); 3.67 (m, 1H); 3.86 (s, 3H); 3.96 (m, 1H); 4.27

(dd, 1H); 4.90 (d, 2H); 5.21 (m, 1H); 5.84 (m, 1H); 7.31 (dd, 1H); 7.41 (t, 1H); 7.47 (dd, 1H); 8.85 (s, 1H).

EXAMPLE 3

(5R)-3-[4-(1(R,S)-Oxo-3,6-dihydro-2H-thiopyran-4-yl)-3-fluorophenyl]-5-[(4-azidomethyl)-1,2,3-triazol-1-ylmethyl]oxazolidin-2-one

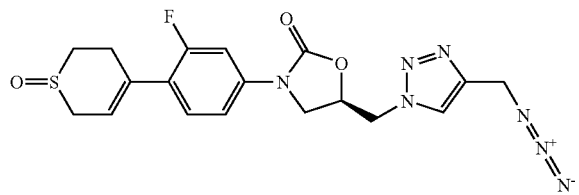

(5R)-3-[4-(1(R,S)-Oxo-3,6-dihydro-2H-thiopyran-4-yl)-3-fluorophenyl]-5-[(4-hydroxymethyl)-1,2,3-triazol-1-ylmethyl]oxazolidin-2-one (1.1 g, 2.7 mmol) (Example 4) was suspended in dichloromethane (10 ml). 1,8-Diazabicyclo[5.4.0]undec-7-ene (0.71 g, 4.7 mmol) was added and the reaction mixture was cooled to −5° C. Diphenylphosphoryl azide (0.89 g, 3.25 mmol) was added dropwise and it was stirred for 18 hours at room temperature. The solvent was evaporated and the residue chromatographed on silica gel with 5% methanol in dichloromethane to give the title product (1.02 g).

MS (ESP): 432.17 (MH$^+$) for $C_{18}H_{18}FN_7O_3S$ $^1$H-NMR (DMSO-d$_6$) δ: 2.58 (m, 1H); 2.85–3.00 (m, 2H); 3.12 (m, 1H); 3.40 (m, 1H); 3.67 (m, 1H); 3.92 (dd, 1H); 4.28 (dd, 1H); 4.53 (s, 2H); 4.86 (m, 2H); 5.18 (m, 1H); 5.84 (m, 1H); 7.29 (dd, 1H); 7.40 (dd, 1H); 7.46 (dd, 1H); 8.25 (s, 1H).

EXAMPLE 4

(5R)-3-[4-(1(R,S)-Oxo-3,6dihydro-2H-thiopyran-4-yl)-3-fluorophenyl]-5-[(4-hydroxymethyl)-1,2,3-triazol-1-ylmethyl]oxazolidin-2-one

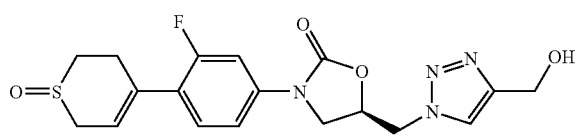

(5R)-3-[4-(1(R,S)-Oxo-3,6-dihydro-2H-thiopyran-4-yl)-3-fluorophenyl]-5-azidomethyloxazolidin-2-one (3 g, 8.56 mmol) (Reference Example 1) was dissolved in refluxing toluene (25 ml). Propargyl alcohol (1.93 g, 34.35 mmol) was added and the resulting 2-phase mixture was refluxed for 18 hours under vigorous stirring. The solvent was removed under vacuum and the residue chromatographed on silicagel with 10% methanol in chloroform to give 1.1 g of the title compound, next to 1.2 g of the corresponding 5-(hydroxymethyl) regioisomer.

MS (ESP): 407.14 (MH$^+$) for $C_{18}H_{19}FN_4O_4S$ $^1$H-NMR (DMSO-d$_6$) δ: 2.58 (m, 1H); 2.85–3.00 (m, 2H); 3.14 (m, 1H); 3.40 (m, 1H); 3.68 (m, 1H); 3.92 (dd, 1H); 4.27 (dd, 1H); 4.53 (d, 2H); 4.82 (m, 2H); 5.15 (m, 1H); 5.23 (dd, 1H, exchangeable); 5.84 (m, 1H); 7.31 (dd, 1H); 7.40 (dd, 1H); 7.48 (dd, 1H); 8.03 (s, 1H). 4-substitution on the triazole moiety was confirmed by NOE experiments. The 5-hydroxymethyl regioisomer shows H-4 of triazole moiety at 7.66 ppm.

EXAMPLE 5

(5R)-3-[4-(1(R,S)-Oxo-3,6-dihydro-2H-thiopyran-4-yl)-3-fluorophenyl]-5-[(4-trifluoromethyl)-1,2,3-triazol-1-ylmethyl]oxazolidin-2-one

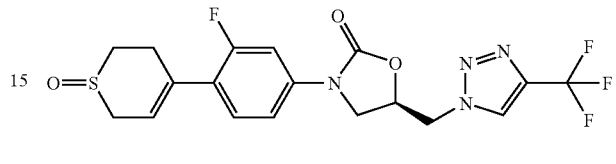

(5R)-3-[4-(3,6-Dihydro-2H-thiopyran-4-yl)-3-fluorophenyl]-5-azidomethyloxazolidin-2-one (0.33 g, 1 mmol) (Reference Example 1) was dissolved in refluxing toluene (15 ml). 3,3,3-Trifluoro-1-(phenylsulfonyl)-1-propene (0.24 g, 1 mmol) was added and the resulting mixture was refluxed for 12 hours under vigorous stirring. The solvent was removed under vacuum and the crude product was dissolved in methanol/ethylacetate/water (1:1:1, 30 ml). Sodium periodate (0.21 g, 1 mmol) was added, the reaction mixture was stirred at room temperature for 1 hour. It was extracted with dichloromethane (3×20 ml), the organic phase was dried over magnesium sulfate and concentrated to dryness. This residue was purified by flash chromatography on silicagel with 5% methanol in dichloromethane to give 100 mg of the title compound, next to 13 mg of the corresponding 5-trifluoromethyl compound.

MS (ESP): 439.22 (MH$^+$) for $C_{18}H_{16}F_4N_4O_3S$ $^1$H-NMR (CDC$_3$) δ: 2.75 (m, 1H); 2.97 (m, 1H); 3.10 (m, 1H); 3.21 (m, 1H); 3.46 (m, 1H); 3.64 (m, 1H); 3.96 (dd, 1H); 4.26 (dd, 1H); 4.80 (m, 1H); 4.90 (m, 1H); 5.12 (m, 1H); 5.83 (m, 1H); 7.11 (m, 1H); 7.25 (dd, 1H); 7.37 (dd, 1H); 8.14 (s, 1H).

The 5-trifluoromethyl regioisomer shows H-4 of the triazole moiety at 8.08 ppm.

REFERENCE EXAMPLE 1

(5R)-3-[4-(1(R,S)-Oxo-3,6-dihydro-2H-thiopyran-4-yl)-3-fluorophenyl]-5-azidomethyloxazolidin-2-one

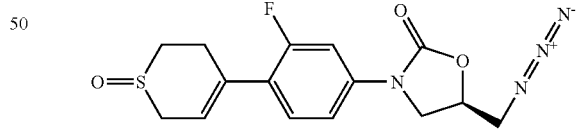

(5R)-3-[4-(3,6-Dihydro-2H-thiopyran-4-yl)-3-fluorophenyl]-5-azidomethyloxazolidin-2-one (2.3 g, 6.5 mmol) (see WO 01/81350) was dissolved in methanol/ethylacetate (1:1, 100 ml) and sodium periodate (1.75 g, 8.2 mmol) dissolved in water (20 ml) was added dropwise over 1 hour. The reaction mixture was stirred for 7 hours at room temperature, filtered to remove most of the salts and the methanol was evaporated under vacuum. The aqueous solution thus obtained was extracted with ethylacetate, dried over sodium sulfate and evaporated to dryness. The residue was subjected to chromatography on silica gel with acetone/hexane (2:1) to give 2.18 g of the product.

MS (ESP): 351.34 (MH⁺) for $C_{15}H_{15}FN_4O_3S$ ¹H-NMR (DMSO-$d_6$) δ: 2.58 (m, 1H); 2.85–3.01 (m, 2H); 3.10–3.16 (m, 1H); 3.40 (dd, 1H); 3.64–3.84 (m, 4H); 4.17 (dd, 1H); 4.93 (m, 1H); 5.85 (m,1H); 7.36 (dd, 1H); 7.41 (dd, 1H); 7.53 (dd, 1H).

EXAMPLE 6

(5R)-3-[4-(1(R,S)-Oxo-3,6-dihydro-2H-thiopyran-4-yl)-3-fluorophenyl]-5-[(4-aminomethyl)-1,2,3-triazol-1-ylmethyl]oxazolidin-2-one

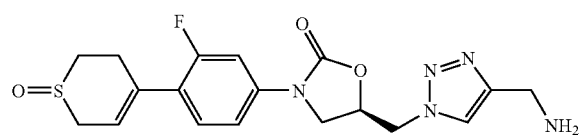

(5R)-3-[4-(1(R,S)-Oxo-3,6-dihydro-2H-thiopyran-4-yl)-3-fluorophenyl]-5-[(4-azidomethyl)-1,2,3-triazol-1-ylmethyl]oxazolidin-2-one (Example 3) (0.718 g, 1.66 mmol) was dissolved in 1,4-dioxane (5 ml) and hydrogenated over Pd/C (10%, wet) at normal pressure and room temperature for 2 days. It was filtered through a 0.45 μM membrane and the solvent was removed under vacuum. Chromatography on silica gel with acetonitrile/water (3:1) gave 0.37 g (55%) of the title compound as a colorless amorphous solid after lyophilization.

MS (ESP): 406.12 (MH⁺) for $C_{18}H_{20}FN_5O_3S$ ¹H-NMR (DMSO-$d_6$) (500 MHz) δ: 2.58 (m, 1H); 2.85–3.00 (m, 2H); 3.10–3.16 (m, 1H); 3.39 (m, 1H); 3.67 (m, 1H); 3.76 (s, 2H); 3.91 (dd, 1H); 4.26 (dd, 1H); 4.80 (m, 2H); 5.15 (m, 1H); 5.84 (m, 1H); 7.30 (dd, 1H); 7.40 (dd, 1H); 7.47 (dd, 1H); 7.96 (s, 1H).

EXAMPLE 7

(5R)-3-[4-(1(R,S)-Oxo-3,6-dihydro-2H-thiopyran-4-yl)-3-fluorophenyl]-5-[(4-(aminocarbonyl)-1,2,3-triazol-1-ylmethyl]oxazolidin-2-one

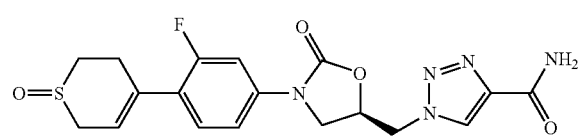

(5R)-3-[4-(1(R,S)-Oxo-3,6-dihydro-2H-thiopyran-4-yl)-3-fluorophenyl]-5-[(4-methoxycarbonyl)-1,2,3-triazol-1-ylmethyl]oxazolidin-2-one (Example 2) (225 mg, 0.52 mmol) was dissolved in ammonia/methanol solution (2M, 5 ml) in a sealed tube. The mixture was stirred for 48 hours and the precipitate formed during the reaction was filtered and washed with ethyl acetate to give the title compound as a colourless solid. Further product was obtained by concentrating the filtrate followed by purification by chromatography on silica gel with 2.5% methanol in dichloromethane to give a combined yield of 148 mg.

MS (ESP): 420.13 (MH⁺) for $C_{18}H_{18}FN_5O_4S$ ¹H-NMR (DMSO-$d_6$) δ: 2.56 (m, 1H); 2.97 (m, 2H); 3.13 (m, 1H); 3.39 (m, 1H); 3.67 (m, 1H); 3.96 (m, 1H); 4.27 (dd, 1H); 4.89 (d, 2H); 5.21 (m, 1H); 5.84 (m, 1H); 7.30 (dd, 1H); 7.41 (t, 1H); 7.47 (dd, 1H); 7.48 (s, 1H); 7.88 (s, 1H); 8.59 (s, 1H).

EXAMPLE 8

(5R)-3-[4-(1(R,S)-Oxo-3,6-dihydro-2H-thiopyran-4-yl)-3-fluorophenyl]-5-[(4-(methoxycarbonyl)aminomethyl)-1,2,3-triazol-1-ylmethyl]oxazolidin-2-one

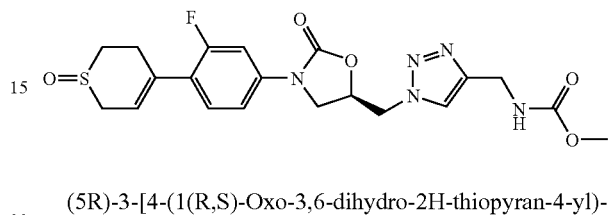

(5R)-3-[4-(1(R,S)-Oxo-3,6-dihydro-2H-thiopyran-4-yl)-3-fluorophenyl]-5-[(4-aminomethyl)-1,2,3-triazol-1-ylmethyl]oxazolidin-2-one (Example 6) (50 mg, 0.12 mmol) was dissolved/suspended in pyridine (0.5 ml), dichloromethane (2 ml) was added and the solution was cooled to −25° C. Methylcarbamylchloride (20 μl, 0.26 mmol) was added and it was stirred for 30 minutes. The reaction was quenched with methanol (3 drops) and solvent was evaporated under vacuum. Chromatography on silica gel with dichloromethane/methanol (12:1) gave 50 mg (87%) of the title compound as a colourless solid.

MS (ESP): 464.16 (MH⁺) for $C_{20}H_{22}FN_5O_5S$ ¹H-NMR (DMSO-$d_6$) (500 MHz) δ: 2.58 (m, 1H); 2.85–3.00 (m, 2H); 3.11–3.15 (m, 1H); 3.38 (m, 1H); 3.56 (s, 3H); 3.67 (m, 1H); 3.90 (dd, 1H); 4.23–4.28 (m, 3H); 4.81 (m, 2H); 5.15 (m, 1H); 5.84 (m, 1H); 7.30 (dd, 1H); 7.40 (dd, 1H); 7.47 (dd, 1H); 7.99 (s, 1H).

EXAMPLE 9

(5R)-3-[4-(1,1-Dioxo-3,6dihydro-2H-thiopyran-4-yl)-3-fluorophenyl]-5-[(4-hydroxymethyl)-1,2,3-triazol-1-yl)methyl]oxazolidin-2-one

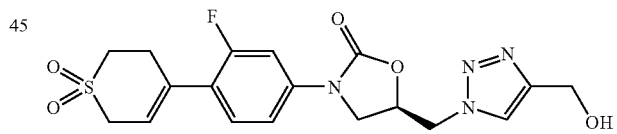

(5R)-3-[4-(1,1-Dioxo-3,6-dihydro-2H-thiopyran-4-yl)-3-fluorophenyl]-5-(azidomethyl) oxazolidin-2-one (Reference Example 2) (15 g, 41 mmol) was dissolved/suspended in 2-(phenylsulfonyl)-2-propene-1-ol (DE 2630947) (12 g, 61 mmol) and N-methylpyrrolidone (NMP, 2 ml) and stirred at 90° C. After 30 minutes more NMP (2 ml) was added and stirred for another 3.5 hours. The partially solidified reaction mixture was taken up in DMF, it was filtered and then concentrated under vacuum. The resulting oil in residual DMF was chromatographed on silica gel with dichloromethane/methanol (16:1) to give 8.64 g (50%) of the title product (TLC: Rf 0.3, chloroform/methanol=6:1) as a colourless solid. The corresponding 5-hydroxymethyl regioisomer was separated during chromatography and presented a minor product (TLC: Rf 0.4, chloroform/methanol=6:1). The structures were assigned based on NOE studies.

MS (ESP): 422.94 (MH+) for C$_{18}$H$_{19}$FN$_4$O$_5$S $^1$H-NMR (DMSO-d$_6$) (500 MHz) δ: 2.98 (m, 2H); 3.28–3.36 (m, 2H); 3.91–3.94 (m, 3H); 4.27 (dd, 1H); 4.54 (d, 2H); 4.82 (d, 2H); 5.16 (m, 1H); 5.23 (dd, 1H); 5.84 (m, 1H); 7.30 (dd, 1H); 7.41 (dd, 1H); 7.50 (dd, 1H); 8.03 (s, 1H).

REFERENCE EXAMPLE 2

(5R)-3-[4-(1,1-Dioxo-3,6-dihydro-2H-thiopyran-4-yl)-3-fluorophenyl]-5-(azidomethyl)oxazolidin-2-one

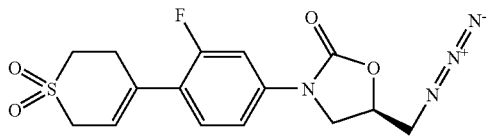

(5R)-3-[4-(3,6-Dihydro-2H-thiopyran-4-yl)-3-fluorophenyl]-5-(azidomethyl)oxazolidin-2-one (WO 01/81350 A1; WO 02/081470 A1) (7 g, 20.9 mmol) was dissolved in dichloromethane (200 ml) and cooled to 0° C. A solution of 3-chloroperbenzoic acid (15.4 g, 70%, 62.9 mmol) was added dropwise. The temperature was allowed to reach room temperature over 2 hours and it was stirred for an additonal 30 minutes at room temperature. The reaction mixture was diluted with ethyl acetate, washed with aqueous sodium thiosulfate solution, then with aqueous sodium hydrogencarbonate solution and with water and dried over sodium sulfate. Chromatography on silica gel with hexanes/acetone (3:2) gave 6.75 g (88%) of the title compound.

MS (ESP): 367.1 (MH+) for C$_{15}$H$_{15}$FN$_4$O$_4$S $^1$H-NMR (DMSO-d) (500 MHz) δ: 2.98 (m, 2H); 3.35–3.40 (m, 2H); 3.71 (dd, 1H); 3.79 (dd, 1H); 3.82 (dd, 1H); 3.93 (m, 2H); 4.17 (dd, 1H); 4.93 (m, 1H); 5.84 (m, 1H); 7.37 (dd, 1H); 7.42 (dd, 1H); 7.54 (dd, 1H).

EXAMPLE 10

(5R)-3-[4-(1,1-Dioxo-3,6-dihydro-2H-thiopyran-4-yl)-3-fluorophenyl]-5-[(4-bromomethyl)-1,2,3-triazol-1-yl)methyl]oxazolidin-2-one

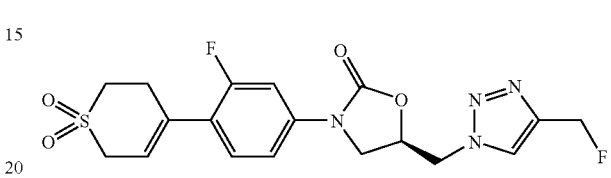

(5R)-3-[4-(1,1-Dioxo-3,6-dihydro-2H-thiopyran-4-yl)-3-fluorophenyl]-5-[(4-hydroxymethyl)-1,2,3-triazol-1-ylmethyl]oxazolidin-2-one (Example 9) (2.05 g, 4.9 mmol) and carbon tetrabromide (1.93 g, 5.8 mmol) were dissolved/suspended in dichloromethane (100 ml) and cooled to 0° C. Triphenylphosphine (2.05 g, 7.8 mmol) was added and the reaction mixture was stirred for 10 minutes at 0° C. then for 20 minutes at room temperature. The reaction mixture was applied onto a silica gel column and product was eluted with hexanes/acetone (1:1). Fractions containing product were pooled, solvent was removed under vacuum and product was precipitated from dichloromethane by addition of hexanes to give the title compound, 1.94 g (82%) as colourless needles.

MS (ESP): 485/457 (MH+) for C$_{18}$H$_{18}$BrFN$_4$O$_4$S $^1$H-NMR (DMSO-d$_6$) (500 MHz) δ: 2.98 (m, 2H); 3.28–3.36 (m, 2H); 3.90–3.94 (m, 3H); 4.28 (dd, 1H); 4.77 (s, 2H); 4.84 (m, 2H); 5.16 (m, 1H); 5.83 (m, 1H); 7.30 (dd, 1H); 7.41 (dd, 1H); 7.47 (dd, 1H); 8.26 (s, 1H).

EXAMPLE 11

(5R)-3-[4-(1,1-Dioxo-3,6-dihydro-2H-thiopyran-4-yl)-3-fluorophenyl]-5-[(4 fluoromethyl)-1,2,3-triazol-1-yl)methyl]oxazolidin-2-one (5R)-3-[4-(1,1-Dioxo-3,6-dihydro-2H-thiopyran-4-yl)-3-fluorophenyl]-5-[(4-bromomethyl)-1,2,3-triazol-1-ylmethyl]oxazolidin-2-one (Example 10) (385 mg, 0.8 mmol) was dissolved in a mixture of 1-butyl-3-methyl-imidazolium tetrafluoroborate (1 ml), acetonitrile (4 ml) and water (90 μl). Potassium fluoride (231 mg, 4 mmol) was added and the reaction mixture was heated to 100° C. for 4 hours. It was diluted with ethylacetate and water, the organic phase was washed with water, diluted with dichloromethane and dried over sodium sulfate. Chromatography on silica gel with dichloromethane/DMF (30:1), followed by precipitation from dichloromethane/methanol gave 86 mg (26%) product as colourless needles.

MS (ESP): 424.9 (MH+) for C$_{18}$H$_{18}$F$_2$N$_4$O$_4$S $^1$H-NMR (DMSO-d$_6$) (300 MHz) δ: 2.95 (m, 2H); 3.28–3.36 (m, 2H); 3.92–3.95 (m, 3H); 4.26 (dd, 1H); 4.85 (d, 2H); 5.16 (m, 1H); 5.47 (d, 2H); 5.82 (m, 1H); 7.27–7.49 (m, 3H); 8.37 (d, 1H).

EXAMPLE 12

(5R)-3-[4-(1,1-Dioxo-3,6-dihydro-2H-thiopyran-4-yl)-3-fluorophenyl]-5-{[4-[(aminomethaneiminium-bromide)thiomethyl]-1,2,3-triazol-1-yl}methyl]oxazolidin-2-one

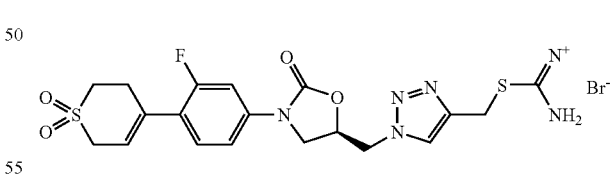

(5R)-3-[4-(1,1-Dioxo-3,6-dihydro-2H-thiopyran-4-yl)-3-fluorophenyl]-5-[(4-bromomethyl)-1,2,3-triazol-1-ylmethyl]oxazolidin-2-one (Example 10) (3.4 g, 7.0 mmol) and thiourea (0.54 g, 7.1 mmol) were refluxed in ethanol (100 ml) for 2 hours under vigorous stirring. The reaction mixture was cooled to room temperature, filtered, washed with ethanol and dried under vacuum to give 3.67 g (93%) of the title compound as a colourless solid.

MS (ESP): 481.26 (M+) for C$_{19}$H$_{22}$FN$_6$O$_4$S$_2$ $^1$H-NMR (DMSO-d$_6$) (500 MHz) δ: 2.94 (m, 2H); 3.29–3.39 (m, 2H); 3.74 (s, 2H); 3.87–3.92 (m, 3H); 4.25 (dd, 1H); 4.56 (s, 2H);

4.83 (d, 2H); 5.13 (m, 1H); 5.81 (m, 1H); 7.27 (dd, 1H); 7.39 (dd, 1H); 7.44 (dd, 1H); 8.16 (s, 1H); 9.01 (brs, 2H); 9.18 (brs, 2H).

EXAMPLE 13

(5R)-3-[4-(1,1-Dioxo-3,6-dihydro-2H-thiopyran-4-yl)-3-fluorophenyl]-5-[4-[(methylthio)methyl]-1,2,3-triazol-1-ylmethyl]oxazolidin-2-one

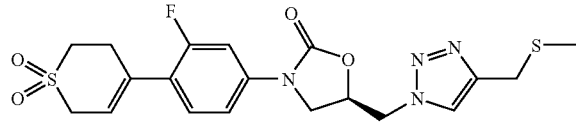

(5R)-3-[4-(1,1-Dioxo-3,6-dihydro-2H-thiopyran-4-yl)-3-fluorophenyl]-5-[4-[(aminomethaneiminiumbromide)thiomethyl]-1,2,3-triazol-1-ylmethyl]oxazolidin-2-one (1 g, 1.78 mmol) (Example 12), methyl iodide (135 μl, 2.17 mmol) and tetrabutylammonium bromide (a few crystals) were vigorously stirred at room temperature for 30 minutes under nitrogen in a mixture of benzene (10 ml) and aqueous sodium hydroxide solution (10 ml, 15%). The reaction mixture was diluted with dichloromethane, washed with 1M aqueous HCl and potassium phosphate buffer (1M, pH 7) and dried over sodium sulfate. Chromatography on silica gel with acetone/hexanes (1.2:1) gave 0.994 g of the title compound as a colourless hard foam.

MS (ESP): 452.98 (MH$^+$) for $C_{19}H_{21}FN_4O_4S_2$ $^1$H-NMR (DMSO-d$_6$) (500 MHz) δ: 2.00 (s, 3H); 2.97 (m, 2H); 3.28–3.39 (m, 2H); 3.74 (s, 2H); 3.90–3.93 (m, 3H); 4.27 (dd, 1H); 4.81 (d, 2H); 5.16 (m, 1H); 5.83 (m, 1H); 7.29 (m, 1H); 7.40 (dd, 1H); 7.45 (m, 1H); 8.05 (s, 1H).

EXAMPLE 14

(5R)-3-[4-(1,1-Dioxo-3,6-dihydro-2H-thiopyran-4-yl)-3-fluorophenyl]-5-[4-[(methylsulfonyl)methyl]-1,2,3-triazol-1-ylmethyl]oxazolidin-2-one

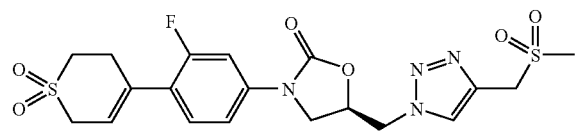

(5R)-3-[4-(1,1-Dioxo-3,6-dihydro-2H-thiopyran-4-yl)-3-fluorophenyl]-5-[[4-[(methylthio)methyl]-1,2,3-triazol-1-yl]methyl]oxazolidin-2-one (Example 13) (0.994 g, 2.2 mmol) was dissolved in dichloromethane (50 ml) and cooled to 0° C. 3-Chloroperbenzoic acid (0.807 g, 70%, 3.3 mmol), dissolved in dichloromethane (20 ml) was added drop wise. The reaction mixture was then stirred for 3 hours at room temperature. It was diluted with ethyl acetate and saturated aqueous sodium hydrogen carbonate solution was added. The resulting precipitate was collected by filtration, washed with sodium hydrogen carbonate solution, water and with ethyl acetate and dried under vacuum to give 0.467 g (44%) of the title compound as a colourless solid.

MS (ESP): 485.23 (MH$^+$) for $C_{19}H_{21}FN_4O_6S_2$ $^1$H-NMR (DMSO-d$_6$) (300 MHz) δ: 2.96 (m, 5H); 3.28–3.40 (m, 2H); 3.90–3.95 (m, 3H); 4.26 (dd, 1H); 4.63 (s, 2H); 4.86 (d, 2H); 5.16 (m, 1H); 5.82 (m, 1H); 7.28–7.50 (m, 3H); 8.24 (s, 1H).

EXAMPLE 15

(5R)-3-[4-(1,1-Dioxo-3,6-dihydro-2H-thiopyran-4-yl)-3-fluorophenyl]-5-[4-[(diphenoxyphosphinyl)oxymethyl]-1,2,3-triazol-1-ylmethyl]oxazolidin-2-one

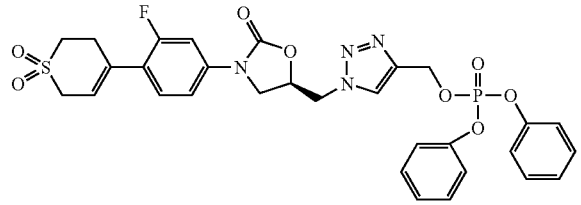

(5R)-3-[4-(1,1-Dioxo-3,6-dihydro-2H-thiopyran-4-yl)-3-fluorophenyl]-5-[(4-hydroxymethyl)-1,2,3-triazol-1-ylmethyl]oxazolidin-2-one (Example 9) (0.66 g, 1.6 mmol) was dissolved/suspended in dichloromethane/pyridine (10 ml, 2:1) and it was cooled to 0° C. Diphenylphosphorochloridate (0.33 ml, 1.6 mmol) dissolved in dichloromethane (2 ml) was added drop wise. The reaction mixture was stirred for 30 minutes at 0° C. and then an additional 60 μl (0.29 mmol) of diphenylphophorochloridate was added via syringe and it was stirred for another hour. It was quenched with phosphate buffer (pH 7), diluted with ethyl acetate and the organic phase was washed with water and dried over sodium sulfate. Chromatography on silica gel with acetone/hexanes (1:1) to give 0.82 g (80%) of the title compound as a hard foam.

MS (ESP): 655.05 (MH$^+$) for $C_{30}H_{28}FN_4O_8PS$ $^1$H-NMR (DMSO-d$_6$) (500 MHz) δ: 2.94 (m, 2H); 3.29–3.34 (m, 2H); 3.90 (m, 3H); 4.12 (s, 2H); 4.24 (dd, 1H); 4.83 (m, 2H); 5.14 (m, 1H); 5.39 (m, 2H); 5.80 (m, 1H); 7.19–7.30 (m, 7H); 7.35–7.47 (m, 6H); 8.30 (s, 1H).

EXAMPLE 16

(5R)-3-[4-(1,1-Dioxo-3,6-dihydro-2H-thiopyran-4-yl)-3-fluorophenyl]-5-[(4-cyanomethyl)-1,2,3-triazol-1-ylmethyl]oxazolidin-2-one

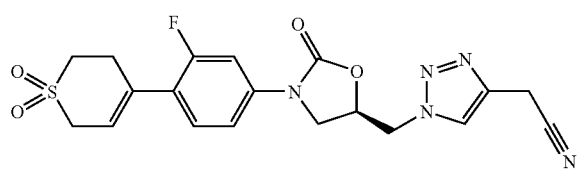

(5R)-3-[4-(1,1-Dioxo-3,6-dihydro-2H-thiopyran-4-yl)-3-fluorophenyl]-5-[(4-[[(diphenoxyphosphinyl)oxy]methyl]-1,2,3-triazol-1-yl)methyl]oxazolidin-2-one (Example 15) (0.5 g, 0.76 mmol) and sodium cyanide (0.22 g, 4.5 mmol) were dissolved/suspended in DMF (10 ml) and it was heated to 60° C. for 1.5 hours. It was diluted with ethyl acetate, washed with potassium phosphate buffer (pH 7) and with water, and dried over sodium sulfate. Chromatography on silica gel with acetone/hexanes (1:1) gave 236 mg (72%) of the title compound as a colourless solid.

MS (ESP): 432.07 (MH⁺) for $C_{19}H_{18}FN_5O_4S$ ¹H-NMR (DMSO-d₆) (500 MHz) δ: 2.94 (m, 2H); 3.30–3.34 (m, 2H); 3.88–3.90 (m, 3H); 4.12 (s, 2H); 4.24 (dd, 1H); 4.82 (d, 2H); 5.14 (m, 1H); 5.81 (m, 1H); 7.28 (dd, 1H); 7.38 (dd, 1H); 7.45 (dd, 1H); 8.16 (s, 1H).

EXAMPLE 17

(5R)-3-[4-(1,1-Dioxo-3,6-dihydro-2H-thiopyran-4-yl)-3-fluorophenyl]-5-[(4-chloromethyl)-1,2,3-triazol-1-ylmethyl]oxazolidin-2-one

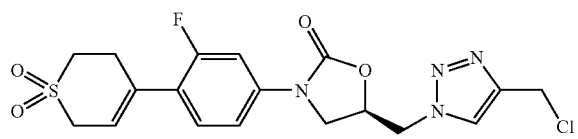

(5R)-3-[4-(1,1-Dioxo-3,6-dihydro-2H-thiopyran-4-yl)-3-fluorophenyl]-5-[(4-hydroxymethyl)-1,2,3-triazol-1-ylmethyl]oxazolidin-2-one (Example 9) (0.65 g, 1.6 mmol) was dissolved/suspended in dichloromethane/pyridine (10 ml, 2:1) and reacted with diphenylphosphorochloridate (1 ml, 4.8 mmol) as described for Example 15. The solvent was removed under vacuum, the residue taken up in DMF (10 ml) and sodium cyanide was added (5 fold excess, in an attempt to make the cyanide). The reaction mixture was heated at 60° C. for 30 minutes and then at 80° C. for one hour. It was diluted with ethyl acetate, washed with water and dried over sodium sulfate. Chromatography on silica gel with hexanes/acetone (1:1) gave 0.29 g (66%) of the title compound as a colourless solid.

MS (ESP): 441.02 (MH⁺) for $C_{18}H_{18}ClFN_4O_4S$ ¹H-NMR (DMSO-d₆) (500 MHz) δ: 2.98 (m, 2H); 3.29–3.37 (m, 2H); 3.90–3.95 (m, 3H); 4.28 (dd, 1H); 4.84–4.87 (m, 4H); 5.17 (m, 1H); 5.84 (m, 1H); 7.30 (m, 1H); 7.41 (dd, 1H); 7.47 (m, 1H); 8.27 (s, 1H).

EXAMPLE 18

(5R)-3-[4-(1,1-Dioxo-tetrahydro-2H-thiopyran-4-yl)-3-fluorophenyl]-5-[(4-hydroxymethyl)-1,2,3-triazol-1-ylmethyl]oxazolidin-2-one

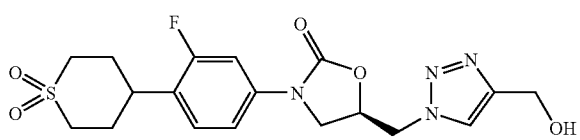

(5R)-3-[4-(1,1-Dioxo-3,6-dihydro-2H-thiopyran-4-yl)-3-fluorophenyl]-5-(azidomethyl) oxazolidin-2-one (0.8 g, 2.2 mmol) (Reference Example 2) and tetrahydro-2-(2-propynyloxy)-2H-pyran (1.3 ml, 9.2 mmol) were refluxed in toluene (5 ml) overnight. The solvent was evaporated and the residue was filtered over silica gel with dichloromethane/methanol (20:1) as eluant to give the crude 4- and 5-substituted triazoles in 1:1 ratio. This mixture was dissolved in tetrahydrofuran/methanol (2:1, 20 ml), acetic acid was added (5 drops) and it was hydrogenated over Pd/C (10%) at normal pressure and room temperature for two days. It was filtered through a 0.45 μM membrane and solvent was removed under vacuum. Chromatography on silica gel with dichloromethane/methanol (20:1) gave 176 mg (19%) of the title compound as a colourless solid.

MS (ESP): 425.12 (MH⁺) for $C_{18}H_{21}FN_4O_5S$ ¹H-NMR (DMSO-d₆) (500 MHz) δ: 2.06 (m, 2H); 2.17 (m, 2H); 3.12 (m, 2H); 3.22 (m, 1H); 3.39 (m, 2H); 3.89 (dd, 1H); 4.25 (dd, 1H); 4.53 (d, 2H); 4.80 (d, 2H); 5.14 (m, 1H); 5.23 (dd, 1H); 5.84 (m, 1H); 7.26 (dd, 1H); 7.39 (dd, 1H); 7.45 (dd, 1H); 8.03 (s, 1H). 4-Substitution on the triazole moiety was confirmed by NOE studies.

EXAMPLE 19

(5R)-3-[4-(1,1-Dioxo-3,6-dihydro-2H-thiopyran-4-yl)-3-fluorophenyl]-5-[4-(1H-1,2,3-triazol-4-ylthiomethyl)-1,2,3-triazol-1-ylmethyl]oxazolidin-2-one (5R)-3-[4-(1,1-Dioxo-3,6-dihydro-2H-thiopyran-4-yl)-3-fluorophenyl]-5-[(4-bromomethyl)-1,2,3-triazol-1-ylmethyl]oxazolidin-2-one (Example 10) (211 mg, 0.44 mmol) and 1H-1,2,3-triazole-4-thiol, sodium salt, (80 mg, 0.65 mmol) were dissolved in DMF (2 ml) and left overnight at room temperature. DMF was removed under vacuum. Chromatography on silica gel with dichloromethane/methanol (15:1) gave 170 mg (77%) of the title compound as a colourless solid.

MS (ESP): 505.92 (MH⁺) for $C_{20}H_{20}FN_7O_4S_2$ ¹H-NMR (DMSO-d₆) (500 MHz) δ: 2.97 (m, 2H); 3.30–3.45 (m, 2H, under HDO); 3.74 (s, 2H); 3.87–3.93 (m, 3H); 4.22–4.27 (m, 3H); 4.79 (d, 2H); 5.13 (m, 1H); 5.83 (m, 1H); 7.29 (dd, 1H); 7.40 (dd, 1H); 7.47 (dd, 1H); 7.88 (s, 1H); 8.00 (s, 1H).

EXAMPLE 20

(5R)-3-[4-(1,1-Dioxo-3,6-dihydro-2H-thiopyran-4-yl)-3-fluorophenyl]-5-[4-[(1H-imidazol-2-ylthio)methyl]-1,2,3-triazol-1-ylmethyl]oxazolidin-2-one (5R)-3-[4-(1,1-Dioxo-3,6-dihydro-2H-thiopyran-4-yl)-3-fluorophenyl]-5-[4-[(diphenoxyphosphinyl)oxymethyl]-1,2,3-triazol-1-ylmethyl]oxazolidin-2-one (Example 15) (0.125 g, 0.19 mmol) was added to a solution of 2-mercaptoimidazole (38 mg, 0.38 mmol) in DMF (2 ml) and the resulting solution was added to a suspension of sodium hydride (15 mg, 0.38 mmol) in DMF (2 ml). The reaction mixture was stirred for 30 minutes and then quenched with excess of aqueous sodium bicarbonate. The mixture was extracted with ethyl acetate, was washed with sodium bicarbonate, water and brine, dried over sodium sulfate and concentrated in vacuo to give 40 mg (42%) of the title compound as a colourless solid.

MS (ESP): 505.10 (MH+) for C$_{21}$H$_{21}$FN$_6$O$_4$S$_2$ $^1$H-NMR (DMSO-d$_6$) δ: 12.12 (brs, 1H); 7.91 (s, 1H); 7.48 (m, 2H); 7.29 (m, 1H); 7.05 (brs, 2H); 5.77 (s, 1H); 5.10 (m, 1H); 4.77 (d, 2H); 4.29 (s, 2H); 4.24 (dd, 1H); 3.87 (m, 3H); 3.3 (m, 2H); 2.95 (s, 2H).

EXAMPLE 21

(5R)-3-[4-(1,1-Dioxo-3,6-dihydro-2H-thiopyran-4-yl)-3-fluorophenyl]-5-[4-[(phenylmethyl)thiomethyl]-1,2,3-triazol-1-ylmethyl]oxazolidin-2-one

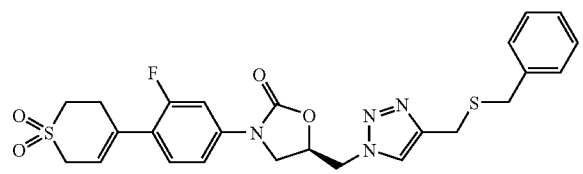

Sodium hydride (30 mg, 0.76 mmol) was suspended in DMF (10 ml), thiophenol (0.09 ml, 0.76 mmol) was added, followed by addition of (5R)-3-[4-(1,1-dioxo-3,6-dihydro-2H-thiopyran-4-yl)-3-fluorophenyl]-5-[4-[(diphenoxyphosphinyl)oxymethyl]-1,2,3-triazol-1-ylmethyl]oxazolidin-2-one (Example 15) (250 mg, 0.38 mmol). The reaction mixture was stirred for 5 hours, then quenched with sodium bicarbonate solution, diluted with ethyl acetate, washed with water and brine, dried over sodium sulfate and concentrated in vacuo. Chromatography on silica gel with 2.5% methanol in dichloromethane gave the title compound as an off-white solid (29 mg).

MS (ESP): 529.08 (M+H+) for C$_{25}$H$_{25}$FN$_4$O$_4$S$_2$ $^1$H-NMR (CDCl$_3$) δ: 7.60 (s, 1H); 7.23 (m, 8H); 5.74 (m, 1H); 5.05 (m, 1H); 4.73 (d, 2H); 4.17 (t, 1H); 4.02 (m, 1H); 3.80 (s, 2H); 3.66 (m, 4H) 3.24 (m, 2H); 3.07 (m, 2H).

EXAMPLE 22

(5R)-3-[4-(1,1-Dioxo-3,6-dihydro-2H-thiopyran-4-yl)-3-fluorophenyl]-5-[4-(dimethylamino)methyl-1,2,3-triazol-1-ylmethyl]oxazolidin-2-one

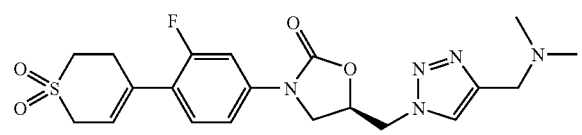

(5R)-3-[4-(1,1-Dioxo-3,6-dihydro-2H-thiopyran-4-yl)-3-fluorophenyl]-5-[(4-bromomethyl)-1,2,3-triazol-1-ylmethyl]oxazolidin-2-one (Example 10) (250 mg, 0.52 mmol) was dissolved in DMF (1.5 ml) and dimethylamine (in water, 40%, 250 μl, 2.2 mmol) was added. The mixture was heated to 50° C. for 30 minutes. Triethylamine (1 ml) was added and solvent was removed under vacuum. Chromatography on silica gel with acetonitrile/water (5:1 to 3:1) gave 90 mg (39%) of the title compound as a colourless solid.

MS (ESP): 450.27 (MH+) for C$_{20}$H$_{24}$FN$_5$O$_4$S $^1$H-NMR (DMSO-d$_6$) (500 MHz) δ: 2.09 (s, 6H); 2.96 (m, 2H); 3.30–3.39 (m, 2H); 3.48 (s, 2H); 3.90–3.93 (m, 3H); 4.26 (dd, 1H); 4.78–4.85 (m, 2H); 5.17 (m, 1H); 5.83 (m, 1H); 7.27 (dd, 1H); 7.39 (dd, 1H); 7.44 (dd, 1H); 8.02 (s, 1H).

EXAMPLE 23

(5R)-3-[4-(1,1-Dioxo-3,6-dihydro-2H-thiopyran-4-yl)-3-fluorophenyl]-5-[4-carboxaldehyde-1,2,3-triazol-1-ylmethyl]oxazolidin-2-one

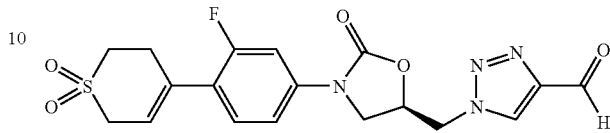

Oxalylchloride (1.36 ml, 15.6 mmol) in dichloromethane (30 ml) was cooled to −50° C. DMSO (1.42 mL, 20 mmol) in dichloromethane (30 ml) was added drop wise under stirring. The reaction mixture was stirred for 10 minutes and (5R)-3-[4-(1,1-dioxo-3,6-dihydro-2H-thiopyran-4-yl)-3-fluorophenyl]-5-[(4-hydroxymethyl)-1,2,3-triazol-1-ylmethyl]oxazolidin-2-one (Example 9) (5 g, 11.8 mmol), (dissolved in N-methylpyrrolidone (25 ml) and then diluted with dichloromethane (25 ml)) was added drop wise and the resulting mixture vigorously stirred for 1 hour. N,N-Diisopropylethylamine (10 ml, 57.4 mmol) was added dropwise, the reaction mixture was warmed to −40° C. and then stirred for another hour. The reaction mixture was then slowly allowed to warm to −20° C. and held at this temperature over night. The homogeneous solution was directly applied onto a silica gel column and eluted with hexanes/acetone (1:1 to 1:2). Fractions containing product were pooled and concentrated under vacuum. The product was then precipitated from acetone (100 ml) by the addition of hexanes (700 ml) to give 4.2 g (84%) of the title compound as a colourless solid.

MS (ESP): 419.29 (M−H−) for C$_{18}$H$_{17}$FN$_4$O$_5$S $^1$H-NMR (DMSO-d$_6$) (500 MHz) δ: 2.98 (m, 2H); 3.29–3.38 (m, 2H); 3.93 (s, 2H); 3.97 (dd, 1H); 4.29 (dd, 1H); 4.94 (d, 2H); 5.22 (m, 1H); 5.84 (m, 1H); 7.32 (dd, 1H); 7.42 (dd, 1H); 7.48 (dd, 1H); 8.95 (s, 1H); 10.05 (s, 1H).

EXAMPLE 24

(5R)-3-[4-(1,1-Dioxo-3,6-dihydro-2H-thiopyran-4-yl)-3-fluorophenyl]-5-[4-(difluoromethyl)-1,2,3-triazol-1-ylmethyl]oxazolidin-2-one

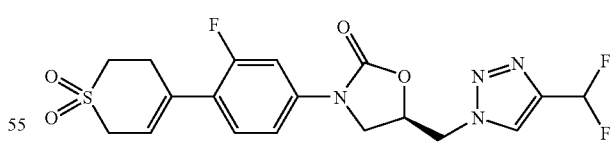

(5R)-3-[4-(1,1-Dioxo-3,6-dihydro-2H-thiopyran-4-yl)-3-fluorophenyl]-5-[4-carboxaldehyde-1,2,3-triazol-1-ylmethyl]oxazolidin-2-one (Example 23) (100 mg, 0.24 mmol) was dissolved/suspended in dichloromethane (10 ml). [Bis (2-methoxyethyl)amino]sulfur trifluoride (71 μl, 0.39 mmol) and a catalytic amount of ethanol (1.3 μl) were added and the mixture was refluxed under stirring for 36 hours. The reaction mixture was loaded onto a silica gel column and eluted with hexanes/acetone (−1.25:1) to give 38 mg (36%) of the title compound as a colourless solid.

MS (ESP): 443 (MH$^+$) for C$_{18}$H$_{17}$F$_3$N$_4$O$_4$S $^1$H-NMR (DMSO-d$_6$) (300 MHz) δ: 2.98 (m, 2H); 3.31–3.37 (m, 2H); 3.93 (brs, 2H); 3.94 (dd, 1H); 4.29 (dd, 1H); 4.91 (d, 2H); 5.20 (m, 1H); 5.84 (m, 1H); 7.25 (dd, 1H); 7.31 (dd, 1H); 7.41 (dd, 1H); 7.47 (dd, 1H); 8.61 (m, 1H).

EXAMPLE 25

(5R)-3-[4-(1,1-Dioxo-3,6-dihydro-2H-thiopyran-4-yl)-3-fluorophenyl]-5-[4-(2,2-dibromoethenyl)-1,2,3-triazol-1-ylmethyl]oxazolidin-2-one

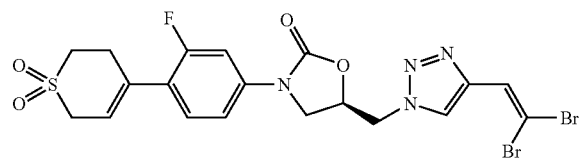

(5R)-3-[4-(1,1-Dioxo-3,6-dihydro-2H-thiopyran-4-yl)-3-fluorophenyl]-5-[4-carboxaldehyde-1,2,3-triazol-1-ylmethyl]oxazolidin-2-one (Example 23) (5 g, 11.9 mmol) and carbon tetrabromide (4.34 g, 13.1 mmol) were dissolved/suspended in dichloromethane (100 ml) and it was cooled to 0° C. Triphenylphosphine (6.55 g, 25 mmol) was added and it was stirred for 30 minutes at 0° C. and then for 1 hour at room temperature. The reaction mixture was applied onto a silica gel column and it was eluted with toluene/ethanol (10:1 to 7:1) to give 6.1 g (89%) of the title compound as an off-white solid.

MS (ESP): 575, 577, 579 (MH$^+$) for C$_{19}$H$_{17}$Br$_2$FN$_4$O$_4$S $^1$H-NMR (DMSO-d$_6$) (500 MHz) δ: 2.98 (m, 2H); 3.31–3.40 (m, 2H); 3.93–3.96 (m, 3H); 4.28 (dd, 1H); 4.90 (d, 2H); 5.21 (m, 1H); 5.85 (m, 1H); 7.31 (dd, 1H); 7.42 (dd, 1H); 7.47 (dd, 1H); 7.80 (s, 1H); 8.68 (s, 1H).

EXAMPLE 26

(5R)-3-[4-(1,1-Dioxo-3,6-dihydro-2H-thiopyran-4-yl)-3-fuorophenyl]-5-[4-(2-(3-methyl-5-isoxazolyl)ethynyl)-1,2,3-triazol-1-ylmethyl]oxazolidin-2-one

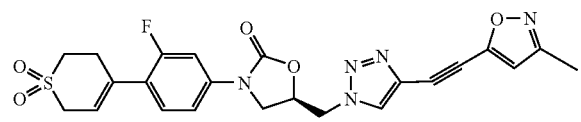

(5R)-3-[4-(1,1-Dioxo-3,6-dihydro-2H-thiopyran-4-yl)-3-fluorophenyl]-5-[4-(2,2-dibromoethenyl)-1,2,3-triazol-1-ylmethyl]oxazolidin-2-one (Example 25) (0.6 g, 1.04 mmol), 3-methyl-5-(tributylstannyl)-isoxazole (407 mg, 1.09 mmol) [Sakamoto, T. et al., *Condensed Heteroaromatic Ring Systems. XIX. Synthesis and Reactions of 5-(Tributylstannyl) isoxazoles. Tetrahedron*, 47, 28, 5111–5118] and tris(2-furyl)phosphine (37 mg, 0.16 mmol) were dissolved in DMF (2.5 ml). Diisopropylethyl amine (0.272 ml, 1.56 mmol) was added, the reaction mixture was flushed with argon and tris(dibenzylideneacetone)dipalladium (0) (30 mg, 0.03 mmol) was added. The mixture was heated to 85° C. for 20 hours under argon. The solvent was removed under vacuum. Chromatography on silica gel with dichloromethane/DMF (30:1) gave 30 mg (6%) of the title compound as a colourless solid.

MS (ESP): 497.91 (MH$^+$) for C$_{23}$H$_{20}$FN$_5$O$_5$S $^1$H-NMR (DMSO-d$_6$) (300 MHz) δ: 2.30 (s, 3H); 2.95 (m, 2H); 3.30–3.44 (m, 2H); 3.88–3.97 (m, 3H); 4.27 (dd, 1H); 4.90 (d, 2H); 5.19 (m, 1H); 5.82 (m, 1H); 6.94 (s, 1H); 7.29 (dd, 1H); 7.40 (dd, 1H); 7.45 (dd, 1H); 8.78 (s, 1H).

EXAMPLE 27

(5R)-3-[4-(1,1-Dioxo-3,6-dihydro-2H-thiopyran-4-yl)-3-fluorophenyl]-5-[(4-(3-buten-1-ynyl)-1,2,3-triazol-1-yl)methyl]oxazolidin-2-one

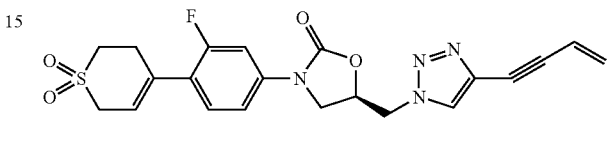

(5R)-3-[4-(1,1-Dioxo-3,6-dihydro-2H-thiopyran-4-yl)-3-fluorophenyl]-5-[4-(2,2-dibromoethenyl)-1,2,3-triazol-1-ylmethyl]oxazolidin-2-one (Example 25) (0.3 g, 0.52 mmol), allyl tributyl tin (160 μl, 0.55 mmol) and tris(4-methoxyphenyl)phosphine (28 mg, 0.08 mmol) were dissolved in DMF (2.5 ml). Diisopropylethyl amine (136 μl, 0.78 mmol) was added, the reaction mixture was flushed with argon and tris(dibenzylideneacetone)dipalladium (0) (15 mg, 0.01 mmol) was added. The mixture was heated to 80° C. for 10 hours under argon. It was diluted with ethyl acetate, washed with phosphate buffer (pH 7), saturated aqueous potassium fluoride solution and with water and dried over sodium sulfate. Chromatography on silica gel with chloroform/methanol (15:1) gave 32 mg (14%) of the title compound as a colourless solid.

MS (ESP): 442.97 (MH$^+$) for C$_{21}$H$_{19}$FN$_4$O$_4$S $^1$H-NMR (DMSO-d$_6$) (300 MHz) δ: 2.95 (m, 2H); 3.29–3.43 (m, 2H); 3.89–3.95 (m, 3H); 4.25 (dd, 1H); 4.84 (d, 2H); 5.17 (m, 1H); 5.70 (dd, 1H); 5.80 (dd, 1H); 5.82 (m, 1H); 6.16 (dd, 1H); 7.29 (dd, 1H); 7.40 (dd, 1H); 7.45 (dd, 1H); 8.50 (s, 1H).

EXAMPLE 28

(5R)-3-[4-(1,1-Dioxo-3,6-dihydro-2H-thiopyran-4-yl)-3-fluorophenyl]-5-[4-((E)-2-bromoethenyl)-1,2,3-triazol-1-ylmethyl]oxazolidin-2-one

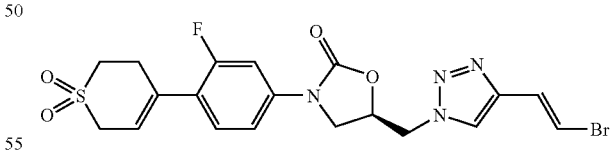

(5R)-3-[4-(1,1-Dioxo-3,6-dihydro-2H-thiopyran-4-yl)-3-fluorophenyl]-5-[4-(2,2-dibromoethenyl)-1,2,3-triazol-1-ylmethyl]oxazolidin-2-one (0.4 g, 0.69 mmol) was dissolved/supended in ethanol (2 ml) and diethylphosphite (0.36 ml, 2.79 mmol). Triethylamine (0.195 ml, 1.39 mmol) was added and the reaction mixture heated under vigorous stirring at 90° C. for 5 hours. It was cooled to room temperature, diluted with dichloromethane, washed with phosphate buffer (pH 7) and dried over sodium sulfate. Chromatography on silica gel with dichloromethane/DMF (50:1 to 40:1) gave 151 mg (44%) of the title compound as a colourless solid.

MS (ESP): 537.7/539.9 (MH$^+$+41 (acetonitrile)) for C$_{19}$H$_{18}$BrFN$_4$O$_4$S $^1$H-NMR (CD$_3$CN) (500 MHz) δ: 3.04 (m, 2H); 3.23–3.28 (m, 2H); 3.81 (brs, 2H); 3.87 (dd, 1H); 4.22 (dd, 1H); 4.72 (dd, 1H); 4.78 (dd, 1H); 5.10 (m, 1H); 5.82 (m, 1H); 7.09 (d, 1H); 7.15 (d, 1H); 7.20 (dd, 1H); 7.33 (dd, 1H); 7.37 (dd, 1H); 7.97 (s, 1H).

EXAMPLE 29

(5R)-3-[4-(1,1-Dioxo-3,6-dihydro-2H-thiopyran-4-yl)-3-fluorophenyl]-5-[4-(2-bromoethynyl)-1,2,3-triazol-1-ylmethyl]oxazolidin-2-one

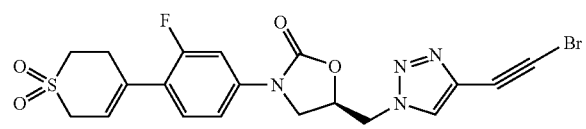

(5R)-3-[4-(1,1-Dioxo-3,6-dihydro-2H-thiopyran-4-yl)-3-fluorophenyl]-5-[4-(2,2-dibromoethenyl)-1,2,3-triazol-1-ylmethyl]oxazolidin-2-one (Example 25) (0.5 g, 0.87 mmol) was dissolved in DMSO (87 ml) and cooled to 15° C. 1,8-Diazabicyclo[5.4.0]undec-7-ene (DBU) (0.262 ml, 1.75 mmol), dissolved in DMSO (1.7 ml), was added drop wise under stirring over 30 minutes. The temperature was maintained at 15–18° C. and after 6 hours more DBU (0.125 ml, 0.83 mmol) was added drop wise via a syringe and the resulting solution stirred for another 30 minutes. The reaction was quenched with cold aqueous HCl (0.5 M), extracted with dichloromethane, washed with water and dried over sodium sulfate. Chromatography on silica gel with hexanes/acetone (1.5:1 to 1:1) gave 108 mg (25%) of the title product as a colourless solid.

MS (APCI, Pos.): 495/497 (MH$^+$) for C$_{19}$H$_{16}$BrFN$_4$O$_4$S $^1$H-NMR (DMSO-d$_6$) (500 MHz) δ: 2.97 (m, 2H); 3.33–3.40 (m, 2H); 3.90–3.95 (m, 3H); 4.26 (dd, 1H); 4.86 (d, 2H); 5.17 (m, 1H); 5.84 (m, 1H); 6.16 (dd, 1H); 7.31 (dd, 1H); 7.41 (dd, 1H); 7.46 (dd, 1H); 8.55 (s, 1H).

EXAMPLE 30

(5R)-3-[4-(1,1-Dioxo-3,6-dihydro-2H-thiopyran-4-yl)-3-fluorophenyl]-5-[4-(2-(ethylmethylamino)-2-oxoethyl)-1,2,3-triazol-1-ylmethyl]oxazolidin-2-one

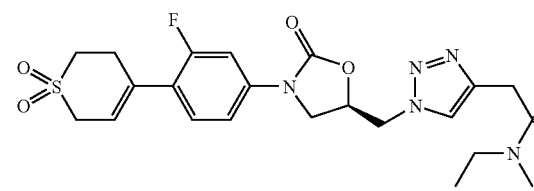

(5R)-3-[4-(1,1-Dioxo-3,6-dihydro-2H-thiopyran-4-yl)-3-fluorophenyl]-5-[4-(2,2-dibromoethenyl)-1,2,3-triazol-1-ylmethyl]oxazolidin-2-one (Example 25) (0.25 g, 0.43 mmol) was dissolved in DMF (1.5 ml). Ethylmethylamine (0.186 ml, 2.16 mmol) and water (0.5 ml) were added and the reaction mixture was heated for 2 hours to 90° C. More ethylmethylamine (0.2 ml, 2.33 mmol) was added and it was heated for another 1.5 hours. The reaction mixture was cooled to room temperature and the solvent was removed under vacuum. Chromatography on silica gel with toluene/ethanol (5:1) and then with hexanes/acetone (1:2) gave 27 mg (13%) of the title compound as a colourless solid.

MS (ESP): 492.34 (MH$^+$) for C$_{22}$H$_{26}$FN$_5$O$_5$S $^1$H-NMR (DMSO-d$_6$) (500 MHz) δ: 1.01 and 1.08 (2×dd, 3H); 2.81 and 3.00 (2×s, 3H); 2.97 (m, 2H); 3.29–3.45 (m, 4H); 3.75 and 3.77 (2×s, 2H); 3.89–3.93 (m, 3H); 4.26 (dd, 1H); 4.81 (d, 2H); 5.16 (m, 1H); 5.83 (m, 1H); 7.30 (dd, 1H); 7.41 (dd, 1H); 7.47 (dd, 1H); 7.99 and 8.01 (2×s, 1H).

EXAMPLE 31

(5R)-3-[4-(1,1-Dioxo-3,6-dihydro-2H-thiopyran-4-yl)-3-fluorophenyl]-5-[(4-(2-(dimethylamino)-2-oxoethyl)-1,2,3-triazol-1-yl)methyl]oxazolidin-2-one

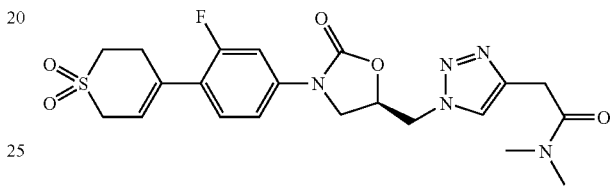

(5R)-3-[4-(1,1-Dioxo-3,6-dihydro-2H-thiopyran-4-yl)-3-fluorophenyl]-5-[4-(2,2-dibromoethenyl)-1,2,3-triazol-1-ylmethyl]oxazolidin-2-one (Example 25) (0.25 g, 0.43 mmol) was dissolved in DMF (1.5 ml). Dimethylamine (0.250 ml, 40% in water, 2.2 mmol) and water (0.25 ml) were added and the reaction mixture was heated for 3 hours to 90° C. It was cooled to room temperature and the solvent was removed under vacuum. Chromatography on silica gel with dichloromethane/methanol (20:1) gave 74 mg (36%) of the title compound as a colourless solid.

MS (ESP): 478.29 (MH$^+$) for C$_{21}$H$_{24}$FN$_5$O$_5$S $^1$H-NMR (DMSO-D$_6$) (500 MHz) δ: 2.84 (s, 3H); 2.97 (m, 2H); 3.03 (s, 3H); 3.29–3.43 (m, 2H); 3.77 (s, 2H); 3.89–3.93 (m, 3H); 4.26 (dd, 1H); 4.81 (d, 2H); 5.16 (m, 1H); 5.84 (m, 1H); 7.30 (dd, 1H); 7.41 (dd, 1H); 7.48 (dd, 1H); 8.00 (s, 1H).

EXAMPLE 32

(5R)-3-[4-(1,1-Dioxo-3,6-dihydro-2H-thiopyran-4-yl)-3-fluorophenyl]-5-[4-(ethylaminocarbonyloxymethyl)-1,2,3-triazol-1-ylmethyl]oxazolidin-2-one

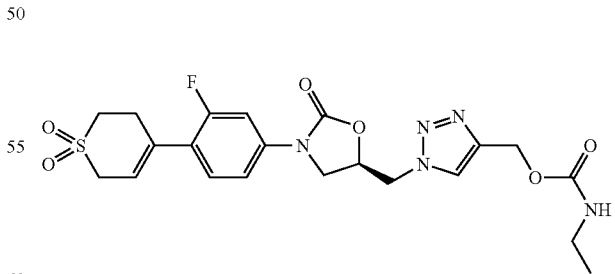

(5R)-3-[4-(1,1-Dioxo-3,6-dihydro-2H-thiopyran-4-yl)-3-fluorophenyl]-5-[(4-hydroxymethyl)-1,2,3-triazol-1-ylmethyl]oxazolidin-2-one (Example 9) (150 mg, 0.36 mmol) was dissolved in pyridine (2 ml), ethylisocyanate (234 mg, 3.6 mmol) was added and the resulting mixture was stirred for 4 hours at 90° C. It was cooled to room temperature, the solvent was removed under vacuum and the residue was purified by flash chromatography on silica gel with 5% of methanol in dichloromethane to give the title product (170 mg).

MS (ESP): 494.21 (MH$^+$) for $C_{21}H_{24}FN_5O_6S$ $^1$H-NMR (DMSO-d$_6$) δ: 1.00 (t, 3H); 2.96 (m, 2H); 3.00 (m, 2H); 3.34 (m, 2H); 3.91 (m, 3H); 4.25 (dd, 1H); 4.83 (d, 2H); 5.04 (s, 2H); 5.14 (m, 1H); 5.82 (m, 1H); 7.18 (m, 1H); 7.27 (m, 1H); 7.40 (m, 1H); 7.48 (m, 1H); 8.16 (s, 1H).

EXAMPLE 33

(5R)-3-[4-(1,1-Dioxo-3,6-dihydro-2H-thiopyran-4-yl)-3-fluorophenyl]-5-[4-amino)-1,2,3-triazol-1-ylmethyl]oxazolidin-2-one

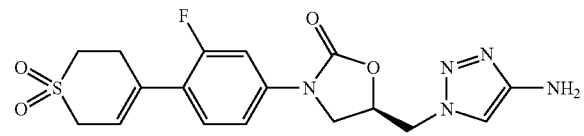

A mixture of (5R)-3-[4-(1,1-Dioxo-3,6-dihydro-2H-thiopyran-4-yl)-3-fluorophenyl]-5-[4-carboxy)-1,2,3-triazol-1-ylmethyl]oxazolidin-2-one (Reference Example 3) (873 mg, 2.0 mmol), triethylamine (222 mg, 2.2 mmol) and t-butanol (10 ml) were heated to 70° C. with vigrous stirring. Diphenylphosphoryl azide (608 mg, 2.2 mmol) was added drop wise and the resulting mixture was refluxed for 12 hours. The solvent was evaporated, the residue was dissolved in dichloromethane (6 ml) and methanol (0.5 ml), hexane (20 ml) was added and the resulting precipitate was filtered to give a white solid (900 mg). This product (160 mg) was stirred in a mixture of dry dichloromethane (3 ml) and trifluoroacetic acid (3 ml) for 1 hour at room temperature. The solvent and excess of trifluoroacetic acid were removed under vacuum and the residue was purified by reverse phase chromatography with 5%~95% acetonitrile in water (containing 0.1% TFA) to give the title product (70 mg).

MS (ESP): 408.21 (MH$^+$) for $C_{17}H_{18}FN_5O_4S$ $^1$H-NMR (DMSO-d$_6$) δ: 2.96 (m, 2H); 3.43 (m, 2H); 3.90 (m, 3H); 4.23 (dd, 1H); 4.68 (d, 2H); 5.12 (m, 1H); 5.77 (m, 1H); 7.27 (m, 1H); 7.38 (m, 1H); 7.45 (m, 1H); 7.62 (s, 1H); (NH$_2$ not observed due to exchange).

The intermediate for this example was prepared as follows:

Intermediate 3

(5R)-3-[4-(1,1-Dioxo-3,6-dihydro-2H-thiopyran-4-yl)-3-fluorophenyl]-5-[(4-carboxy)-1,2,3-triazol-1-ylmethyl]oxazolidin-2-one

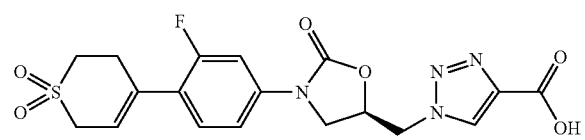

(5R)-3-[4-(1,1-Dioxo-3,6-dihydro-2H-thiopyran-4-yl)-3-fluorophenyl]-5-(azidomethyl)oxazolidin-2-one (6.9 g, 18.83 mmol) (Reference Example 2) was dissolved in dry 1,4-dioxane (15 ml), 2-propynoic acid t-butylester (4.75 g, 37.67 mmol) was added and the resulting mixture was refluxed for 12 hours under vigorous stirring. Ethyl acetate (30 ml) was added and the resulting precipitate was filtered, washed with ethyl acetate and dried as a white solid (5 g). This solid was suspended in dichloromethane (16 ml), followed by drop wise addition of trifluoroacetic acid (8 ml) and the resulting mixture was stirred over night. The solvent was removed under vacuum and the residue was purified by precipitation from dichloromethane to give the title product as an off-white solid (3.3 g).

MS (ESP): 435.25 (M–H$^-$) for $C_{18}H_{17}FN_4O_6S$ $^1$H-NMR (DMSO-d$_6$) δ: 2.89 (m, 2H); 3.31 (m, 2H); 3.84 (m, 2H); 3.88 (m, 1H); 4.19 (dd, 1H); 4.80 (d, 2H); 5.12 (m, 1H); 5.75 (m, 1H); 7.22 (m, 1H); 7.32 (m, 1H); 7.40 (m, 1H); 8.66 (s, 1H); 13.11 (br, 1H).

EXAMPLE 34

(5R)-3-[4-(1,1-Dioxo-3,6-dihydro-2H-thiopyran-4-yl)-3-fluorophenyl]-5-[(4-acetylamino)-1,2,3-triazol-1-yl)methyl]oxazolidin-2-one

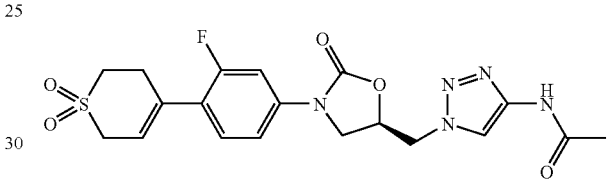

(5R)-3-[4-(1,1-Dioxo-3,6-dihydro-2H-thiopyran-4-yl)-3-fluorophenyl]-5-[(4-amino)-1,2,3-triazol-1-ylmethyl]oxazolidin-2-one (Example 33) (23 mg, 0.057 mmol) was dissolved in pyridine/dichloromethane (1:1, 5 ml). Acetyl chloride (22 mg, 5 eq.) was added and the resulting mixture was stirred at room temperature for 24 hours. The solvent was removed under vaccum and the residure was purified by flash chromatography on silica gel with 5% methanol in dichloromethane to give the title product (25 mg).

MS (ESP): 450.27 (MH$^+$) for $C_{19}H_{20}FN_5O_5S$ $^1$H-NMR (DMSO-d$_6$) δ: 2.04 (s, 3H); 2.96 (m, 2H); 3.43 (m, 2H); 3.90 (m, 3H); 4.23 (dd, 1H); 4.73 (d, 2H); 5.12 (m, 1H); 5.77 (m, 1H); 7.27 (m, 1H); 7.38 (m, 1H); 7.45 (m, 1H); 8.20 (s, 1H); 10.89 (s, 1H).

EXAMPLE 35

(5R)-3-[4-(1,1-Dioxo-3,6-dihydro-2H-thiopyran-4-yl)-3-fluorophenyl]-5-[(4-ethoxy)-1,2,3-triazol-1-ylmethyl]oxazolidin-2-one

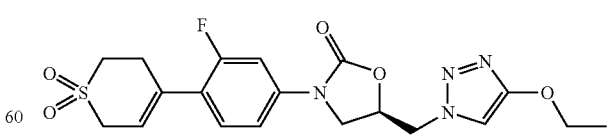

(5R)-3-[4-(1,1-Dioxo-3,6-dihydro-2H-thiopyran-4-yl)-3-fluorophenyl]-5-(azidomethyl)oxazolidin-2-one (Reference Example 2) (733 mg, 2.0 mmol) was dissolved in dry acetonitrile (8 ml). Ethoxyacetylene (420 mg, 6.0 mmol), 2,6-lutidine (236 mg, 2.2 mmol) and copper iodide (38 mg, 10 mmol %) were added and the resulting mixture was stirred at room temperature for 12 hours. Water was added and the mixture was extracted with dichloromethane (3×100 ml). The combined organic layers were concentrated under vacuum and the residue was purified by flash chromatography on silica gel with 5% of methanol in dichloromethane to give the title product (666 mg).

MS (ESP): 437.25 (MH$^+$) for $C_{19}H_{21}FN_4O_5S$ $^1$H-NMR (DMSO-$d_6$) δ: 1.30 (t, 3H); 2.97 (m, 2H); 3.34 (m, 2H); 3.91 (m, 3H); 4.28 (q, 2H); 4.26 (dd, 1H); 4.71 (d, 2H); 5.15 (m, 1H); 5.83 (m, 1H); 7.30 (m, 1H); 7.42 (m, 1H); 7.47 (m, 1H); 7.70 (s, 1H).

EXAMPLE 36

(5R)-3-[4-(1,1-Dioxo-3,6-dihydro-2H-thiopyran-4-yl)-3-fluorophenyl]-5-[(4-bromo)-1,2,3-triazol-1-yl)methyl]oxazolidin-2-one

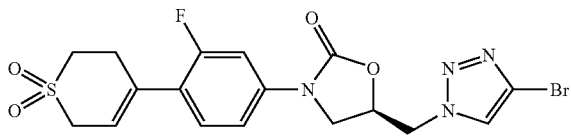

(5R)-3-[4-(1,1-Dioxo-3,6-dihydro-2H-thiopyran-4-yl)-3-fluorophenyl]-5-(azidomethyl) oxazolidin-2-one (Reference Example 2) (1.5 g, 4.1 mmol) and 1-bromo-1-ethenesulfonyl chloride (1.8 g, 8.8 mmol) were heated to 90° C. for one hour with stirring. The reaction mixture was cooled to room temperature, diluted with dichloromethane (10 ml) and applied onto a silica gel column. Elution with hexanes/acetone (2:1 to 1:1) gave 1.46 g (76%) of the title compound as a colourless solid.

MS (ESP): 471/473 (MH$^+$) for $C_{17}H_{16}BrFN_4O_4S$ $^1$H-NMR (DMSO-$d_6$) (500 MHz) δ: 2.98 (m, 2H); 3.34–3.38 (m, 2H); 3.92–3.96 (m, 3H); 4.27 (dd, 1H, J 9.2, 9.2 Hz); 4.87 (d, 2H, J 5.2 Hz); 5.18 (m, 1H); 5.84 (m, 1H); 7.31 (dd, 1H, J 2.2, 8.6 Hz); 7.42 (dd, 1H, J 8.6, 8.8 Hz); 7.47 (dd, 1H, J 2.2, 13.7 Hz); 8.49 (s, 1H).

EXAMPLE 37

(5R)-3-[4-(1,1-Dioxo-3,6-dihydro-2H-thiopyran-4-yl)-3-fluorophenyl]-5-[4-chloro-1,2,3-triazol-1-ylmethyl]oxazolidin-2-one

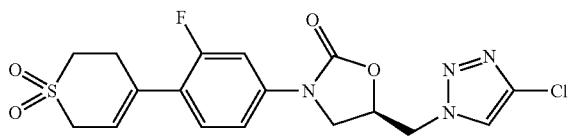

(5R)-3-[4-(1,1-Dioxo-3,6-dihydro-2H-thiopyran-4-yl)-3-fluorophenyl]-5-(azidomethyl)oxazolidin-2-one (Reference Example 2) (1.0 g, 2.7 mmol) and 1-chloro-1-ethenesulfonyl chloride (Intermediate 4) (1.1 g, 6.8 mmol) were heated to 90° C. for one hour with stirring. The reaction mixture was cooled to room temperature, diluted with dichloromethane (10 ml) and applied onto a silica gel column. Elution with hexanes/acetone (1.5:1) gave 0.745 g (64%) of the title compound as a colourless solid.

MS (ESP): 427 (MH$^+$) for $C_{17}H_{16}ClFN_4O_4S$ $^1$H-NMR (DMSO-$d_6$) (300 MHz) δ: 2.96 (m, 2H); 3.29–3.43 (m, 2H); 3.90–3.95 (m, 3H); 4.25 (dd, 1H); 4.83 (d, 2H); 5.16 (m, 1H); 5.82 (m, 1H); 7.29 (dd, 1H); 7.40 (dd, 1H); 7.45 (dd, 1H); 8.45 (s, 1H).

Intermediate 4

1-Chloro-1-ethene sulfonyl chloride

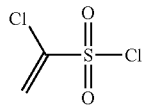

A stirred solution of 1,2-dichloroethanesulfonyl chloride (14.54 g, 73.62 mmol) (Gladschtein et al., Zh.Obshch-.Khim.; 28; 1958; 2107, 2110; Engl. Ed. p. 2145,2146,2148) in dry ether (140 ml) was treated at −60° C. to −50° C. under an atmosphere of nitrogen with 2,6-lutidine (10.30 ml, 88.34 mmol). The stirred reaction mixture was allowed to warm to room temperature, cooled to 0° C. and then treated slowly with dilute aqueous sulfuric acid (1%; 50 ml). The ether phase was separated, washed with dilute aqueous sulfuric acid (1%; 2×60 ml) and brine (3×60 ml), dried over magnesium sulfate, and concentrated under reduced pressure (60 mmHg) to give an oil that was purified by distillation to give 1-chloro-1-ethenesulfonyl chloride (7.2 g, 61%), b.p. 26° C./2 mmHg.

$^1$H-NMR (CDCl$_3$) δ 6.70 (d, J=3.8 Hz, 1H) and 6.22 (d, J=3.8 Hz, 1H).

EXAMPLE 38

(5R)-3-[4-(1,1-Dioxo-3,6-dihydro-2H-thiopyran 4-yl)-3-fluorophenyl]-5-[4-fluoro-1,2,3-triazol-1-ylmethyl]oxazolidin-2-one (5R)-3-[4-(1,1-Dioxo-3,6-dihydro-2H-thiopyran-4-yl)-3-fluorophenyl]-5-(azidomethyl)-oxazolidin-2-one (Reference Example 2) (0.7 g, 1.9 mmol) and (1-fluoroethenyl)-phenylsulfane dioxide (0.7 g, 3.8 mmol) (D. P. Mathews and J. R. McCarthy, JOC 55 (9), 1990, p 2973) were suspended/dissolved in toluene (5 ml) and heated to reflux under stirring for 2 days. The reaction mixture was cooled to room temperature, diluted with dichloromethane, washed with phosphate buffer (pH 7) and dried over sodium sulfate. Chromatography on silica gel with hexanes/acetone (1:1) gave 28 mg (4%) of the title compound as a colourless solid (Rf ~0.25, TLC:hexanes/acetone, 1:1). The major product was the corresponding 5-fluoro-1,2,3-triazoyl compound with an Rf of ~0.2.

MS (ESP): 409.19 (M−H$^-$) for $C_{17}H_{16}F_2N_4O_4S$ $^1$H-NMR (DMSO-$d_6$) (500 MHz) δ: 2.98 (m, 2H); 3.32–3.39 (m, 2H); 3.91–3.95 (m, 3H); 4.27 (dd, 1H); 4.81 (d, 2H); 5.17 (m, 1H); 5.84 (m, 1H); 7.32 (dd, 1H); 7.42 (dd, 1H); 7.48 (dd, 1H); 8.22 (d, 1H).

EXAMPLE 39

(5R)-3-[4-(1,1-Dioxo-3,6-dihydro-2H-thiopyran-4-yl)-3-fluorophenyl]-5-[4-(3-hydroxy-1-propynyl)-1,2,3-triazol-1-ylmethyl]oxazolidin-2-one

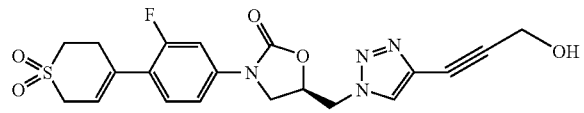

(5R)-3-[4-(1,1-Dioxo-3,6-dihydro-2H-thiopyran-4-yl)-3-fluorophenyl]-5-[4-bromo-1,2,3-triazol-1-ylmethyl]oxazolidin-2-one (Example 36) (235 mg, 0.5 mmol), propargyl alcohol (42 mg, 0.75 mmol), tetrakis(triphenylphosphine) palladium (0) (29 mg, 5 mol %) and copper iodide (5 mg, 5 mol %) were mixed in N-methylpyrrolidone/triethylamine (5 ml, 5:1). The reaction mixture was flushed with nitrogen and heated to 90° C. for 48 hours. The reaction mixture was filtered and extracted with ethyl acetate/water, the organic phase was concentrated and purified by flash chromatography on silica gel with 5% of methanol in dichloromethane to give the title product (27 mg).

MS (ESP): 447.27 (MH$^+$) for $C_{20}H_{19}FN_4O_5S$ $^1$H-NMR (DMSO-d$_6$) δ: 2.96 (m, 2H); 3.34 (m, 2H); 3.93 (m, 2H); 3.93 (m, 1H); 4.22 (dd, 1H); 4.27 (d, 2H); 4.82 (d, 2H); 5.18 (m, 1H); 5.37 (t, 1H); 5.75 (s, 1H); 5.81 (m, 1H); 7.25 (m, 1H); 7.38 (m, 1H); 7.42 (m, 1H); 8.47 (s, 1H).

EXAMPLE 40

(5R)-3-[4-(1,1-Dioxo-3,6-dihydro-2H-thiopyran-4-yl)-3-fluorophenyl]-5-[(4-(2-propynyl)-1,2,3-triazol-1-yl)methyl]oxazolidin-2-one

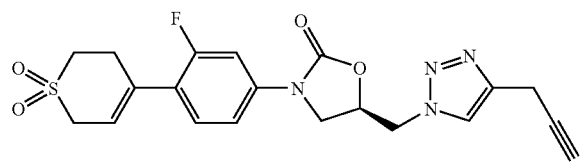

(5R)-3-[4-(1,1-Dioxo-3,6-dihydro-2H-thiopyran-4-yl)-3-fluorophenyl]-5-[4-(3-(trimethylsilyl)-2-propynyl)-1,2,3-triazol-1-ylmethyl]oxazolidin-2-one (251 mg, 0.5 mmol) (Intermediate 5) was dissolved in methanol (10 ml). Potassium hydroxide (1 M, 0.75 ml) was added and the mixture was stirred at room temperature for 4 hours. Aqueous HCl (2M, 0.5 ml) was added, the excess of methanol was evaporated and the residue was extracted with dichloromethane, dried over magnesium sulfate and concentrated to give the title product (220 mg).

MS (ESP): 430.95 (MH$^+$) for $C_{20}H_{19}FN_4O_4S$ $^1$H-NMR (DMSO-d$_6$) δ: 2.96 (m, 2H); 3.34 (m, 2H); 3.72 (s, 2H); 3.92, (m, 3H); 4.22 (dd, 1H); 4.38 (s, 1H); 4.82 (d, 2H); 5.18 (m, 1H); 5.81 (m, 1H); 7.22 (m, 1H); 7.38 (m, 1H); 7.42 (m, 1H); 8.01 (s, 1H).

The intermediate for this compound was prepared as follows:

Intermediate 5

5(R)-3-[4-(1,1-Dioxo-3,6-dihydro-2H-thiopyran-4-yl)-3-fluorophenyl]-5-[4-(3-(trimethylsilyl)-2-propynyl)-1,2,3-triazol-1-ylmethyl]oxazolidin-2-one

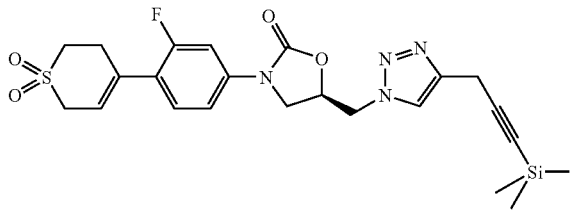

(5R)-3-[4-(1,1-Dioxo-3,6-dihydro-2H-thiopyran-4-yl)-3-fluorophenyl]-5-(azidomethyl)oxazolidin-2-one (Reference Example 2) (620 mg, 1.69 mmol) was reacted with 1-trimethylsilyl-1,4-pentadiyne (461 mg, 3.38 mmol), 2,6-lutidine (199 mg, 3.38 mmol) and copper iodide (10 mmol %) as described for Example 35. Flash chromatography on silica gel with 2.5% of methanol in dichloromethane gave the title product as a white solid (525 mg).

MS (ESP): 502.98 (MH$^+$) for $C_{23}H_{27}FN_4O_4SSi$ $^1$H-NMR (DMSO-d$_6$) δ: 0.00 (s, 9H); 2.96 (m, 2H); 3.34 (m, 2H); 3.68 (s, 2H); 3.91 (m, 3H); 4.28 (dd, 1H); 4.85 (m, 2H); 5.19 (m, 1H); 5.81 (m, 1H); 7.26 (m, 1H); 7.38 (m, 1H); 7.43 (m, 1H); 8.01 (s, 1H).

EXAMPLE 41

5(R)-3-[4-(1,1-Dioxo-3,6-dihydro-2H-thiopyran-4-yl)-3-fluorophenyl]-5-[4-(4-dimethylamino-2-butynyl)-1,2,3-triazol-1-ylmethyl]oxazolidin-2-one

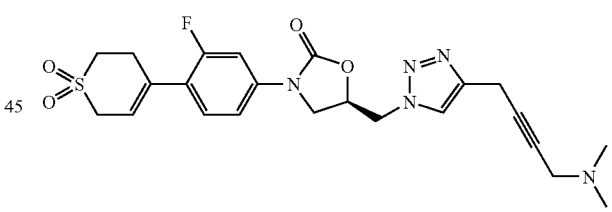

(5R)-3-[4-(1,1-Dioxo-3,6-dihydro-2H-thiopyran-4-yl)-3-fluorophenyl]-5-[4-(prop-2-ynyl)-1,2,3-triazol-1-ylmethyl]oxazolidin-2-one (Example 40) (150 mg, 0.35 mmol) was mixed with formaldehyde (57 mg, 0.7 mmol) in acetonitrile (10 ml), copper iodide (3.5 mg, 10 mmol %) was added, followed by the addition of dimethylamine (32 mg, 0.7 mmol) and the resulting mixture was stirred at 80° C. for 12 hours. The solvent was removed under vacuum and the residue was purified by reverse phase chromatography with 15%–95% acetonitrile in water (containing 0.1% TFA) to give the title product as a TFA salt (85 mg).

MS (ESP): 516.94 (MH$^+$) for $C_{23}H_{26}FN_5O_4S$ $^1$H-NMR (DMSO-d$_6$)(TFA salt) δ: 2.72 (s, 6H); 2.96 (m, 2H); 3.36 (m, 2H); 3.72 (s, 2H); 3.92 (m, 3H); 4.05 (s, 2H); 4.22 (dd, 1H); 4.78 (d, 2H); 5.18 (m, 1H); 5.81 (m, 1H); 7.22 (m, 1H); 7.38 (m, 1H); 7.42 (m, 1H); 8.05 (s, 1H); 9.95 (brs, 1H).

EXAMPLE 42

5(R)-3-[4-(1,1-Dioxo-3,6-dihydro-2H-thiopyran-4-yl)-3-fluorophenyl]-5-[4-(4-diethylamino-2-butynyl)-1,2,3-triazol-1-ylmethyl]oxazolidin-2-one

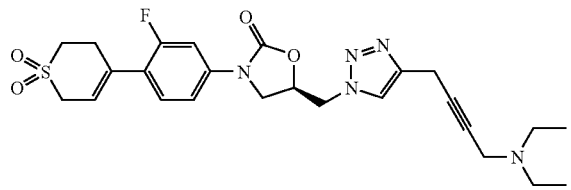

(5R)-3-[4-(1,1-Dioxo-3,6-dihydro-2H-thiopyran-4-yl)-3-fluorophenyl]-5-[4-(2-propynyl)-1,2,3-triazol-1-ylmethyl]oxazolidin-2-one (Example 40) (150 mg, 0.35 mmol) was reacted with diethylamine (51 mg, 0.7 mmol) as described for Example 41 to give 125 mg of the title compound.

MS (ESP): 516.94 (MH$^+$) for $C_{25}H_{30}FN_5O_4S$ $^1$H-NMR (DMSO-$d_6$)(TFA salt) δ: 1.15 (t, 6H); 2.96 (m, 2H); 3.18 (m, 4H); 3.36 (m, 2H); 3.72 (s, 2H); 3.92 (m, 2H); 3.92 (m, 1H); 4.10 (s, 2H); 4.22 (dd, 1H); 4.78 (d, 2H); 5.18 (m, 1H); 5.81 (m, 1H); 7.22 (m, 1H); 7.38 (m, 1H); 7.42 (m, 1H); 8.05 (s, 1H); 9.85 (brs, 1H).

EXAMPLE 43

5(R)-3-[4-(1,1-Dioxo-3,6-dihydro-2H-thiopyran-4-yl-3-fluorophenyl]-5-[4-(4-(2,5-dihydro-1H-pyrrol-1-yl)-2-butynyl)-1,2,3-triazol-1-ylmethyl]oxazolidin-2-one

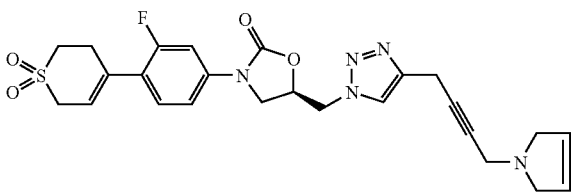

(5R)-3-[4-(1,1-Dioxo-3,6-dihydro-2H-thiopyran-4-yl)-3-fluorophenyl]-5-[4-(2-propynyl)-1,2,3-triazol-1-ylmethyl]oxazolidin-2-one (Example 40) (150 mg, 0.35 mmol) was reacted with 3-pyrroline (48.4 mg, 0.7 mmol) as described for Example 41 to give 50 mg of the title compound.

MS (ESP): 511.93 (MH$^+$) for $C_{25}H_{26}FN_5O_4S$ $^1$H-NMR (DMSO-$d_6$) δ: 2.96 (m, 2H); 3.31 (t, 2H); 3.36 (m, 2H); 3.92 (m, 3H); 4.22 (dd, 1H); 4.45 (d, 2H); 4.78 (d, 2H); 5.18 (m, 1H); 5.65 (m, 2H); 5.81 (m, 1H); 5.92 (d, 2H); 6.68 (d, 2H); 7.22 (m, 1H); 7.38 (m, 1H); 7.42 (m, 1H); 8.01 (s, 1H).

EXAMPLE 44

5(R)-3-[4-(1,1-Dioxo-3,6-dihydro-2H-thiopyran-4-yl)-3-fluorophenyl]-5-[(4-(4-(morpholinyl)-2-butynyl)-1,2,3-triazol-1-yl)methyl]oxazolidin-2-one

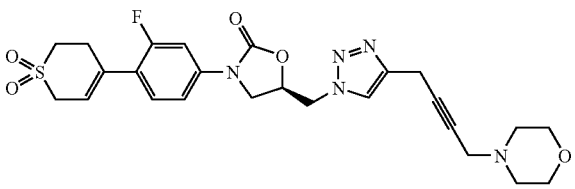

(5R)-3-[4-(1,1-Dioxo-3,6-dihydro-2H-thiopyran-4-yl)-3-fluorophenyl]-5-[4-(2-propynyl)-1,2,3-triazol-1-ylmethyl]oxazolidin-2-one (Example 40) (150 mg, 0.35 mmol) was reacted with morpholine (61 mg, 0.7 mmol) as described for Example 41 to give 175 mg of the title compound.

MS (ESP): 530.89 (MH$^+$) for $C_{25}H_{28}FN_5O_5S$ $^1$H-NMR (pyridine-$d_5$)(TFA salt) δ: 3.66 (t, 4H); 4.26 (m, 2H); 4.43 (d, 2H); 4.57 (m, 2H); 4.84 (t, 4H); 5.04 (s, 2H); 5.19 (m, 2H); 5.25 (m, 1H); 5.40 (dd, 1H); 6.15 (m, 2H); 6.46 (m, 1H); 6.95 (m, 1H); 8.34 (m, 1H); 8.44 (m, 1H); 8.69 (s, 1H); 8.82 (m, 1H); 9.32 (s, 1H).

EXAMPLE 45

(5R)-3-[4-(1,1-Dioxo-3,6-dihydro-2H-thiopyran-4-yl)-3-fluorophenyl]-5-[(4-ethynyl)-1,2,3-triazol-1-yl)methyl]oxazolidin-2-one

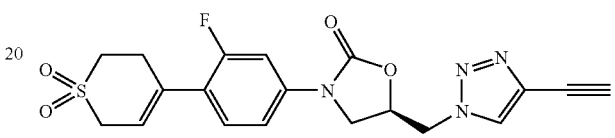

(5R)-3-[4-(1,1-Dioxo-3,6-dihydro-2H-thiopyran-4-yl)-3-fluorophenyl]-5-[4-((2-trimethylsilyl)ethynyl)-1,2,3-triazol-1-ylmethyl]oxazolidin-2-one (Intermediate 6) (11.5 g, 23.5 mmol) was dissolved in methanol (100 ml), potassium hydroxide (1 M, 36 ml) was added and the mixture was stirred at room temperature for 4 hours. Aqueous HCl (2M, 24 ml) was added, the excess of methanol was evaporated and the residue was extracted with dichloromethane. The organic phase was collected and concentrated, the residue was dissolved in a mixture of 10% methanol in dichloromethane, followed by addition of hexane and the resulting precipitate was collected by filtration to give the title product (8.8 g).

MS (ESP): 417.24 (MH$^+$) for $C_{19}H_{17}FN_4O_4S$ $^1$H-NMR (DMSO-$d_6$) δ: 2.96 (m, 2H); 3.34 (m, 2H); 3.92 (m, 3H); 4.22 (dd, 1H); 4.38 (s, 1H); 4.82 (d, 2H); 5.18 (m, 1H); 5.81 (m, 1H); 7.22 (m, 1H); 7.38 (m, 1H) 7.42 (m, 1H); 8.51 (s, 1H).

The intermediate for this compound was prepared as follows:

Intermediate 6

(5R)-3-[4-(1,1-Dioxo-3,6-dihydro-2H-thiopyran-4-yl)-3-fluorophenyl]-5-[4-((2-trimethylsilyl)ethynyl)-1,2,3-triazol-1-ylmethyl]oxazolidin-2-one

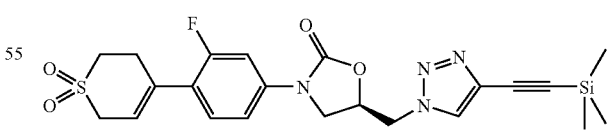

(5R)-3-[4-(1,1-Dioxo-3,6-dihydro-2H-thiopyran-4-yl)-3-fluorophenyl]-5-(azidomethyl)-oxazolidin-2-one (Reference Example 2) (11 g, 30 mmol) was dissolved in dry acetonitrile, buta-1,3-diynyl(trimethyl)silane (5.8 g, 47.5 mmol), 2,6-lutidine (3.53 g, 33 mmol) and copper iodide (571 mg, 10 mmol %) were added and the resulting mixture was stirred at room temperature for 12 hours. The mixture was then poured into water (250 ml) and was stirred for 10 minutes. The formed precipitate was filtered, washed with water and diethyl ether (3×50 ml). The solid was collected and dried under high vaccum to give the title product (11.8 g).

MS (ESP): 489.24 (MH$^+$) for $C_{22}H_{25}FN_4O_4SSi$ $^1$H-NMR (DMSO-d$_6$) δ: 0.01 (s, 9H); 2.96 (m, 2H); 3.34 (m, 2H); 3.91 (m, 3H); 4.28 (dd, 1H); 4.85 (m, 2H); 5.20 (m, 1H); 5.81 (m, 1H); 7.26 (m, 1H); 7.38 (m, 1H); 7.43 (m, 1H); 8.51 (s, 1H).

EXAMPLE 46

(5R)-3-[4-(1,1-Dioxo-3,6-dihydro-2H-thiopyran-4-yl)-3-fluorophenyl]-5-[4-hydroxy-1,2,3-triazol-1-ylmethyl]oxazolidin-2-one

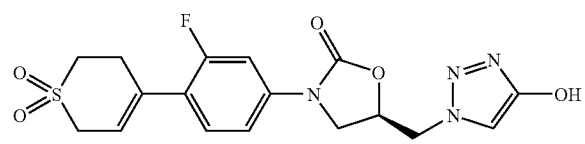

(5R)-3-[4-(1,1-Dioxo-3,6-dihydro-2H-thiopyran-4-yl)-3-fluorophenyl]-5-[4-ethoxy-1,2,3-triazol-1-ylmethyl]oxazolidin-2-one (Example 35) (390 mg, 0.89 mmol) was dissolved in dry dichloromethane (5 ml), cooled down to 0° C., boron tribromide was added via syringe, then the mixture was warmed up to 45° C. and stirred for 48 hours. It was quenched dropwise with water (10 ml) and was extracted with dichloromethane. The combined organic layer was concentrated under vacuum and the residue was purified by reverse phase chromatography with 5%–95% acetonitrile in water (containing 0.1% TFA) to give the title product (221 mg).

MS (ESP): 408.92 (MH$^+$) for $C_{17}H_{17}FN_4O_5S$ $^1$H-NMR (DMSO-d$_6$) δ: 2.92 (m, 2H); 3.34 (m, 2H); 3.91 (m, 1H); 3.92 (m, 2H); 4.22 (dd, 1H); 4.70 (d, 2H); 5.14 (m, 1H); 5.81 (m, 1H); 7.28 (m, 1H); 7.36 (m, 1H); 7.37 (s, 1H); 7.44 (m, 1H); 10.01 (brs, 1H).

EXAMPLE 47

(5R)-3-[3-Fluoro-4-(4-methyl-1H-imidazol-1-yl)phenyl]-5-[4-(fluoromethyl)-1H-1,2,3-triazol-1-ylmethyl]oxazolidin-2-one

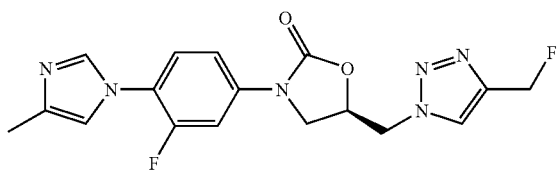

Bis[(2-methoxyethyl)amino]sulfur trifluoride (150 μl, 0.81 mmol) was added to a solution of (5R)-3-[3-fluoro-4-(4-methyl-1H-imidazol-1-yl)phenyl]-5-[4-(hydroxymethyl)-1H-1,2,3-triazol-1-ylmethyl]-1,3-oxazolidin-2-one (Example 48) (222 mg, 0.60 mmol) in dichloromethane (2 ml) at −78° C. The reaction mixture was allowed to gradually warm to room temperature. After 20 hours, the reaction mixture was heated to 40° C. for 3 hours before cooling to room temperature and quenching with methanol. Chromatography on silica gel with 7.5% methanol in dichloromethane gave 36 mg of product.

MS (APCI): 375.0 (MH$^+$) for $C_{17}H_{16}F_2N_6O_2$ $^1$H-NMR (DMSO-d$_6$) δ: 2.15 (s, 3H); 3.94 (dd, 1H); 4.29 (t, 1H); 4.86 (d, 2H); 5.17 (m, 1H); 5.38 (s, 1H); 5.54 (s, 1H); 7.72 (s, 1H); 7.39 (dd, 1H); 7.61 (t, 1H); 7.66 (dd, 1H); 7.86 (s, 1H); 8.37 (d, 1H).

EXAMPLE 48

(5R)-3-[3-Fluoro-4-(4-methyl-1H-imidazol-1-yl)phenyl]-5-[4-(hydroxymethyl)-1H-1,2,3-triazol-1-ylmethyl]oxazolidin-2-one

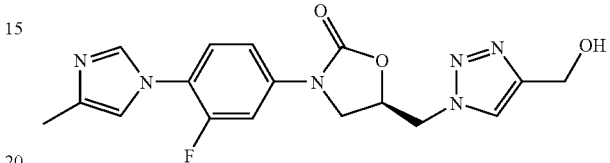

Propargyl alcohol (79 μl, 1.3 mmol), copper sulfate (37 μl of 0.30 M aqueous solution, 11 mmol), and sodium ascorbate (112 μl of 1.0 M aqueous solution, 0.11 mmol) were added to a solution of (5R)-5-(azidomethyl)-3-[3-fluoro-4-(4-methyl-1H-imidazol-1-yl)phenyl]-1,3-oxazolidin-2-one (Intermediate 7) (0.355 g, 1.12 mmol) in ethanol (2 ml) and water (2 ml). The reaction mixture was allowed to stir at room temperature for 24 h. The aqueous phase was extracted three times with dichloromethane, the organic layers were combined and washed once with brine and dried over magnesium sulfate. Chromatography on silica gel with 10% to 14% methanol in dichloromethane gave 0.197 g. of the title compound.

MS (APCI): 373.0 (MH$^+$) for $C_{17}H_{17}FN_6O_3$ $^1$H-NMR (DMSO-d$_6$) δ: 2.15 (s, 3H); 3.92 (dd, 1H); 4.27 (t, 1H); 4.50 (d, 2H); 4.80 (d, 2H); 5.15 (m, 1H); 5.20 (t, 1H); 7.22 (s, 1H); 7.39 (dd, 1H); 7.61 (t, 1H); 7.67 (dd, 1H); 7.86 (s, 1H); 8.01 (s, 1H).

The intermediate for this example was prepared as follows:

Intermediate 7

(5R)-5-(Azidomethyl)-3-[3-fluoro-4-(4-methyl-1H-imidazol-1-yl)phenyl]oxazolidin-2-one

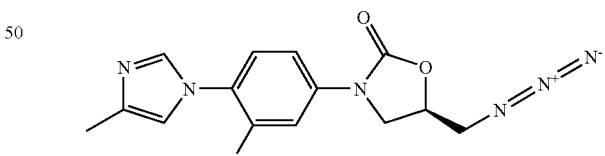

Sodium azide (0.596 g, 9.08 mmol) and 18-crown-6 (0.025 g, 0.095 mmol) were added to a solution of (5R)-3-[3-fluoro-4-(4-methyl-1H-imidazol-1-yl)phenyl]-2-oxo-1,3-oxazolidin-5-ylmethyl methanesulfonate (WO 01/81350) (3.161 g, 8.56 mmol) in DMF (8.5 ml). The reaction mixture was heated to 90° C. under an atmosphere of nitrogen for 19 h. It was poured into a mixture of ethyl acetate and water and was extracted three times with ethyl acetate. The combined organic layers were washed once with brine, dried over sodium sulfate, filtered and the solvent was removed under vacuum to give 1.94 g of product as a white solid.

MS (ESP): 317.13 (MH⁺) for $C_{14}H_{13}FN_6O_2$ ¹H-NMR (DMSO-d₆) δ: 2.16 (s, 3H); 3.70 (dd, 1H); 3.78 (dd, 1H); 3.82 (dd, 1H); 4.18 (t, 1H); 4.92 (m, 1H); 7.21 (s, 1H); 4.75 (dd, 1H); 7.62 (t, 1H); 7.73 (dd, 1H); 7.85 (s, 1H).

EXAMPLE 49

(5R)-3-[4-(1,1-Dioxo-3,6-dihydro-2H-thiopyran-4-yl)-3,5-difluorophenyl]-5[(4-thiomethyl)-1,2,3-triazol-1-ylmethyl]oxazolidin-2-one

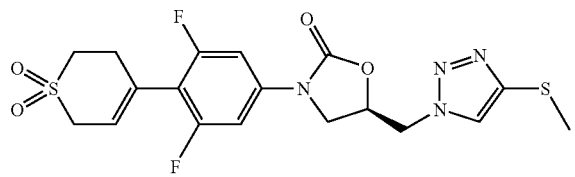

(5R)-3-[4-(3,6-Dihydro-1,1-dioxo-2H-thiopyran-4-yl)-3,5-difluorophenyl]-5-[methylsulfonyloxymethyl]-2-oxazolidinone (WO 01/81350 A1) (2.0 g, 4.59 mmol) and 4-methylthio-1,2,3-triazole (458 mg, 5.51 mmol) were dissolved in DMF (5 ml). Caesium carbonate (2.24 g, 6.89 mmol) was added and the reaction mixture was stirred at room temperature for 12 hours. It was diluted with ethyl acetate (20 ml), washed with saturated aqueous ammonium chloride solution (10 ml), water (10 ml) and brine (10 ml) and dried over magnesium sulfate. The solvent was removed under vacuum and the crude product was purified by flash chromatograph on silica gel with 10% ethyl acetate in toluene to give 66 mg of the title compound.

MS (ESP): 457.12 (MH⁺) for $C_{18}H_{18}F_2N_4O_4S_2$ ¹H-NMR (DMSO-d₆) δ: 2.52 (s, 3H); 2.86 (m, 2H); 3.36 (m, 2H); 3.90 (m, 1H); 3.95 (m, 2H); 4.25 (dd, 1H); 4.80 (d, 2H); 5.18 (m, 1H); 5.78 (s, 1H); 7.32 (d, 2H); 8.22 (s, 1H).

The intermediate for this example:

(5R)-3-[4-(3,6-Dihydro-1,1-dioxido-2H-thiopyran-4-yl)-3,5-difluorophenyl]-5-[methylsulfonyloxymethyl]oxazolidin-2-one

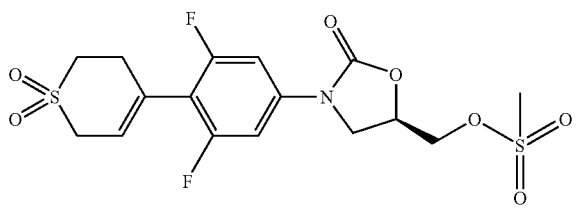

was prepared as described in WO 01/81350 A1 page 97.

EXAMPLE 50

(5R)-3-[4-(1,1-Dioxo-3,6-dihydro-2H-thiopyran-4-yl)-3,5-difluorophenyl]-5-[4-cyclopropyl-1,2,3-triazol-1-ylmethyl]oxazolidin-2-one

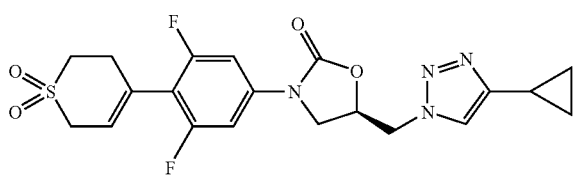

(5R)-3-[4-(1,1-Dioxo-3,6-dihydro-2H-thiopyran-4-yl)-3,5-difluorophenyl]-5-azidomethyloxazolidin-2-one (WO 01/81350 A1) (450 mg, 1.17 mmol) and 1-ethynylcyclopropane (232 mg, 3.51 mmol) were mixed in dry 1,4-dioxane (1.0 ml) in a microwave reaction tube. The resulting mixture was microwaved for 30 minutes at 180° C. The solvent was removed under vacuum and the residue was purified by flash chromatography on silica gel with 5% methanol in dichloromethane to give the title product (552 mg) as a mixture of two regio isomers (4-, 5-substituted triazole, ratio 1:1).

MS (ESP): 450.97 (MH⁺) for $C_{20}H_{20}F_2N_4O_4S$ ¹H-NMR (DMSO-d₆) (for the 4-substituted isomer) δ: 0.66 (m, 2H); 0.89 (m, 2H); 1.95 (m, 1H); 2.86 (m, 2H); 3.37 (m, 2H); 3.89 (m, 1H); 3.95 (m, 2H); 4.24 (dd, 1H); 4.73 (d, 2H); 5.14 (m, 1H); 5.78 (m, 1H); 7.31 (d, 2H); 7.88 (s, 1H).

EXAMPLE 51

(5R)-3-[4-(1,1-Dioxo-3,6-dihydro-2H-thiopyran-4-yl)-3,5-difluorophenyl]-5-[4-(2-hydroxyethyl)-1,2,3-triazol-1-ylmethyl]oxazolidin-2-one

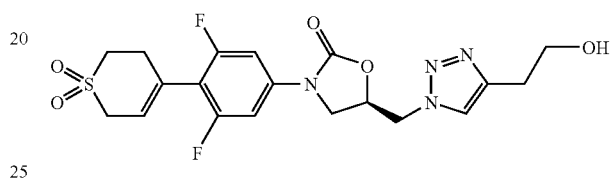

(5R)-3-[4-(1,1-Dioxido-3,6-dihydro-2H-thiopyran-4-yl)-3,5-difluorophenyl]-5-azidomethyloxazolidin-2-one (WO 01/81350 A1) (2.31 g, 6.0 mmol) and 3-butyn-1-ol (1.26 g, 18 mmol) were reacted as described for Example 50. Flash chromatography on silica gel with 50% hexanes in acetone gave the title compound (800 mg) and the corresponding 5-substituted regioisomer (700 mg).

MS (ESP): 455.11 (MH⁺) for $C_{19}H_{20}F_2N_4O_5S$ ¹H-NMR (DMSO-d₆) δ: 2.77 (t, 2H); 2.86 (m, 2H); 3.37 (m, 2H); 3.59 (q, 2H); 3.88 (m, 1H); 3.95 (m, 2H); 4.25 (dd, 1H); 4.70 (t, 1H); 4.76 (d, 2H); 5.16 (m, 1H); 5.78 (s, 1H); 7.32 (d, 2H); 7.93 (s, 1H).

(5R)-3-[4-(1,1-Dioxido-3,6-dihydro-2H-thiopyran-4-yl)-3,5-difluorophenyl]-5-(azidomethyl)oxazolidin-2-one

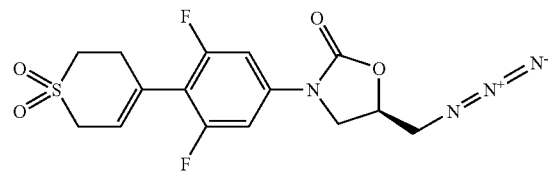

was prepared as described in WO 01/81350 A1 (intermediate for example 86)

EXAMPLE 52

(5R)-3-[4-(1,1-Dioxo-3,6-dihydro-2H-thiopyran-4-yl)-3,5-difluorophenyl]-5-[4-ethenyl-1,2,3-triazol-1-ylmethyl]oxazolidin-2-one

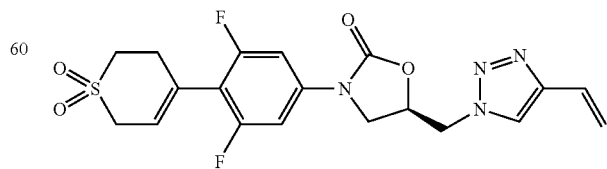

(5R)-3-[4-(1,1-Dioxo-3,6-dihydro-2H-thiopyran-4-yl)-3,5-difluorophenyl]-5-[4-(2-hydroxyethyl)-1,2,3-triazol-1-ylmethyl]oxazolidin-2-one (Example 51) (142 mg, 0.31 mmol) was suspended in dry chloroform (15 ml), thionylchloride (37 mg, 0.93 mmol) was added and the resulting mixture was refluxed for 12 hours. The solvent and eccess of thionylchloride was removed under vacuum and the residue was dissolved in acetonitrile (15 ml), 1,8-diazabicyclo[5.4.0]undec-7-ene (71 mg, 0.47 mmol) was added and the resulting mixture was refluxed for 12 hours. The solvent was removed under vacuum and the residure was purified by flash chromatography on silica gel with 1.5% methanol in dichloromethane to give the title product (100 mg).

MS (ESP): 437.26 (MH$^+$) for $C_{19}H_{18}F_2N_4O_4S$ $^1$H-NMR (DMSO-$d_6$) δ: 2.86 (m, 2H); 3.37 (m, 2H); 3.92 (m, 1H); 3.93 (m, 2H); 4.25 (dd, 1H); 4.81 (d, 2H); 5.18 (m, 1H); 5.31 (d, 1H); 5.78 (m, 1H); 0.86 (d, 1H); 6.72 (m, 1H); 7.32 (d, 2H); 8.28 (s, 1H).

EXAMPLE 53

(5R)-3-[4-(1,1-Dioxo-3,6-dihydro-2H-thiopyran-4-yl)-3,5-difluorophenyl]-5-[4-methoxymethyl-1,2,3-triazol-1-ylmethyl]-1,3-oxazolidin-2-one

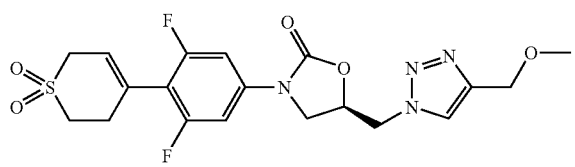

(5R)-3-[4-(1,1-Dioxo-3,6-dihydro-2H-thiopyran-4-yl)-3,5-difluorophenyl]-5-(azidomethyl)-1,3-oxazolidin-2-one (WO 01/81350 A1) (0.50 g, 1.3 mmol), and propargyl methyl ether (1 ml, 11.9 mmol) were combined in toluene (4 ml). The mixture was stirred at 100° C. for 16 hours to give a mixture of two regioisomeric products: tlc Rf's=0.45 and 0.25 respectively (silica gel, 40% acetonitrile in dichloromethane). The mixture was resolved by flash column chromatography on silica gel with gradient 10% to 50% acetonitrile in dichloromethane. The lower migrating material (Rf=0.25) obtained after chromatography was precipitated from dichloromethane solution with ether to give 0.26 g (44%) of the title compound as a white powder. The structure was confirmed by NOE experiments.

MS (ESP): 455.0 (MH$^+$) for $C_{19}H_{20}F_2N_4O_5S$ $^1$H-NMR (DMSO-$d_6$) δ: 2.86 (m, 2H); 3.25 (s, 3H); 3.37 (t, 2H); 3.92 (m, 3H); 4.26 (dd, 1H); 4.46 (s, 2H); 4.83 (d, 2H); 5.19 (m, 1H); 5.77 (m, 1H); 7.32 (d, 2H); 8.16 (s, 1H).

EXAMPLE 54

(5R)-3-[4-(1,1-Dioxo-3,6-dihydro-2H-thiopyran-4-yl)-3,5-difluorophenyl]-5-[(4-chloromethyl)-1,2,3-triazol-1-yl)methyl]oxazolidin-2-one

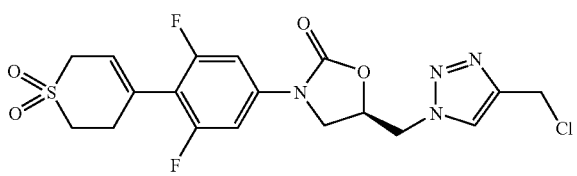

(5R)-3-[4-(1,1-Dioxo-3,6-dihydro-2H-thiopyran-4-yl)-3,5-difluorophenyl]-5-azidomethyloxazolidin-2-one (WO 01/81350 A1) (500 mg, 1.3 mmol) and propargyl chloride (1.5 g, 20 mmol) were added to toluene (1 ml) and heated in a Personal Chemistry Microwave Reactor at 125° C. for 25 minutes. EtOAc (20 ml) was then added and the organic layer was washed with water (2×10 ml) and brine (2×10 ml), dried over sodium sulfate and then concentrated in vacuo. Chromatography on silica gel with 0–5% methanol in dichloromethane gave the title compound (72 mg).

MS (ESP): 459.16 (MH$^+$) for $C_{18}H_{17}ClF_2N_4O_4S$ $^1$H-NMR(DMSO-$d_6$) δ: 2.85 (m, 2H); 3.6 (m, 2H); 3.91 (m, 3H); 4.26 (t, 1H); 4.84 (m, 4H); 5.18 (m, 1H); 5.77 (s, 1H); 7.32 (d, 2H); 8.27 (s, 1H).

EXAMPLE 55

(5R)-3-[4-(1,1-Dioxo-3,6-dihydro-2H-thiopyran-4-yl)-3,5-difluorophenyl]-5-[4-ethynyl-1,2,3-triazol-1-ylmethyl]oxazolidin-2-one

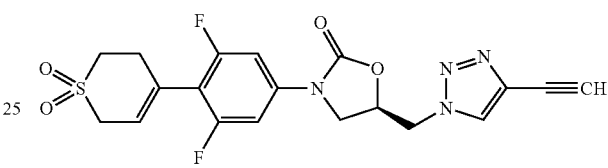

(5R)-3-[4-(1,1-Dioxo-3,6-dihydro-2H-thiopyran-4-yl)-3,5-difluorophenyl]-5-azidomethyloxazolidin-2-one (WO 01/81350 A1) (500 mg, 1.29 mmol) was added to 1,4-dichloro-2-butyne (2 ml) followed by addition of sodium hydroxide (310 mg, 7.74 mmol). The reaction was heated in a Personal Chemistry Microwave Reactor at 125° C. for 25 minutes and then concentrated in vacuo. The residue was purfiried by reverse phase HPLC eluting with 20–95% acetonitrile/water in 30 mintues to give the title compound (10.5 mg).

MS (ESP): 435.20 (MH$^+$) for $C_{19}H_{16}F_2N_4O_4S$ $^1$H-NMR (DMSO-$d_6$) δ: 2.86 (s, 2H); 3.36 (m, 2H); 3.69 (m, 3H); 4.26 (s, 1H); 4.46 (s, 1H); 4.85 (m, 2H); 5.2 (m, 1H); 5.78 (s, 1H); 7.32 (d, 2H); 8.54 (s, 1H).

EXAMPLE 56

(5R)-3-[4-(1,1-Dioxo-3,6-dihydro-2H-thiopyran-4-yl)-3,5-difluorophenyl]-5-[4-(1,1-dimethylethoxy)carbonylaminomethyl)-1,2,3-triazol-1-ylmethyl]oxazolidin-2-one

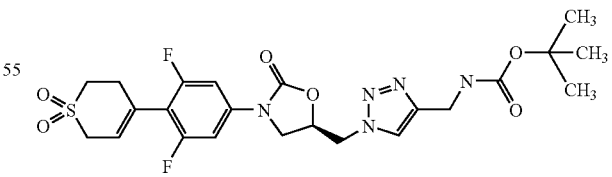

(5R)-3-[4-(1,1-Dioxo-3,6-dihydro-2H-thiopyran-4-yl)-3,5-difluorophenyl]-5-azidomethyloxazolidin-2-one (WO 01/81350 A1) (500 mg, 1.3 mmol) and prop-2-ynyl-carbamic acid tert-butyl ester (1.5 g, 9.7 mmol) were reacted as described for Example 54. Chromatography on silica gel with 0–5% methanol in dichloromethane gave the title product (67.5 mg).

MS (APCI): 539.0 (MH⁻) for $C_{23}H_{27}F_2N_5O_6S$ ¹H-NMR (DMSO-d₆) δ: 1.4 (m, 9H); 2.86 (s, 2H); 3.34 (m, 3H); 3.89 (m, 1H); 3.89 (m, 1H); 3.95 (s, 2H); 4.17 (s, 2H); 4.24 (t, 1H); 4.81 (m, 2H); 5.16 (m, 1H); 5.77 (s, 1H); 7.34 (d, 3H); 7.94 (s, 1H).

EXAMPLE 57

(5R)-3-[4-(1,1-Dioxo-3,6-dihydro-2H-thiopyran-4-yl)-3,5-difluorophenyl]-5-[4-(2-chloroethyl)-1,2,3-triazol-1-ylmethyl]oxazolidin-2-one

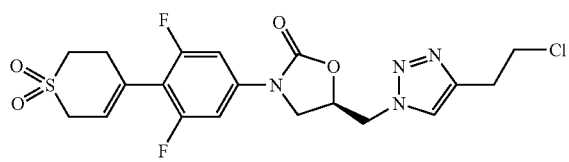

(5R)-3-[4-(1,1-Dioxo-3,6-dihydro-2H-thiopyran-4-yl)-3,5-difluorophenyl]-5-[4-(2-hydroxyethyl)-1,2,3-triazol-1-ylmethyl]oxazolidin-2-one (Example 51) (300 mg, 0.66 mmol) was reacted with thionylchloride (78.5 mg, 1.98 mmol) as described for Example 52. Chromatography on silica gel with 2.5% methanol in dichloromethane gave the title compound (285 mg).

MS (ESP): 473.07 (MH⁺) for $C_{19}H_{19}ClF_2N_4O_4S$ ¹H-NMR(CDCl) δ: 3.04 (m, 2H); 3.21 (t, 2H); 3.25 (m, 2H); 3.79 (m, 2H); 3.85 (m, 2H); 3.96 (m, 1H); 4.16 (dd, 1H); 4.77 (d, 2H); 5.33 (m, 1H); 5.77 (m, 1H); 7.09 (d, 2H); 7.67 (s, 1H).

EXAMPLE 58

(5R)-3-[4-(1,1-Dioxo-3,6-dihydro-2H-thiopyran-4-yl)-3,5-difluorophenyl]-5-[(4-nitro)-1,2,3-triazol-1-ylmethyl]oxazolidin-2-one

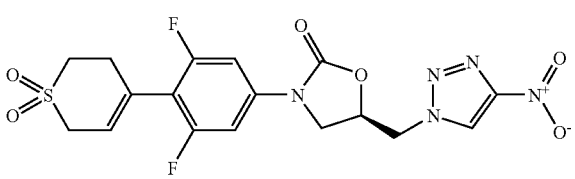

(5R)-3-[4-(1,1-Dioxo-3,6-dihydro-2H-thiopyran-4-yl)-3,5-difluorophenyl]-5-azidomethyloxazolidin-2-one (WO 01/81350 A1) (200 mg, 0.44 mmol) and 1-dimethylamino-2-nitroethene (153 mg, 1.32 mmol) were mixed in dry 1,4-dioxane (0.5 ml) in a microwave reaction tube. The resulting mixture was microwaved for 30 minutes at 150° C. The solvent was removed under vacuum and the residue was purified by flash chromatography on silica gel with with 1.25% of methanol in dichloromethane to give the title product (50 mg).

MS (ESP): 911.15 (2MH⁺) for $C_{17}H_{15}F_2N_5O_6S$ ¹H-NMR (DMSO-d₆) δ: 2.86 (m, 2H); 3.37 (m, 2H); 3.96 (m, 2H); 3.97 (m, 1H); 4.25 (dd, 1H); 4.96 (d, 2H); 5.26 (m, 1H); 5.78 (m, 1H); 7.37 (d, 2H); 9.40 (s, 1H).

EXAMPLE 59

(5R)-3-[4-(1,1-Dioxo-3,6-dihydro-2H-thiopyran-4-yl)-3,5-difluorophenyl]-5-[5-thiomethyl-2H-tetrazol-2-ylmethyl]oxazolidin-2-one

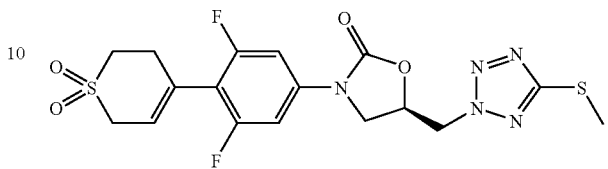

(5R)-3-[4-(3,6-Dihydro-1,1-dioxo-2H-thiopyran-4-yl)-3,5-difluorophenyl]-5-(hydroxymethyl)-2-oxazolidinone (WO 01/81350 A1) (500 mg, 1.39 mmol), 5-(thiomethyl)-1H-tetrazole (178 mg, 1.53 mmol), diisopropylazodicarboxylate (309 mg, 1.53 mmol) and polystyrene-triphenylphosphine (1.73 mmol/g loading: Argonaut Technologies, Inc. Foster City, Calif. USA, 1.02 g, 1.73 mmol) were mixed in dichloromethane (10 ml). It was stirred at room temperature for 12 hours, filtered and washed with aqueous NH₄Cl solution and brine. The solvent was removed under vacuum and the crude product was purified by flash chromatography on silica gel with 2% methanol in dichloromethane to give 232 mg of the title compound.

MS (ESP): 458.14 (MH⁺) for $C_{17}H_{17}F_2N_5O_4S_2$ ¹H-NMR (DMSO-d₆) δ: 2.62 (s, 3H); 2.86 (m, 2H); 3.37 (m, 2H); 3.91 (m, 1H); 3.95 (m, 2H); 4.29 (dd, 1H); 5.18 (m, 2H); 5.31 (m,1H); 5.78 (s, 1H); 7.31 (d, 2H).

The intermediate for this compound was prepared as follows:

(5R)-3-[4-(3,6-Dihydro-1,1-dioxido-2H-thiopyran-4-yl)-3,5-difluorophenyl]-5-(hydroxymethyl)-2-oxazolidinone

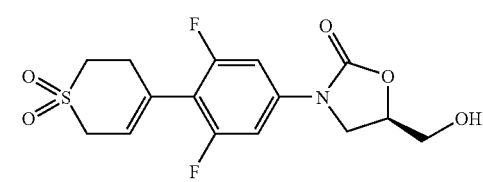

This compound was prepared according to WO 01/81350 A1, page 96.

EXAMPLE 60

(5R)-3-[4-(1,1-Dioxo-3,6-dihydro-2H-thiopyran-4-yl)-3,5-difluorophenyl]-5-[5-(methylcyano)tetrazol-2-ylmethyl]oxazolidin-2-one

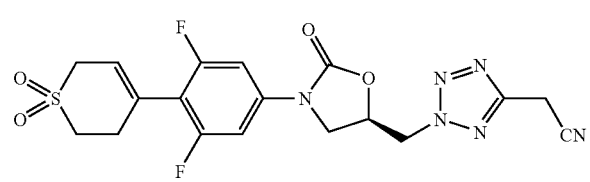

Malonitrile (11 g, 0.167 mol), sodium azide (10.8 g, 0.166 mol), and ammonium chloride (8.92 g, 0.167 mol) were suspended in DMF (50 ml) and heated at 80° C. for 16 hours. The mixture was poured into water, acidified with concentrated HCl, and extracted twice with dichloromethane. The combined organic phases were dried over sodium sulfate and evaporated to give an oily brown residue, which yielded crystals upon drying in vacuo. The crystals were collected and rinsed with dichloromethane to afford 1H-tetrazol-5-ylacetonitrile (CAS# 13616-36-9) as a light brown crystalline solid (2.92 g, 16%).

1H-tetrazol-5-ylacetonitrile (0.27 g, 2.48 mmol), (5R)-3-[4-(1,1-dioxido-3,6-dihydro-2H-thiopyran-4-yl)-3,5-difluorophenyl]-5-(hydroxymethyl)-1,3-oxazolidin-2-one (WO 01/81350 A1) (0.50 g, 1.39 mmol), and triphenylphosphine (0.55 g, 2.1 mmol) were combined in dry tetrahydrofuran (5 ml), and cooled on an ice-water bath. Diisopropylazodicarboxylate (0.41 ml, 2.58 mmol) was added dropwise over several minutes and the mixture was allowed to warm slowly to room temperature with stirring over 16 hours. Methanol (3 ml) was added, followed by evaporation and purification by chromatography on silica gel with 10% to 15% acetonitrile in dichloromethane. The material obtained after chromatography was precipitated from dichloromethane solution with ether to remove residual triphenylphosphine oxide. This gave the title compound as a white powder (0.495 g, 79%).

MS (ESP): 451.0 (MH$^+$) for $C_{18}H_{16}F_2N_6O_4S$ $^1$H-NMR (DMSO-d$_6$) δ: 2.86 (m, 2H); 3.36 (m, 2H); 3.93 (m, 3H); 4.31 (t, 1H); 4.55 (s, 2H); 5.17 (dd, 1H); 5.26 (m, 1H); 5.32 (m, 1H); 5.77 (m, 1H); 7.33 (dm, 2H).

EXAMPLE 61

(5R) 3-[4-(1,1-Dioxo-3,6-dihydro-2H-thiopyran-4-yl)-3,5-difluorophenyl]-5-[5-cyclopropyl-2H-tetrazol-2-ylmethyl]oxazolidin-2-one

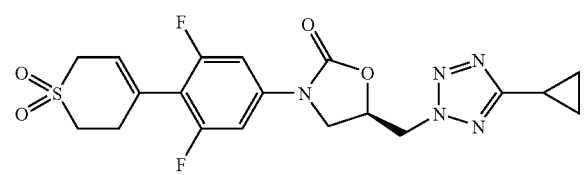

Cyclopropylcarbonitrile (2 ml, 27 mmol) was added to a solution of trimethylsilylazide (4.3 ml, 32.5 mmol) and trimethylaluminum (16 ml of a 2M toluene solution, 32 mmol) at 0° C. The cold bath was removed, the mixture was stirred at room temperature for 15 minutes, then warmed to 80° C. for 16 hours. The solution was carefully added to a slurry of ice and 1N HCl, followed by acidification with concentrated HCl and extraction twice with ethyl acetate. The combined organic phases were washed with saturated NaCl, dried over sodium sulfate, and evaporated to yield a solid residue. Trituration with 1:1 hexane:ethyl acetate gave 5-cyclopropyl-1H-tetrazole (CAS# 27943-07-3) as a white crystalline solid (1.5 g, 51%). 5-cyclopropyl-1H-tetrazole (0.183 g, 1.66 mmol), (5R)-3-[4-(1,1-dioxo-3,6-dihydro-2H-thiopyran-4-yl)-3,5-difluorophenyl]-5-(hydroxymethyl)-1,3-oxazolidin-2-one (WO 01/81350 A1) (0.30 g, 0.84 mmol), polystyrene-triphenylphosphine (1.73 mmol/g, loading: Argonaut Technologies, Inc. Foster City, Calif. USA, 1.46 g, 2.53 mmol) and diisopropylazodicarboxylate (0.33 ml, 1.68 mmol) were reacted as described for Example 58. Purification was carried out by chromatography on silica gel with 10% acetonitrile in dichloromethane. The material obtained after chromatography was precipitated from dichloromethane solution with ether to yield the title compound as a white powder (0.28 g, 74%).

MS (ESP): 452.0 (MH$^+$) for $C_{19}H_{19}F_2N_5O_4S$ $^1$H-NMR (DMSO-d$_6$) δ: 0.83 (m, 2H); 1.05 (m, 2H); 2.18 (m, 1H); 2.87 (bm, 2H); 3.37 (m, 2H); 3.90 (dd, 1H); 3.95 (bs, 2H); 4.28 (t, 1H); 5.04 (dd, 1H); 5.10 (dd, 1H); 5.28 (m, 1H); 5.77 (t, 1H); 7.29 (d, 2H).

The invention claimed is:

1. A compound of the formula (I), or a pharmaceutically-acceptable salt, or an in-vivo-hydrolysable ester thereof,

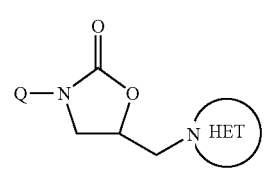

(I)

wherein —N-HET is selected from the structures (Id) or (Ie) below:

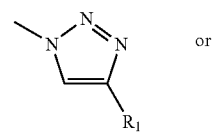

(Id)

or

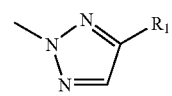

(Ie)

wherein;

R1 is selected from a substituent from the group (R1a) wherein R1 is halogen, hydroxy, (1–4C)alkoxy, (2–4C)alkenyloxy, (2–4C)alkenyl, (2–4C)alkynyl (optionally substituted on the terminal carbon by CH$_2$=CH—, AR2, AR2a or AR2b, wherein AR2, AR2a and AR2b are defined hereinbelow), (3–6C)cycloalkyl, (3–6C)cycloalkenyl, (1–4C)alkyl-S(O)q- (wherein q is 0, 1 or 2);

or R1 is selected from the group (R1b) wherein R1 is a (1–4C)alkyl group which is substituted by one substituent selected from hydroxy, halo, (1–4C)alkoxy, (2–4C)alkenyloxy, (1–4C)alkyl-S(O)q- (wherein q is 0, 1 or 2), AR1-S(O)q- (wherein q is 0, 1 or 2 and AR1 is defined hereinbelow), AR2-S(O)q- (wherein q is 0, 1 or 2), AR2a-S(O)q- (wherein q is 0, 1 or 2), benzyl-S(O)q- (wherein q is 0, 1 or 2), (3–6C)cycloalkyl, (3–6C)cycloalkenyl, (1–4C)alkyl-OCO—NH—;

or R1 is selected from a group of formula (R1c1):

(R1c1) a fully saturated 4-membered monocyclic ring containing 1 or 2 heteroatoms independently selected from O and S (optionally oxidised), and linked via a ring nitrogen or carbon atom; or or R1 is selected from the group (R1d) formyl, (1–4C)alkylcarbonyl, (1–4C)alkoxycarbonyl;

and wherein at each occurrence of an R1 substituent containing an alkyl, alkenyl, alkynyl, cycloalkyl or cycloalkenyl moiety in (R1a), (R1b) or (R1c1) each such moiety is optionally further substituted on an available carbon atom with one, two, three or more substituents independently selected from F, Cl Br, and OH;

Q is Q1;

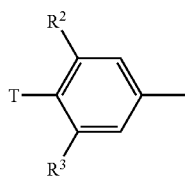

wherein R² and R³ independently selected from H, F, Cl, CF₃, OMe, SMe, Me and Et;
wherein B, is O or S;
wherein T is (TC4):

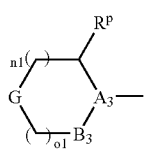

wherein in (TC4): n1 is 1 or 2; o1 is 1 or 2 and n1+o1=2 or 3; >A₃-B₃- is >C=C(Rr)- and G is —S—, —SO—, —SO₂—; Rp is hydrogen (1–4C)alkyl (other than when such substitution is defined by >A₃-B₃), hydroxy, (1–4C) alkoxy or (1–4C)alkanoyloxy;

Rr is (independently where appropriate) hydrogen or (1–4C)alkyl;

and, other than the ring substitution defined by G, >A₃-B₃-and Rp, each ring system may be optionally further substituted on a carbon atom not adjacent to the link at >A₃- by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, ARc-oxymethyl, ARc-thiomethyl, oxo (=O) or independently selected from Rc (if such substituents are not already defined herein in (TC)); and also hydroxy or halo (the last two optional substituents only when G is —O— or —S—);

wherein

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised.

2. A compound of the formula (I) as claimed in claim 1, or a pharmaceutically-acceptable salt or an in-vivo-hydrolysable ester thereof wherein R1 is selected from
(a) hydrogen;
(b) fluorine, chlorine, or bromine;
(C) cyano;
(d) fluoromethyl, chloromethyl, bromomethyl, cyanomethyl, azidomethyl, hydroxymethyl;
(e) difluoramethyl;
(f) trifluoromethyl; and
(g) ethynyl or substituted athynyl.

3. A compound of claim 1 which is a compound of the formula (IB):

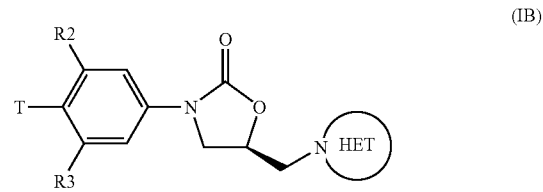

wherein —N-MET is 1,2,3-triazol-1-yl;
R1 is selected from (R1a) and (R1b);
R² and R³ are independently hydrogen or fluoro; and
T is TC4.

4. A compound of claim 3, wherein —N-HET is 1,2,3-triazol-1-yl;
R1 is selected from (R1a), (R1b) and (R1d);
R² and R³ are independently hydrogen or fluoro; and
T is TC4.

5. A compound of the formula (I) as claimed in claim 1, or a pharmaceutically-acceptable salt or an in-vivo hydrolysable ester thereof, which is a compound selected from:
(5R)-3-[4-(1(R,S)-oxo-3,6-dihydro-2H-thiopyran-4-yl)-3-fluorophenyl]-5-[(4-carbonitrile)-1,2,3-triazol-1-yl-methyl]oxazolidin-2-one;
(5R)-3-[4-(1(R,S)-oxo-3,6-dihydro-2H-thiopyran-4-yl)-3-fluorophenyl]-5-[(4-azidomethyl)-1,2,3-triazol-1-yl-methyl]oxazolidin-2-one;
(5R)-3-[4-(1(R,S)-oxo-3,6-dihydro-2H-thiopyran-4-yl)-3-fluorophenyl]-5-[(4-aminomethyl)-1,2,3-triazol-1-ylmethyl]oxazolidin-2-one;
(5R)-3-[4-(1(R,S)-oxo-3,6-dihydro-2H-thiopyran-4yl)-3-fluorophenyl]-5-[(4-(aminocarbonyl)-1,2,3-triazol-1-ylmethyl]oxazolidin-2-one;
(5R)-3-[4-(1(R,S)-oxo-3,6-dihydro-2H-thiopyran-4-yl)-3-fluorophenyl]-5-[(4-(methoxycarbonyl)aminomethyl)-1,2,3-triazol-1-ylmethyl]oxazolidin-2-one;
(5R)-3-[4-(1,1-dioxo-3,6-dihydro-2H-thiopyran-4-yl)-3-fluorophenyl]-5-{[4-[(aminomethaneiminiumbromide) thiomethyl]-1,2,3-triazol-1-yl}methyl]oxazolidin-2-one;
(5R)-3-[4-(1,1-dioxo-3,6-dihydro-2H-thiopyran-4-yl)-3-fluorophenyl]-5-[4-(1H-1,2,3-triazol-4-ylthiomethyl)-1,2,3-triazol-1-ylmethyl]oxazolidin-2-one;
(5R)-3-[4-(1,1-dioxo-3,6-dihydro-2H-thiopyran-4-yl)-3-fluorophenyl]-5-[4-[(1H-imidazol-2-ylthio)methyl]-1,2,3-triazol-1-ylmethyl]oxazolidin-2-one;
(5R)-3-[4-(1,1-dioxo-3,6-dihydro-2H-thiopyran-4-yl)-3-fluorophenyl]-5-[4-(dimethylamino)methyl-1,2,3-triazol-1-ylmethyl]oxazolidin-2-one;

(5R)-3-[4-(1,1-dioxo-3,6-dihydro-2H-thiopyran-4-yl)-3-fluorophenyl]-5-[4-(2-(3-methyl-5-isoxazolyl)ethynyl)-1,2,3-triazol-1-ylmethyl]oxazolidin-2-one;
(5R)-3-[4-(1,1-dioxo-3,6-dihydro-2H-thiopyran-4-yl)-3-fluorophenyl]-5-[4-(2-(ethylmethylamino)-2-axoethyl)-1,2,3-triazol-1-ylmethyl]oxazolidin-2-one;
(5R)-3-[4-(1,1-dioxo-3,6-dihydro-2H-thiopyran-4-yl)-3-fluorophenyl]-5-[(4-(2-(dimethylamino)-2-oxoethyl)-1,2,3-triazol-1-yl)methyl]oxazolidin-2-one;
(5R)-3-[4-(1,1-dioxo-3,6-dihydro-2H-thiopyran-4-yl)-3-fluorophenyl]-5-[4-(ethylaminocarbonyloxymethyl)-1,2,3-triazol-1-ylmethyl]oxazolidin-2-one;
(5R)-3-[4-(1,1-dioxo-3,6-dihydro-2H-thiopyran-4-yl)-3-fluorophenyl]-5-[4-amino)-1,2,3-triazol-1-ylmethyl]oxazolidin-2-one;
(5R)-3-(1,1-dioxo-3,6-dihydro-2H-thiopyran-4-yl)-3-fluorophenyl)-5-[(4-acetylamino)-1,2,3-triazol-1-yl)methyl]oxazolidin-2-one;
5(R)-3-[4-(1,1-dioxo-3,6-dihydro-2H-thiopyran-4-yl)-3-fluorophenyl-5-[4-(4-dimethylamino-2-butynyl)-1,2,3-triazol-1-ylmethyl]oxazolidin-2-one;
5(R)-3-[4-(1,1-dioxo-3,6-dihydro-2H-thiopyran-4-yl)-3-fluorophenyl]-5-[4-(4-diethylamino-2-butynyl)-1,2,3-triazol-1-ylmethyl]oxazolidin-2-one;
5(R)-3-[4-(1,1-dioxo-3,6-dihydro-2H-thiopyran-4-yl)-3-fluorophenyl]-5-(4-(4-(2,5-dihydro-1H-pyrrol-1-y)-2-butynyl)-1,2,3-triazol-1-ylmethyl]oxazolidin-2-one;
5(R)-3-[4-(1,1-dioxo-3,6-dihydro-2H-thiopyran-4-yl)-3-fluorophenyl]-5-[(4-(4-(morpholinyl)-2-butynyl)-1,2,3-triazol-1-yl)methyl]oxazolidin-2-one;
(5R)-3-[4-(1,1-dioxo-3,6-dihydro-2H-thiopyran-4-yl)-3,5-difluorophenyl]-5-[4-(1,1-dimethylethoxy)carbonylaminomethyl)-1,2,3-triazol-1-ylmethyl]oxazolidin-2-one; and
(5R)-3-[4-(1,1-dioxo-3,6-dihydro-2H-thiopyran-4-yl)-3,5-difluorophenyl]-5-[(4-nitro)-1,2,3-triazol-1-ylmethyl]oxazolidin-2-one.

6. A pro-drug of a compound as claimed in claim 1.

7. A pharmaceutical composition which comprises a compound of the invention as claimed in claim 1, or a pharmaceutically-acceptable salt or an in-vivo hydrolysable ester thereof and a pharmaceutically-acceptable diluent or carrier.

8. A process for the preparation of a compound of formula (I) as claimed in claim 1 or pharmaceutically acceptable salts or in-vivo hydrolysable esters thereof, which process comprises one of processes (a) to (h);
(a) by modifying a substituent in, or introducing a new substituent into, the substituent group R1 of HET of another compound of formula (I);
(b) by reaction of a compound of formula (II):

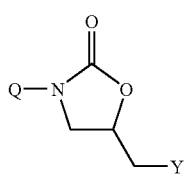

(II)

wherein Y is a displaceable group with a compound of the formula (III):

HET  (III)

wherein HET (of formula (Ia) to (If), already substituted and optionally protected) is HET-H free-base form or HET-anion formed from the free base form; or
(c) by reaction of a compound of the formula (IV):

Q-z  (IV)

wherein Z is an isocyanate, a nine or urethane group with an epoxide of the formula (V); or with a related compound of formula (VI) where
the hydroxy group at the internal C-atom is conventionally protected and where the leaving group Y at the terminal C-atom is a conventional leaving group; or

(V)

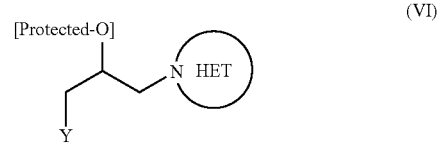

(VI)

(d) (i) by coupling, using catalysis by transition metals such as palladium(0), of a compound of formula (VII):

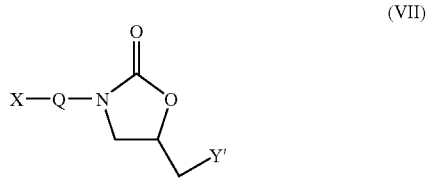

(VII)

wherein Y' is a group HET as hereinbefore defined, X is a replaceable substituent;
with a compound of the formula (VIII), or an analogue thereof, which is suitable to give a T substituent as defined by (TA)-(TE), in which the link is via an sp² carbon atom (D=CH=C-Lg where Lg is a leaving group; or as in the case of reactions carried out under Heck reaction conditions Lg may also be hydrogen) or in which the link is via an N atom (D=NH)

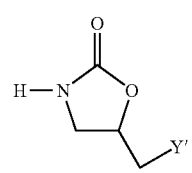

(VIII)

where $T_1$ and $T_2$ may be the same or different or may together with D form a ring of type T;
(d) (II) by coupling, using catalysis by transition metals such as palladium(0), of a compound of formula (VIIA):

(VIIA)

wherein Y' is a group HET as hereinbefore defined, with a compound [Aryl]-X, where X is a replaceable substituent;

(e) Where N-HET is 1,2,3-triazole by cycloaddition via the azide (wherein Y in (II) is azide), with a substituted acetylene or a masked acetylene;

(f) Where N-HET is 1,2,3-triazole by reaction of a compound of formula (II) where Y=NH$_2$ (primary amine) with a compound of formula (IX), namely the arenesulfonylhydrazone of a methyl ketone that is further geminally substituted on the methyl group by two substituents (Y' and Y' ) capable of being eliminated from this initial, and the intermediate, substituted hydrazones as HY' and HY'' (or as conjugate bases thereof);

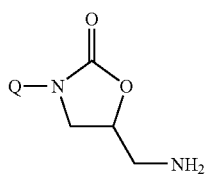

(II : Y = NH2)

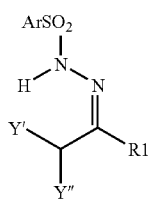

(IX)

(g) where N-HET is 1,2,3-triazole regioselective synthesis may be carried out by cycloaddition via the azide (wherein Y in (II) is azide) with a terminal alkyne using Cu(I) catalysis to give 4-substituted 1,2,3-triazoles;

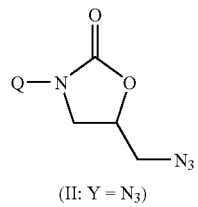

(II: Y = N$_3$)

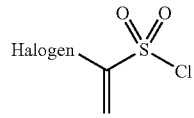

(XIII)

(h) where N-HET is 1,2,3-triazole regioselective synthesis may be carried out by cycloaddition via the azide (wherein Y in (II) is azide) with an alpha-halovinyl-sulfonylchloride (XIII);

and thereafter if necessary: (I) removing any protecting groups; (ii) forming a pharmaceutically-acceptable salt; (iii) forming an in-vivo hydrolysable ester.

\* \* \* \* \*